(12) United States Patent
Kim et al.

(10) Patent No.: US 11,179,441 B2
(45) Date of Patent: Nov. 23, 2021

(54) CILIARY NEUROTROPHIC FACTOR RECEPTOR LIGANDS AND METHODS OF USING THE SAME

(71) Applicant: The Board of Trustees of the Leland Stanford Junior University, Stanford, CA (US)

(72) Inventors: Jun Woo Kim, Mountain View, CA (US); Jennifer R. Cochran, Stanford, CA (US); Eric Alejandro Sweet, San Francisco, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/465,726

(22) PCT Filed: Dec. 6, 2017

(86) PCT No.: PCT/US2017/064934
§ 371 (c)(1),
(2) Date: May 31, 2019

(87) PCT Pub. No.: WO2018/128745
PCT Pub. Date: Jul. 12, 2018

(65) Prior Publication Data
US 2019/0328837 A1    Oct. 31, 2019

Related U.S. Application Data

(60) Provisional application No. 62/515,746, filed on Jun. 6, 2017, provisional application No. 62/443,554, filed on Jan. 6, 2017.

(51) Int. Cl.

| | | |
|---|---|---|
| *A61K 38/18* | (2006.01) | |
| *A61K 47/64* | (2017.01) | |
| *C07K 14/475* | (2006.01) | |
| *C12N 15/74* | (2006.01) | |
| *C12N 15/85* | (2006.01) | |
| *C07K 14/52* | (2006.01) | |

(52) U.S. Cl.
CPC ........ *A61K 38/185* (2013.01); *A61K 47/6425* (2017.08); *C07K 14/475* (2013.01); *C07K 14/52* (2013.01); *C12N 15/74* (2013.01); *C12N 15/85* (2013.01); *C07K 2317/92* (2013.01); *C07K 2319/033* (2013.01); *C12N 2015/8518* (2013.01)

(58) Field of Classification Search
CPC .............. A61K 38/185; A61K 47/6425; C07K 14/475; C07K 14/52; C07K 2319/033; C07K 2319/30; C12N 2015/8518; C12N 15/74; C12N 15/85
See application file for complete search history.

(56) References Cited

U.S. PATENT DOCUMENTS

| | | | |
|---|---|---|---|
| 5,741,772 A * | 4/1998 | Chang | C07K 14/475 |
| | | | 530/350 |
| 6,756,357 B1 | 6/2004 | Laufer et al. | |
| 7,579,323 B1 | 8/2009 | Anderson et al. | |
| 8,129,407 B2 | 3/2012 | Kowalczyk et al. | |
| 2003/0176346 A1 | 9/2003 | Ciliberto et al. | |

FOREIGN PATENT DOCUMENTS

WO    2004026293    4/2004

OTHER PUBLICATIONS

Kim et al., Engineering a potent receptor superagonist or antagonist from a novel IL-6 family cytokine ligand, Jun. 23, 2020, PNAS 117(25): 14110-14118 (Year: 2020).*
Cochran (2016) "Cell-Binding Assays for Determining the Affinity of Protein-Protein Interactions: Technologies and Considerations" Methods Enzymol., 580:21-44.
Taylor et al. (2005) "A microfluidic culture platform for CNS axonal injury, regeneration and transport" Nat. Methods, 2:599-605.
Van Deveter and Wittrup (2014) "Yeast surface display for antibody isolation: library construction, library screening, and affinity maturation" Methods Mol. Biol., 11321:151-181.

* cited by examiner

*Primary Examiner* — Kimberly Ballard
(74) *Attorney, Agent, or Firm* — Brian E. Davy; Bozicevic, Field & Francis LLP

(57) ABSTRACT

Provided are ciliary neurotrophic factor receptor (CNTFR) ligands. In certain aspects, a CNTFR ligand of the present disclosure exhibits increased affinity for CNTFR relative to the corresponding wild-type CNTFR ligand. In certain aspects, a CNTFR ligand of the present disclosure results in reduced binding affinity of glycoprotein 130 (gp130), leukemia inhibitory factor receptor (LIFR), or both, for a complex including the CNTFR ligand and CNTFR, relative to the binding affinity for a complex including the corresponding wild-type CNTFR ligand and CNTFR. In certain aspects, a CNTFR ligand of the present disclosure has both of the aforementioned properties. Also provided are pharmaceutical compositions including the CNTFR ligands, as well as methods of using the CNTFR ligands.

20 Claims, 26 Drawing Sheets

Specification includes a Sequence Listing.

FIG. 4
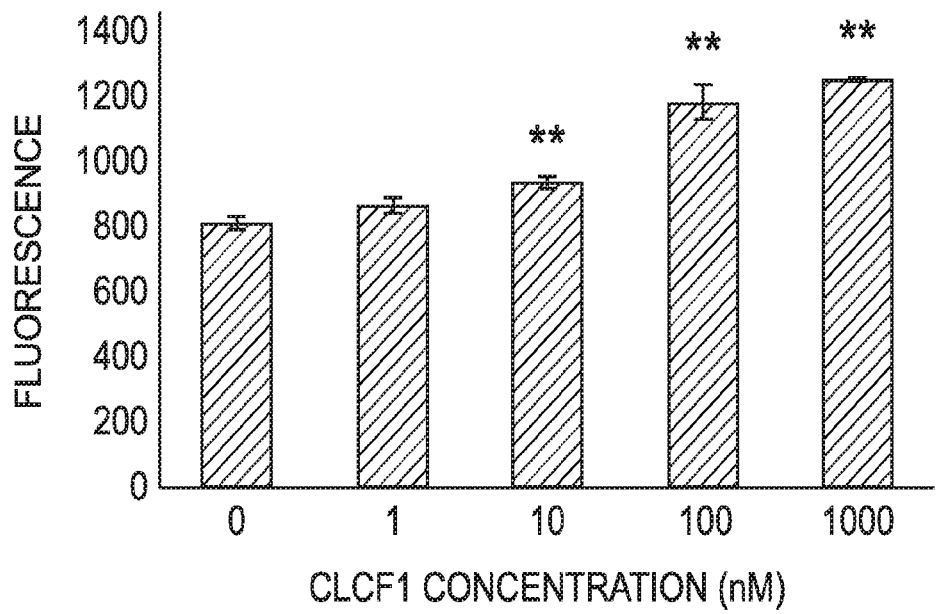
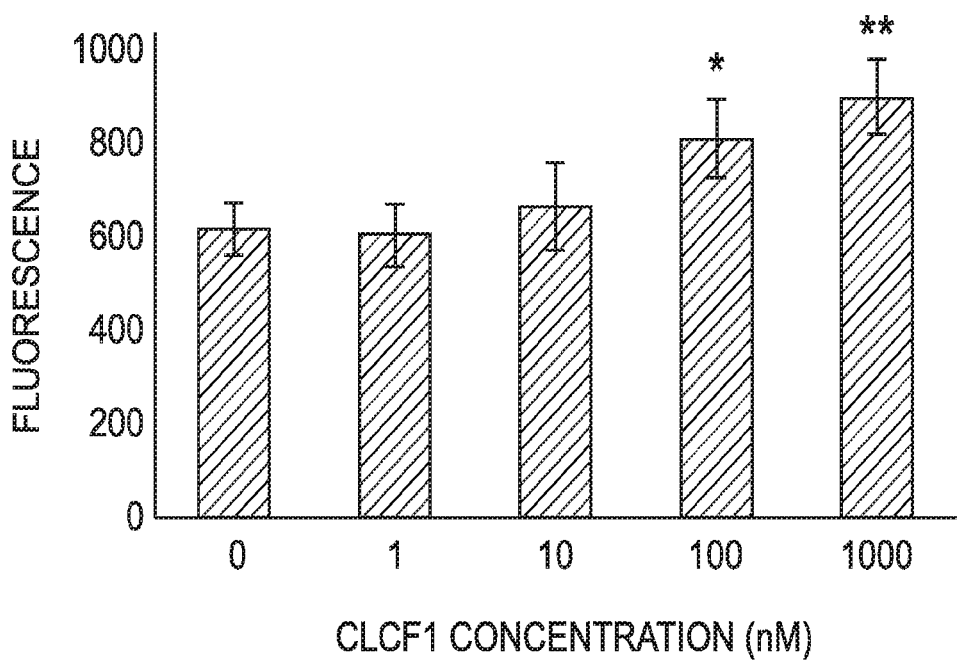

FIG. 6

| SAMPLE | 8 P | 25 H | 32 G | 55 E | 62 V | 69 S | 71 S | 74 L | 86 L | 88 C | 96 Q | 99 T | 107 A | 108 H | 112 S | 119 S | 133 Q | 142 W | 148 H | 156 D | 158 F | 162 K | 166 T | 169 W | 173 K | 179 K | 180 K | 183 Q | 184 P | 189 V |
|---|---|---|---|---|---|---|---|---|---|---|---|---|---|---|---|---|---|---|---|---|---|---|---|---|---|---|---|---|---|---|
| WT | | | | | | | | | | | | | | | | | | | | | | | | | | | | | | |
| #1 | | | | | | | | | | | R | | | | | | | | R | | | | | | | | | | | |
| #2 | | | | | | | | | | | R | | | | | | | | | E | | | | | | | | | | |
| #3 | | Y | | | | | | Q | | | R | | | | | | | | | | | | | | | | | | | |
| #4 | | | | | | | S | | | | R | | | | | | | | | | | | | | | | | | | |
| #5 | T | | | | I | | | | | | R | | | | | | | | | | | | | | | | | | | |
| #6 | | | | | | | | | F | | R | | | | | | | S | | | | | | | | | | | | |
| #7 | | | | | | G | | | | | R | | | | G | | | | | | | | | | | | | | | |
| #8 | | | | | | | | | | | R | | | R | | N | | | | | | | | | | | | | | |
| #9 | | | | | | | | | | | R | | | | | | R | | R | | | | | | | | | | | |
| #10 | | | | | | | | | | W | R | | | | | | | | | | | | | | | | | | | |
| #11 | | | | | | | | | F | | R | | | R | | | | | | | | | | | | | | | | |
| #12 | | | | | | | | | | | R | | | | | | | | | | | K | | | | | | | | |
| #13 | | | | | | | | | | | R | | | | | | | S | | | | | | | | | | | | |
| #14 | | | R | | | | | | | | R | | | | | | | | | | | | | | | | | | | |
| #15 | | | | G | | | | | | | | P | | | | | | | | | | | | L | | | | | | |
| #16 | | | | | | | | | | | R | | | | | | | | | | Y | | | | | | | | S | |
| #17 | | | | | | | | | | R | R | | | | | | | | | | | | | | | R | | L | | |
| #18 | | | | | | | | | F | | R | | | | | | | | | | | | A | | | | R | | | |
| #19 | | R | | | | | | | | | R | | | | | | | | | | | | | | R | | | | | |
| #20 | T | | | | | | | | | | R | | | | | | | | | | | | | | | | | | | |

FIG. 8 (Cont.)
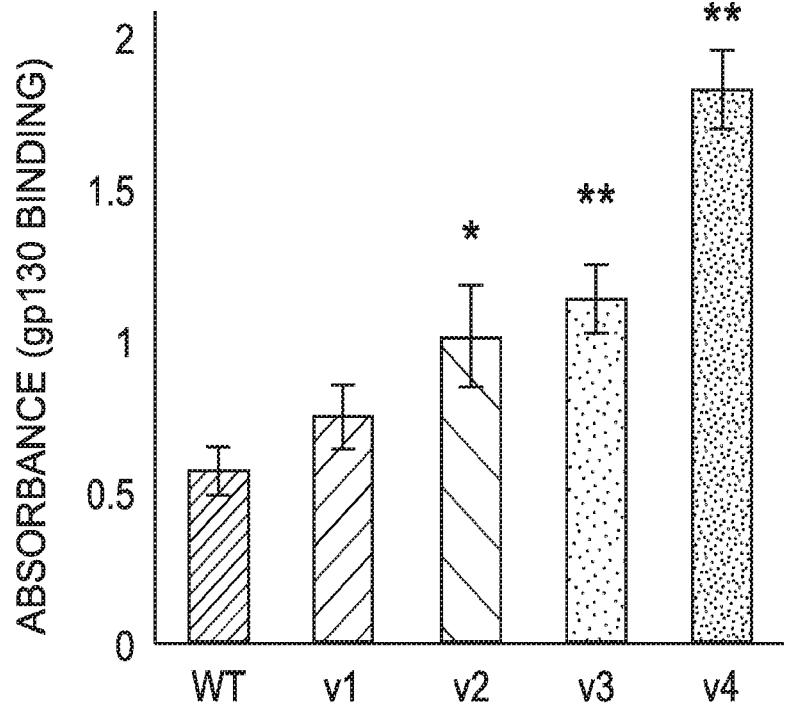
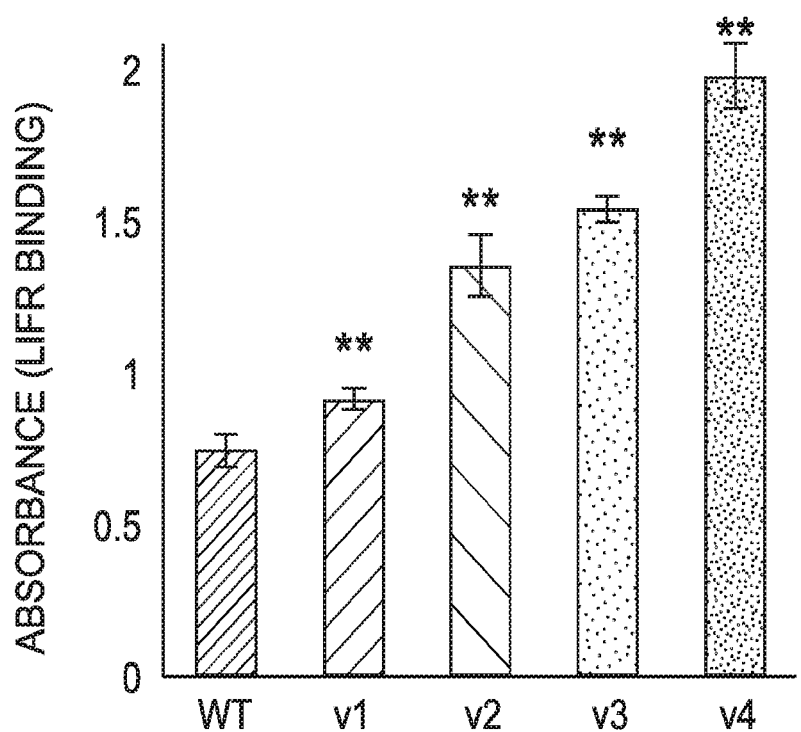

FIG. 10
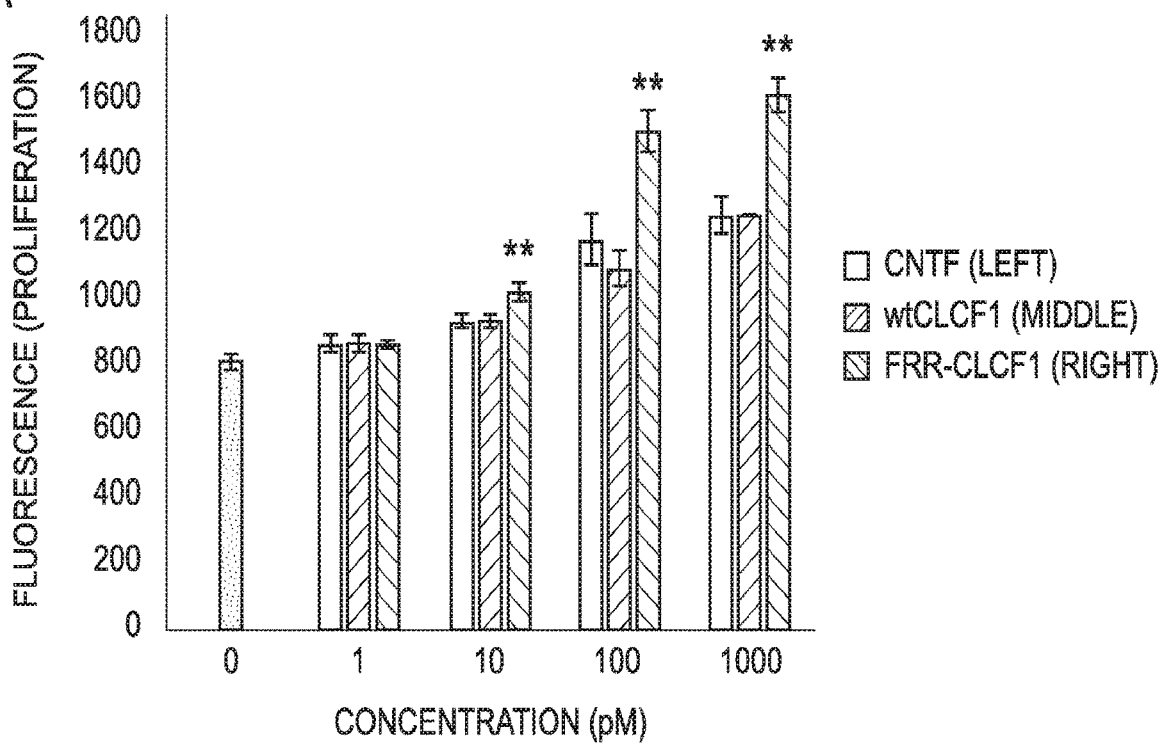
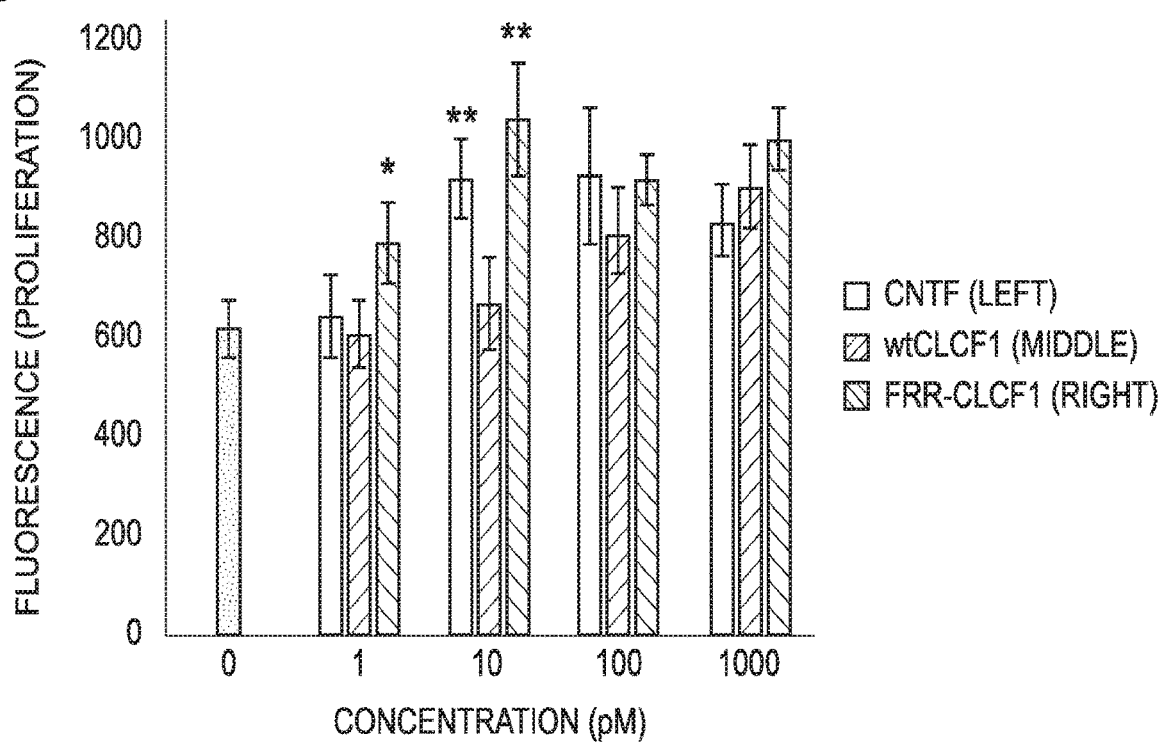

FIG. 14

| CLCF1 | 7 | 22 | 25 | 32 | 62 | 71 | 74 | 86 | 88 | 96 | 111 | 112 | 133 | 139 | 142 | 148 | 151 | 152 | 156 | 158 | 162 | 169 | 180 | 183 |
|---|---|---|---|---|---|---|---|---|---|---|---|---|---|---|---|---|---|---|---|---|---|---|---|---|
| wt | P | Y | H | H | V | N | L | L | C | Q | T | S | Q | E | W | H | F | S | D | F | K | W | K | Q |
| 1 |   |   |   |   |   |   |   |   |   |   |   |   |   |   |   |   |   |   |   |   |   | L | R |   |
| 2 |   | C |   |   |   |   |   |   |   |   |   |   |   |   |   |   |   |   |   |   |   | L | R |   |
| 3 |   |   |   |   |   | S |   |   |   | R |   |   | R |   |   |   |   |   |   |   |   | L |   |   |
| 4 |   |   |   |   |   |   |   | F |   | R |   |   |   |   |   |   |   |   |   |   |   | L | R |   |
| 5 |   |   | Y |   |   |   |   |   |   |   |   |   |   |   |   |   |   |   |   | Y | R | L | R |   |
| 6 |   |   |   | R |   |   |   | F |   | R |   |   |   |   |   |   |   |   |   |   |   |   | R |   |
| 7 |   |   | R | R |   | S |   | F |   | R |   |   |   |   |   |   |   |   |   |   |   |   | R |   |
| 8 |   |   |   |   | I |   |   | F |   | R | A | G |   | G | S | R |   |   |   |   |   |   | R |   |
| 9 |   |   |   |   | I |   |   |   |   | R |   |   |   |   |   |   |   |   |   |   |   | L |   |   |
| 10 |   | C |   | R |   | S |   | F |   | R |   |   |   |   |   |   |   |   |   |   |   | L | R |   |
| 11 |   |   |   |   | I |   | Q | F |   | R |   |   |   |   | S | R |   |   |   |   |   | L | R |   |
| 12 |   |   |   |   | I |   |   | F | R | R |   |   |   |   |   |   |   |   |   |   |   | L | R |   |
| 13 |   |   |   |   | I |   |   | F |   | R |   |   |   |   |   |   |   |   |   |   |   | L | R |   |
| 14 |   |   |   | R |   |   |   | F |   | R |   |   |   |   |   |   |   |   |   |   | R | L | R |   |
| 15 |   |   |   |   | I |   |   | F |   | R |   |   |   |   |   |   |   |   |   |   |   | L | R | L |
| 16 |   |   |   |   | I |   |   | F |   | R |   |   |   |   |   |   |   | G | E |   |   | L | R |   |
| 18 |   |   |   |   |   |   | Q | F |   | R |   |   |   |   |   | R |   |   |   |   | R |   | R | R |
| 19 |   |   |   |   |   |   |   | F |   | R |   | G |   |   | S | R |   |   |   |   |   | L | R | L |
| 20 |   |   |   |   |   |   |   | F |   | R |   |   |   |   |   | R |   |   |   |   |   | L | R |   |
| 21 | T |   |   |   |   |   |   | F |   | R |   |   |   |   |   |   |   |   |   |   |   | L |   |   |
| 22 |   | R |   | R |   |   |   | F | R | R |   |   |   |   |   | R |   |   |   |   | R | L |   | L |

FIG. 18
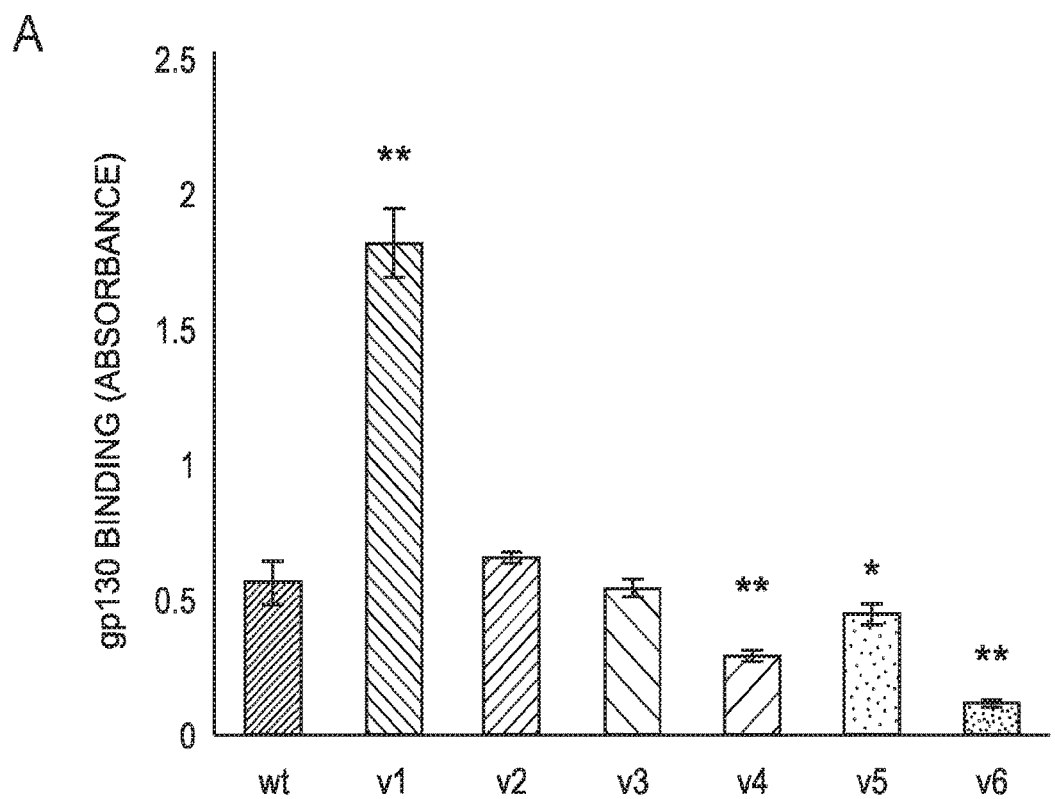
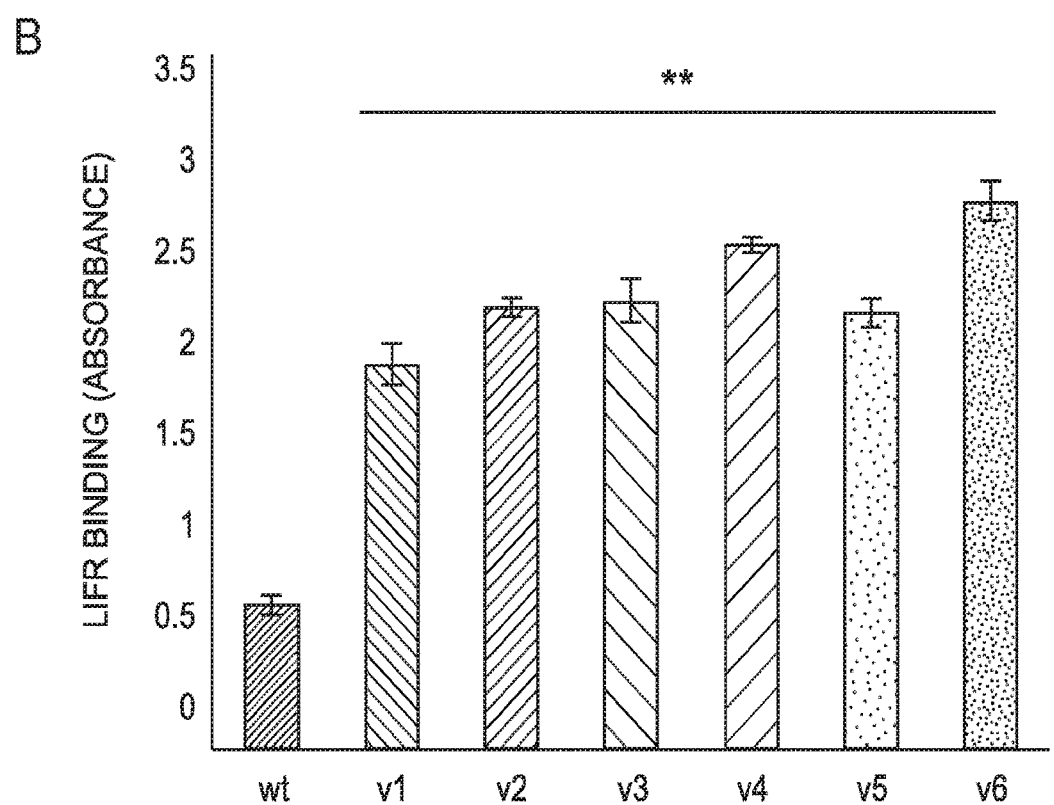

FIG. 22
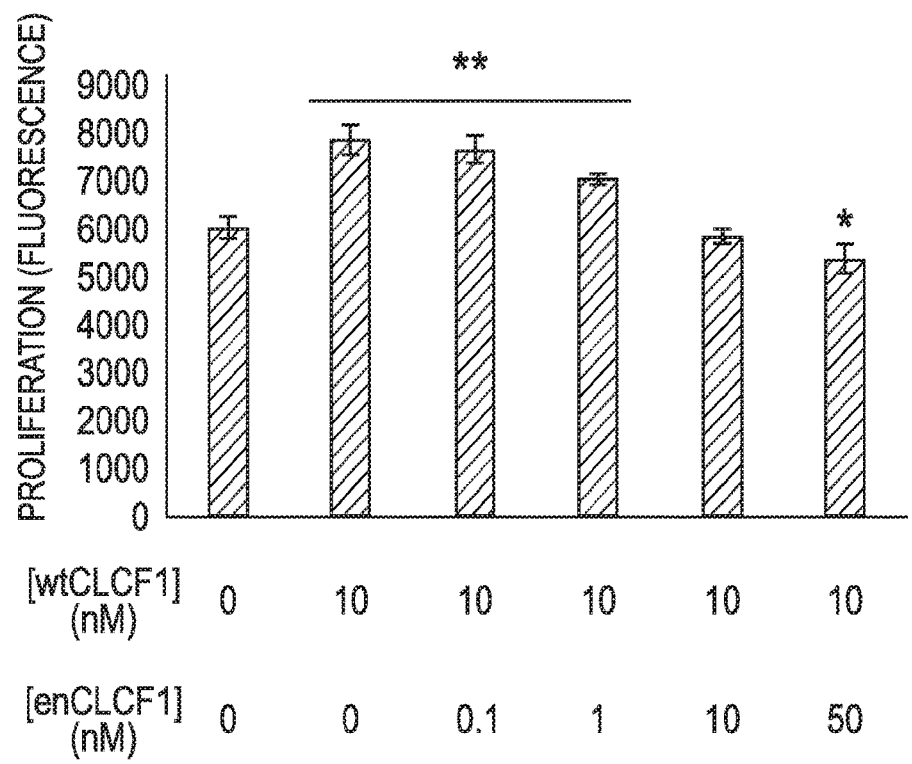
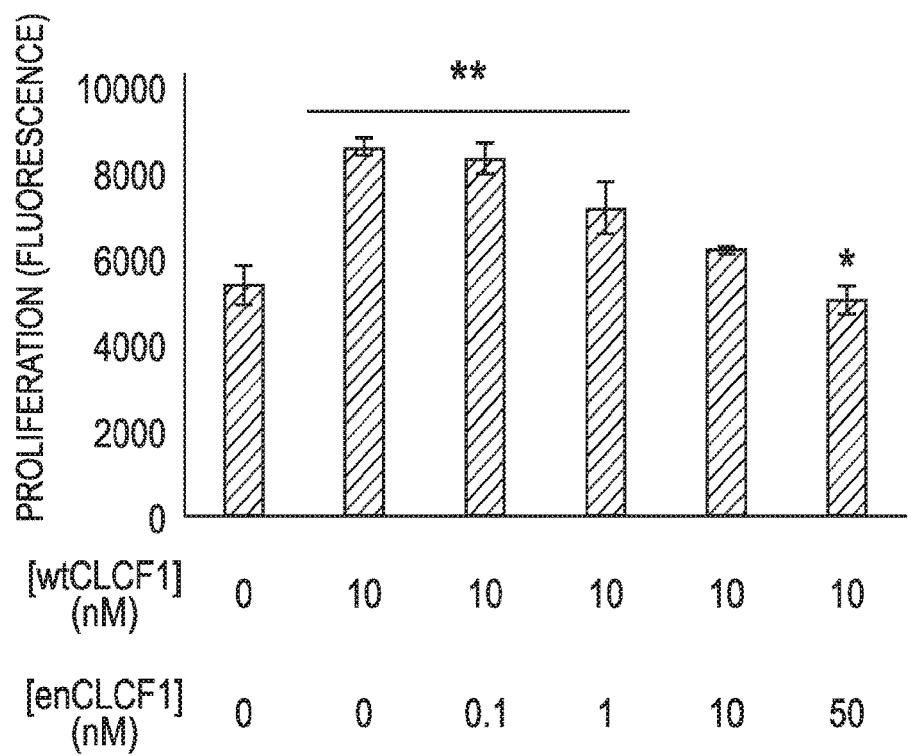

FIG. 23
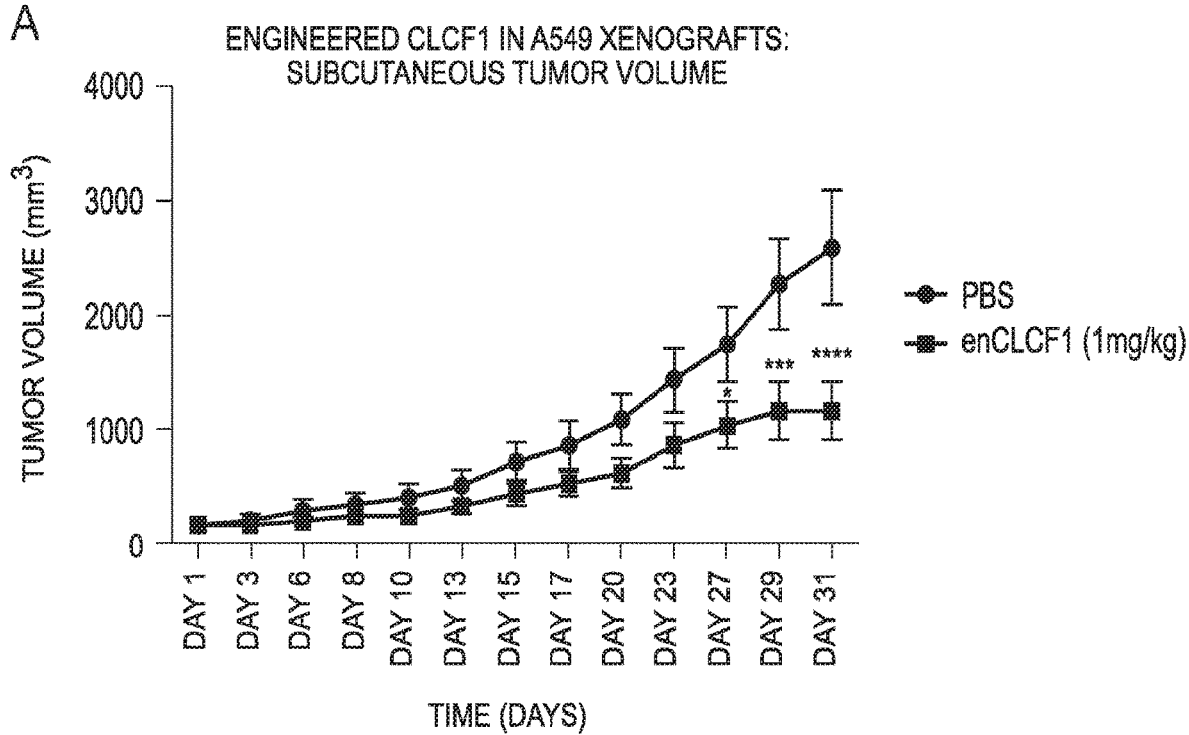
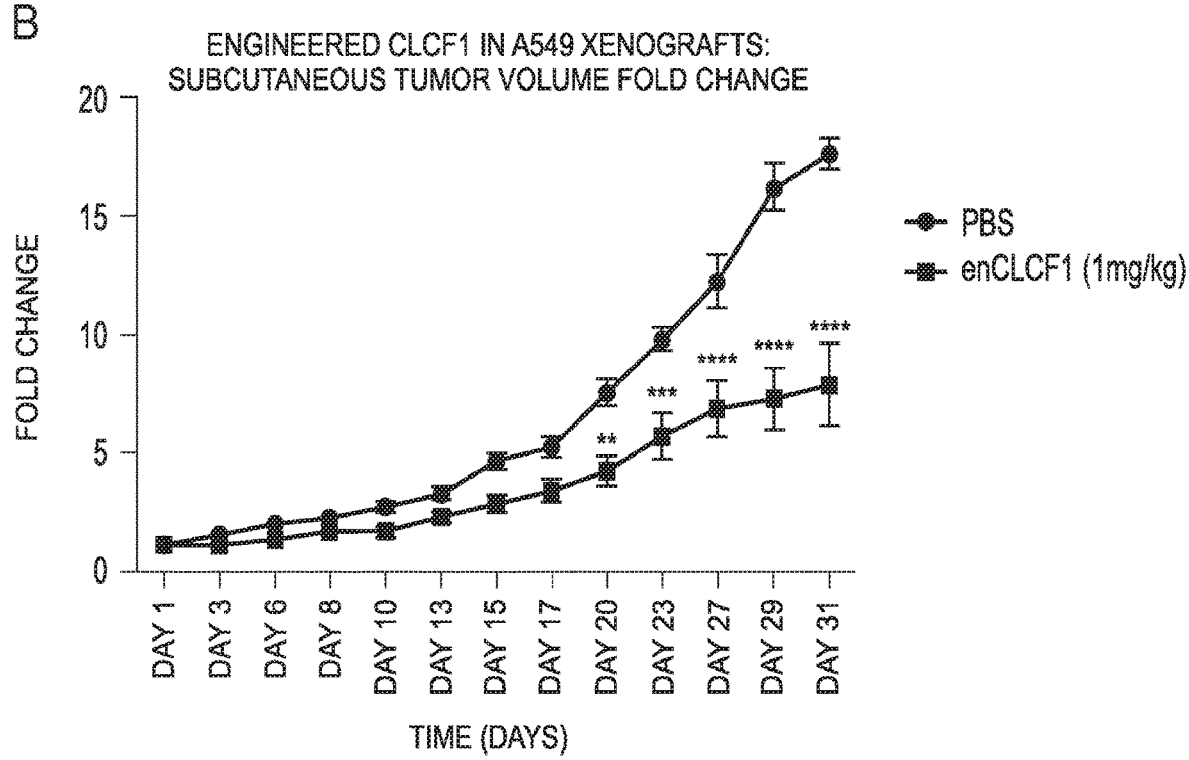

FIG. 24
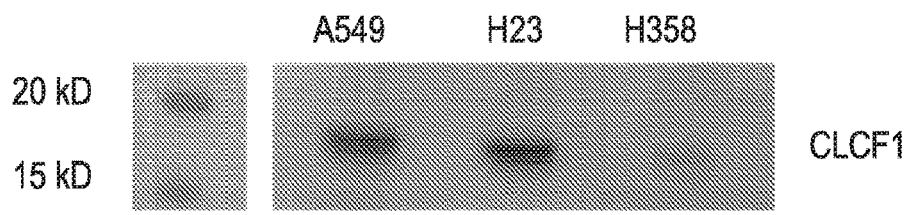
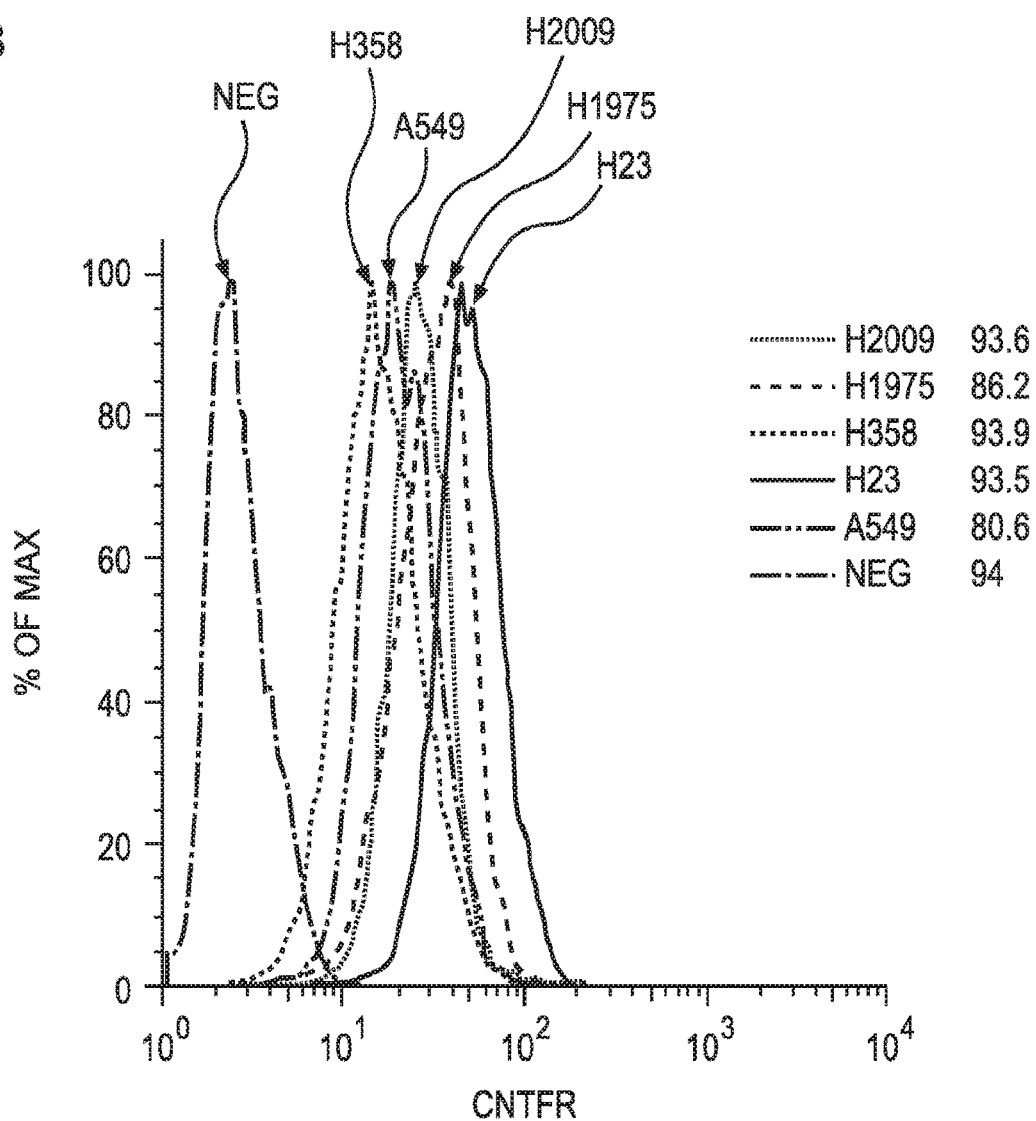

SEQUENCE LISTING

```
<160> NUMBER OF SEQ ID NOS: 7

<210> SEQ ID NO 1
<211> LENGTH: 372
<212> TYPE: PRT
<213> ORGANISM: Homo sapiens

<400> SEQUENCE: 1

Met Ala Ala Pro Val Pro Trp Ala Cys Cys Ala Val Leu Ala Ala Ala
1               5                   10                  15

Ala Ala Val Val Tyr Ala Gln Arg His Ser Pro Gln Glu Ala Pro His
                20                  25                  30

Val Gln Tyr Glu Arg Leu Gly Ser Asp Val Thr Leu Pro Cys Gly Thr
            35                  40                  45

Ala Asn Trp Asp Ala Ala Val Thr Trp Arg Val Asn Gly Thr Asp Leu
        50                  55                  60

Ala Pro Asp Leu Leu Asn Gly Ser Gln Leu Val Leu His Gly Leu Glu
65                  70                  75                  80

Leu Gly His Ser Gly Leu Tyr Ala Cys Phe His Arg Asp Ser Trp His
                85                  90                  95

Leu Arg His Gln Val Leu Leu His Val Gly Leu Pro Pro Arg Glu Pro
                100                 105                 110

Val Leu Ser Cys Arg Ser Asn Thr Tyr Pro Lys Gly Phe Tyr Cys Ser
            115                 120                 125

Trp His Leu Pro Thr Pro Thr Tyr Ile Pro Asn Thr Phe Asn Val Thr
        130                 135                 140

Val Leu His Gly Ser Lys Ile Met Val Cys Glu Lys Asp Pro Ala Leu
145                 150                 155                 160

Lys Asn Arg Cys His Ile Arg Tyr Met His Leu Phe Ser Thr Ile Lys
                165                 170                 175

Tyr Lys Val Ser Ile Ser Val Ser Asn Ala Leu Gly His Asn Ala Thr
            180                 185                 190

Ala Ile Thr Phe Asp Glu Phe Thr Ile Val Lys Pro Asp Pro Pro Glu
        195                 200                 205

Asn Val Val Ala Arg Pro Val Pro Ser Asn Pro Arg Arg Leu Glu Val
    210                 215                 220

Thr Trp Gln Thr Pro Ser Thr Trp Pro Asp Pro Glu Ser Phe Pro Leu
225                 230                 235                 240
```

-continued

Lys Phe Phe Leu Arg Tyr Arg Pro Leu Ile Leu Asp Gln Trp Gln His
              245                 250                 255

Val Glu Leu Ser Asp Gly Thr Ala His Thr Ile Thr Asp Ala Tyr Ala
        260                 265                 270

Gly Lys Glu Tyr Ile Ile Gln Val Ala Ala Lys Asp Asn Glu Ile Gly
            275                 280                 285

Thr Trp Ser Asp Trp Ser Val Ala Ala His Thr Pro Trp Thr Glu
        290                 295                 300

Glu Pro Arg His Leu Thr Glu Ala Gln Ala Glu Thr Thr Thr
305                 310                 315                 320

Ser Thr Thr Ser Ser Leu Ala Pro Pro Thr Thr Lys Ile Cys Asp
                325                 330                 335

Pro Gly Glu Leu Gly Ser Gly Gly Pro Ser Ala Pro Phe Leu Val
            340                 345                 350

Ser Val Pro Ile Thr Leu Ala Leu Ala Ala Ala Ala Thr Ala Ser
            355                 360                 365

Ser Leu Leu Ile
    370

<210> SEQ ID NO 2
<211> LENGTH: 200
<212> TYPE: PRT
<213> ORGANISM: Homo sapiens

<400> SEQUENCE: 2

Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
                20                  25                  30

Ala Leu Thr Glu Ser Tyr Val Lys His Gln Gly Leu Asn Lys Asn Ile
            35                  40                  45

Asn Leu Asp Ser Ala Asp Gly Met Pro Val Ala Ser Thr Asp Gln Trp
        50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200

<210> SEQ ID NO 3
<211> LENGTH: 225
<212> TYPE: PRT
<213> ORGANISM: Homo sapiens

<400> SEQUENCE: 3

```
Met Asp Leu Arg Ala Gly Asp Ser Trp Gly Met Leu Ala Cys Leu Cys
1               5                   10                  15

Thr Val Leu Trp His Leu Pro Ala Val Pro Ala Leu Asn Arg Thr Gly
            20                  25                  30

Asp Pro Gly Pro Gly Pro Ser Ile Gln Lys Thr Tyr Asp Leu Thr Arg
        35                  40                  45

Tyr Leu Glu His Gln Leu Arg Ser Leu Ala Gly Thr Tyr Leu Asn Tyr
    50                  55                  60

Leu Gly Pro Pro Phe Asn Glu Pro Asp Phe Asn Pro Pro Arg Leu Gly
65                  70                  75                  80

Ala Glu Thr Leu Pro Arg Ala Thr Val Asp Leu Glu Val Trp Arg Ser
                85                  90                  95

Leu Asn Asp Lys Leu Arg Leu Thr Gln Asn Tyr Glu Ala Tyr Ser His
            100                 105                 110

Leu Leu Cys Tyr Leu Arg Gly Leu Asn Arg Gln Ala Ala Thr Ala Glu
        115                 120                 125

Leu Arg Arg Ser Leu Ala His Phe Cys Thr Ser Leu Gln Gly Leu Leu
    130                 135                 140

Gly Ser Ile Ala Gly Val Met Ala Ala Leu Gly Tyr Pro Leu Pro Gln
145                 150                 155                 160

Pro Leu Pro Gly Thr Glu Pro Thr Trp Thr Pro Gly Pro Ala His Ser
                165                 170                 175

Asp Phe Leu Gln Lys Met Asp Asp Phe Trp Leu Leu Lys Glu Leu Gln
            180                 185                 190

Thr Trp Leu Trp Arg Ser Ala Lys Asp Phe Asn Arg Leu Lys Lys Lys
        195                 200                 205

Met Gln Pro Pro Ala Ala Ala Val Thr Leu His Leu Gly Ala His Gly
    210                 215                 220

Phe
225
```

<210> SEQ ID NO 4
<211> LENGTH: 204
<212> TYPE: PRT
<213> ORGANISM: Homo sapiens

<400> SEQUENCE: 4

```
Met Tyr Cys Leu Leu Ala Thr Pro Leu Cys Leu Leu Ser Leu Leu Leu
1               5                   10                  15

Pro Pro Leu Ser Pro Ala Ala Pro Ile Ser Pro Ser Glu Pro Ile Gly
            20                  25                  30

Gln Ala Tyr Ser Leu Ala Leu Tyr Met Gln Lys Asn Thr Ser Ala Leu
        35                  40                  45

Leu Gln Thr Tyr Leu Gln His Gln Gly Ser Pro Phe Ser Asp Pro Gly
    50                  55                  60

Phe Ser Ala Pro Glu Leu Gln Leu Ser Thr Leu Pro Ser Ala Ala Val
65                  70                  75                  80

Ser Phe Lys Thr Trp His Ala Met Glu Asp Ala Glu Arg Leu Ser Arg
                85                  90                  95

Ala Gln Gly Ala Phe Leu Ala Leu Thr Gln His Leu Gln Leu Val Gly
            100                 105                 110

Asp Asp Gln Ser Tyr Leu Asn Pro Gly Ser Pro Ile Leu Leu Ala Gln
        115                 120                 125
```

```
Leu Gly Ala Ala Arg Leu Arg Ala Gln Gly Leu Gly Asn Met Ala
        130                 135                 140

Ala Ile Met Thr Ala Leu Gly Leu Pro Ile Pro Glu Glu Asp Thr
145                 150                 155                 160

Leu Gly Phe Val Pro Phe Gly Ala Ser Ala Phe Glu Arg Lys Cys Arg
                165                 170                 175

Gly Tyr Ile Val Thr Arg Glu Tyr Gly His Trp Thr Asp Arg Ala Val
                180                 185                 190

Arg Asp Leu Ala Leu Leu Lys Ala Lys Tyr Ser Ala
        195                 200

<210> SEQ ID NO 5
<211> LENGTH: 198
<212> TYPE: PRT
<213> ORGANISM: Artificial Sequence
<220> FEATURE:
<223> OTHER INFORMATION: Synthetic sequence

<400> SEQUENCE: 5

Leu Asn Arg Thr Gly Asp Pro Gly Pro Gly Pro Ser Ile Gln Lys Thr
1               5                   10                  15

Tyr Asp Leu Thr Arg Tyr Leu Glu His Gln Leu Arg Ser Leu Ala Gly
                20                  25                  30

Thr Tyr Leu Asn Tyr Leu Gly Pro Pro Phe Asn Glu Pro Asp Phe Asn
            35                  40                  45

Pro Pro Arg Leu Gly Ala Glu Thr Leu Pro Arg Ala Thr Val Asp Leu
        50                  55                  60

Glu Val Trp Arg Ser Leu Asn Asp Lys Leu Arg Leu Thr Gln Asn Tyr
65              70                  75                  80

Glu Ala Tyr Ser His Phe Leu Cys Tyr Leu Arg Gly Leu Asn Arg Arg
                85                  90                  95

Ala Ala Thr Ala Glu Leu Arg Arg Ser Leu Ala His Phe Cys Thr Ser
            100                 105                 110

Leu Gln Gly Leu Leu Gly Ser Ile Ala Gly Val Met Ala Ala Leu Gly
        115                 120                 125

Tyr Pro Leu Pro Gln Pro Leu Pro Gly Thr Glu Pro Thr Trp Thr Pro
        130                 135                 140

Gly Pro Ala Arg Ser Asp Phe Leu Gln Lys Met Asp Asp Phe Trp Leu
145                 150                 155                 160

Leu Lys Glu Leu Gln Thr Trp Leu Trp Arg Ser Ala Lys Asp Phe Asn
                165                 170                 175

Arg Leu Lys Lys Lys Met Gln Pro Pro Ala Ala Ala Val Thr Leu His
            180                 185                 190

Leu Gly Ala His Gly Phe
        195

<210> SEQ ID NO 6
<211> LENGTH: 198
<212> TYPE: PRT
<213> ORGANISM: Artificial Sequence
<220> FEATURE:
<223> OTHER INFORMATION: Synthetic sequence

<400> SEQUENCE: 6

Leu Asn Arg Thr Gly Asp Pro Gly Pro Gly Pro Ser Ile Gln Lys Thr
1               5                   10                  15

Tyr Asp Leu Thr Arg Cys Leu Glu His Gln Leu Arg Ser Leu Ala Gly
```

```
                    20                  25                  30
Thr Tyr Leu Asn Tyr Leu Gly Pro Pro Phe Asn Glu Pro Asp Phe Asn
                35                  40                  45
Pro Pro Arg Leu Gly Ala Glu Thr Leu Pro Arg Ala Thr Val Asp Leu
         50                  55                  60
Glu Val Trp Arg Ser Leu Asn Asp Lys Leu Arg Leu Thr Gln Asn Tyr
 65                  70                  75                  80
Glu Ala Tyr Ser His Phe Leu Cys Tyr Leu Arg Gly Leu Asn Arg Arg
                 85                  90                  95
Ala Ala Thr Ala Glu Leu Arg Arg Ser Leu Ala His Phe Cys Thr Ser
            100                 105                 110
Leu Gln Gly Leu Leu Gly Ser Ile Ala Gly Val Met Ala Ala Leu Gly
        115                 120                 125
Tyr Pro Leu Pro Gln Pro Leu Pro Gly Thr Glu Pro Thr Trp Thr Pro
    130                 135                 140
Gly Pro Ala Arg Ser Asp Ala Leu Gln Ala Met Asp Asp Phe Trp Leu
145                 150                 155                 160
Leu Lys Glu Leu Gln Thr Trp Leu Leu Arg Ser Ala Lys Asp Phe Asn
                165                 170                 175
Arg Leu Lys Arg Lys Met Gln Pro Pro Ala Ala Ala Val Thr Leu His
            180                 185                 190
Leu Gly Ala His Gly Phe
        195

<210> SEQ ID NO 7
<211> LENGTH: 227
<212> TYPE: PRT
<213> ORGANISM: Homo sapiens

<400> SEQUENCE: 7

Asp Lys Thr His Thr Cys Pro Pro Cys Pro Ala Pro Glu Leu Leu Gly
 1               5                  10                  15
Gly Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
            35                  40                  45
Glu Asp Pro Glu Val Lys Phe Asn Trp Tyr Val Asp Gly Val Glu Val
        50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
```

```
Asp Lys Ser Arg Trp Gln Gln Gly Asn Val Phe Ser Cys Ser Val Met
    195                 200                 205
His Glu Ala Leu His Asn His Tyr Thr Gln Lys Ser Leu Ser Leu Ser
    210                 215                 220
Pro Gly Lys
225
```

CILIARY NEUROTROPHIC FACTOR RECEPTOR LIGANDS AND METHODS OF USING THE SAME

CROSS-REFERENCE TO RELATED APPLICATIONS

This application claims the benefit of U.S. Provisional Patent Application No. 62/443,554, filed Jan. 6, 2017, and U.S. Provisional Patent Application No. 62/515,746, filed Jun. 6, 2017, which applications are incorporated herein by reference in their entirety.

INTRODUCTION

Ciliary neurotrophic factor (CNTF) was identified as a survival factor for chick ciliary neurons and belongs to the interleukin (IL)-6 family of structurally related hemato- and neuropoietic cytokines (IL-6, IL-11, cardiotrophin-like cytokine factor 1 (CLCF1), leukemia inhibitory factor (LIF), oncostatin M (OSM), cardiotrophin-1 (CT-1)). Cellular responses to CNTF and IL-6 type cytokines are elicited by different multi-unit receptor complexes that include the membrane-spanning 130-kDa glycoprotein, gp130. CNTF first binds in a 1:1 stoichiometry to the GPI-anchored CNTF receptor (CNTFR), which is not involved in signal transduction. Binding of CNTF to the membrane-bound or soluble CNTFR induces a heterodimer of the signal transducing β-receptors gp130 and LIF receptor (LIFR), which triggers intracellular signaling cascades.

Cancer is initiated and progresses within a microenvironment that is itself altered as a consequence of the tumorigenic process. Stromal cells in contact with cancer cells secrete growth factors and cytokines that may act directly by signaling to tumor cells or indirectly by recruiting other stromal components to promote tumor progression. An important aspect of this process is the expansion of cancer-associated fibroblasts (CAFs). CAFs are a diverse population of stromal cells with distinct characteristics in different tumors and tissues.

CAFs support the growth of cancer cells (e.g., lung cancer cells) in vivo by secretion of soluble factors that stimulate the growth of tumor cells. One such soluble factor is CLCF1. CLCF1 produced by cells in the stroma is received as a growth signal by tumor cells expressing a receptor for this protein—CNTFR. For example, functional studies have identified a role for CLCF1-CNTFR signaling in promoting growth of non-small cell lung cancer (NSCLC).

Studies have also shown that CNTFR and its cognate ligands support the survival of neurons. For example, CNTF has been shown to have a direct neuroprotective effect on degenerating motoneurons in stress-induced conditions, both in cell culture and in a rodent model of axotomy-induced apoptosis. The beneficial effect of CNTF was further supported in a mouse model of neuronopathy with motoneuron degeneration. Given these promising results, CNTF was tested in two clinical trials in 1996 with 570 and 730 patients. However, both trials reported no observable benefit of treatment, with severe adverse effects for doses over 5 µg/kg. Two main reasons appeared to account for failure in these trials. First, the half-life of CNTF after intravenous injection is only ~3 min, so subcutaneously applied CNTF was unlikely to have adequately reached its target cells. Second, further research found that CNTF has another binding partner, interleukin-6 receptor (IL6R), which induces an acute-phase response on human liver cells. Attempts have been made to create CNTF variants with reduced IL6R binding affinity, but these variants suffered from weak CNTFR binding, and hence limited potency.

SUMMARY

Provided are ciliary neurotrophic factor receptor (CNTFR) ligands. In certain aspects, a CNTFR ligand of the present disclosure exhibits increased affinity for CNTFR relative to the corresponding wild-type CNTFR ligand. In certain aspects, a CNTFR ligand of the present disclosure results in reduced binding affinity of glycoprotein 130 (gp130), leukemia inhibitory factor receptor (LIFR), or both, for a complex including the CNTFR ligand and CNTFR, relative to the binding affinity for a complex including the corresponding wild-type CNTFR ligand and CNTFR. In certain aspects, a CNTFR ligand of the present disclosure has both of the aforementioned properties. Also provided are pharmaceutical compositions including the CNTFR ligands, as well as methods of using the CNTFR ligands.

BRIEF DESCRIPTION OF THE FIGURES

FIG. 4, panels A and B, shows the effect of CLCF1 treatment on SH-SY5Y and E18 cells. After 24 h of pre-incubation in serum free condition, cells were treated with CLCF1 in serum free media for 72 h. CLCF1 increased SH-SY5Y (panel A) and E18 (panel B) cell survival in a concentration-dependent manner. Statistical significance was measured against the negative control *P<0.05, **P<0.01.

FIG. 6 depicts the amino acid sequences for colonies isolated from the highest CNTFR binding population after 3 rounds of screening of a randomly mutated yeast-displayed CLCF1 library.

FIG. 10, panels A and B, shows data demonstrating that FRR-CLCF1 enhances cell survival in SH-SY5Y (panel A) and E18 (panel B) cells. Significance was measured against wtCLCF1-treated sample at the same concentration. *P<0.05, **P<0.01.

FIG. 14 depicts the amino acid sequences for colonies isolated from the highest affinity population after 3 rounds of sorting with shuffled CLCF1 library.

FIG. 18, panels A and B, show data demonstrating that CLCF1 constructs with Y22C, W169L, and K180R exhibit decreased binding to gp130 (panel A) while LIFR binding increased (panel B). Significance was measured against wtCLCF1. *P<0.05, **P<0.01.

FIG. 22, panels A and B, provides data demonstrating that enCLCF1 inhibits cell survival enhancing effect of wtCLCF1 in A549 (panel A) and H23 (panel B). Significance was measured against non-treated control. *P<0.05, **P<0.01.

FIG. 23, panels A and B, provides data demonstrating that enCLCF1 treatment inhibits in vivo growth of A549 xenograft model. Tumor burden in in vivo model of NSCLC using A549 in tumor volume (panel A), and fold change of the individual tumors from day 1 (panel B). Significance was measured against PBS treated control. *P<0.05, P<0.01, *P<0.001, ****P<0.0001.

DETAILED DESCRIPTION

Figure 1:
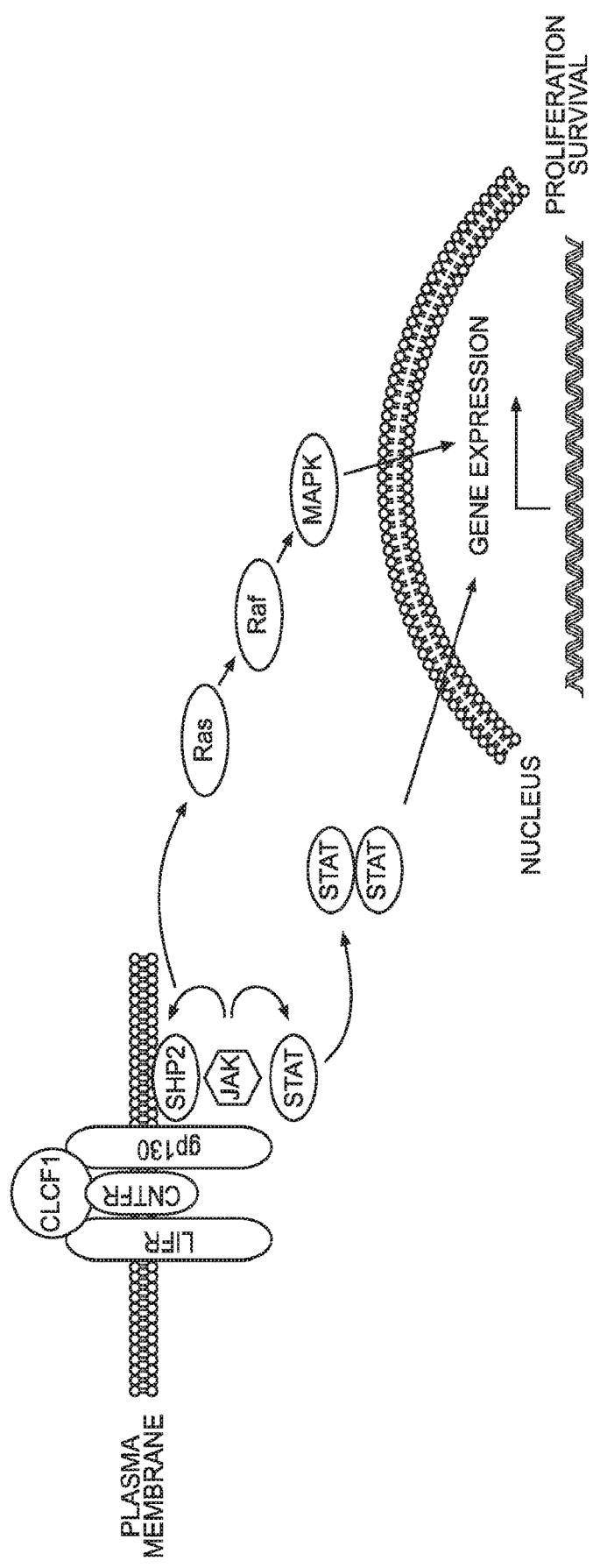
FIG. 1 schematically illustrates activation of the CNTFR signaling pathway by wild-type CLCF1.

Provided are ciliary neurotrophic factor receptor (CNTFR) ligands. In certain aspects, a CNTFR ligand of the present disclosure exhibits increased affinity for CNTFR relative to the corresponding wild-type CNTFR ligand. In certain aspects, a CNTFR ligand of the present disclosure results in reduced binding affinity of glycoprotein 130 (gp130), leukemia inhibitory factor receptor (LIFR), or both, for a complex including the CNTFR ligand and CNTFR, relative to the binding affinity for a complex including the corresponding wild-type CNTFR ligand and CNTFR. In certain aspects, a CNTFR ligand of the present disclosure has both of the aforementioned properties. Also provided are pharmaceutical compositions including the CNTFR ligands, as well as methods of using the CNTFR ligands.

Before the CNTFR ligands, compositions and methods of the present disclosure are described in greater detail, it is to be understood that the ligands, compositions and methods are not limited to particular embodiments described, as such may, of course, vary. It is also to be understood that the terminology used herein is for the purpose of describing particular embodiments only, and is not intended to be limiting, since the scope of the ligands, compositions and methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the ligands, compositions and methods. The upper and lower limits of these smaller ranges may independently be included in the smaller ranges and are also encompassed within the ligands, compositions and methods, subject to any specifically excluded limit in the stated range. Where the stated range includes one or both of the limits, ranges excluding either or both of those included limits are also included in the ligands, compositions and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the ligands, compositions and methods belong. Although any ligands, compositions and methods similar or equivalent to those described herein can also be used in the practice or testing of the ligands, compositions and methods, representative illustrative ligands, compositions and methods are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present ligands, compositions and methods are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the ligands, compositions and methods, which are, for clarity, described in the context of separate embodiments, may also be provided in combination in a single embodiment. Conversely, various features of the ligands, compositions and methods, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present ligands, compositions and methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

CNTFR Ligands

As summarized above, aspects of the present disclosure include ciliary neurotrophic factor receptor (CNTFR) ligands. CNTFR (also referred to as CNTF receptor subunit a) is a member of the type 1 cytokine receptor family. CNTFR is the ligand-specific component of a tripartite receptor for ciliary neurotrophic factor (CNTF), as well as other ligands such as cardiotrophin-like cytokine factor 1 (CLCF1) and neuropoetin (NP). Binding of wild-type ligand to CNTFR recruits the transmembrane components of the receptor, gp130 and leukemia inhibitory factor receptor (LIFR), facilitating signal transduction. Wild-type amino acid sequences for human CNTFR, CNTF, CLCF1 and NP are provided in Table 1.

TABLE 1

Wild-Type Human CNTFR and CNTFR Ligand Amino Acid Sequences

| | Amino Acid Sequence |
|---|---|
| Wild-Type Human CNTFR (SEQ ID NO: 1) | MAAPVPWACCAVLAAAAAVVYAQRHSPQEAPHVQYERLGSDVTLPCGTA NWDAAVTWRVNGTDLAPDLLNGSQLVLHGLELGHSGLYACFHRDSWHLR HQVLLHVGLPPREPVLSCRSNTYPKGFYCSWHLPTPTYIPNTFNVTVLH GSKIMVCEKDPALKNRCHIRYMHLFSTIKYKVSISVSNALGHNATAITF DEFTIVKPDPPENVVARPVPSNPRRLEVTWQTPSTWPDPESFPLKFFLR YRPLILDQWQHVELSDGTAHTITDAYAGKEYIIQVAAKDNEIGTWSDWS VAAHATPWTEEPRHLTTEAQAAETTTSTTSSLAPPPTTKICDPGELGSG GGPSAPFLVSVPITLALAAAAATASSLLI |
| Wild-Type Human CNTF (SEQ ID NO: 2) | MAFTEHSPLTPHRRDLCSRSIWLARKIRSDLTALTESYVKHQGLNKNIN LDSADGMPVASTDQWSELTEAERLQENLQAYRTFHVLLARLLEDQQVHF TPTEGDFHQAIHTLLLQVAAFAYQIEELMILLEYKIPRNEADGMPINVG DGGLFEKKLWGLKVLQELSQWTVRSIHDLRFISSHQTGIPARGSHYIAN NKKM |
| Wild-Type Human CLCF1 (SEQ ID NO: 3) | MDLRAGDSWGMLACLCTVLWHLPAVPALNRTGDPGPGPSIQKTYDLTRY LEHQLRSLAGTYLNYLGPPFNEPDFNPPRLGAETLPRATVDLEVWRSLN DKLRLTQNYEAYSHLLCYLRGLNRQAATAELRRSLAHFCTSLQGLLGSI AGVMAALGYPLPQPLPGTEPTWTPGPAHSDFLQKMDDFWLLKELQTWLW RSAKDFNRLKKKMQPPAAAVTLHLGAHGF |
| Wild-Type Human NP (SEQ ID NO: 4) | MYCLLATPLCLLSLLLPPLSPAAPISPSEPIGQAYSLALYMQKNTSALL QTYLQHQGSPFSDPGFSAPELQLSTLPSAAVSFKTWHAMEDAERLSRAQ GAFLALTQHLQLVGDDQSYLNPGSPILLAQLGAARLRAQGLLGNMAAIM TALGLPIPPEEDTLGFVPFGASAFERKCRGYIVTREYGHWTDRAVRDLA LLKAKYSA |

As used herein, a "CNTFR ligand" is a polypeptide that binds to CNTFR and is a variant of a wild-type CNTFR ligand, such as a variant CNTF ligand, a variant CLCF1 ligand, or a variant NP ligand. By "variant" is meant the CNTFR ligand includes one or more mutations relative to the corresponding wild-type CNTFR ligand. For example, a CNTF ligand of the present disclosure (which may be referred to as a "variant CNTF" or an "engineered CNTF") includes one or more mutations relative to wild-type CNTF, a CLCF1 ligand of the present disclosure (which may be referred to as a "variant CLCF1" or an "engineered CLCF1") includes one or more mutations relative to wild-type CLCF1, etc. As used throughout the present disclosure, a "mutation" or "mutations" may include one or more amino acid substitutions, one or more amino acid deletions (e.g., truncations), one or more amino acid insertions, or any combination thereof, in the CNTFR ligand relative to the corresponding wild-type CNTFR ligand.

In certain aspects, a CNTFR ligand of the present disclosure includes 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more mutations (e.g., amino acid substitution(s)), relative to the corresponding wild-type CNTFR ligand. In some embodiments, a CNTFR ligand of the present disclosure includes 20 or less, 19 or less, 18 or less, 17 or less, 16 or less, 15 or less, 14 or less, 13 or less, 12 or less, 11 or less, 10 or less, 9 or less, 8 or less, 7 or less, 6 or less, 5 or less, 4 or less, 3 or less, 2, or 1 mutation (e.g., amino acid substitution(s)), relative to the corresponding wild-type CNTFR ligand.

According to certain embodiments, a CNTFR ligand of the present disclosure includes an amino acid sequence that has 70% or greater, 75% or greater, 80% or greater, 85% or greater, 90% or greater, 95% or greater, or 99% or greater identity to the corresponding wild-type CNTFR ligand, or a fragment thereof, such as a CNTFR ligand fragment having a length of from 100-120 amino acids, 120-140 amino acids, 140-160 amino acids, 160-180 amino acids, 180-200 amino acids, or 200-220 amino acids.

In certain aspects, a CNTFR ligand of the present disclosure binds to CNTFR with a $K_D$ of less than or equal to about $10^{-5}$ M, less than or equal to about $10^{-6}$ M, less than or equal to about $10^{-7}$ M, less than or equal to about $10^{-8}$ M, or less than or equal to about $10^{-9}$ M, $10^{-10}$ M, $10^{-11}$ M, or $10^{-12}$ M or less. Such affinities may be readily determined using conventional techniques, such as by equilibrium dialysis; by using surface plasmon resonance (SPR) technology (e.g., the BIAcore 2000 instrument, using general procedures outlined by the manufacturer); by radioimmunoassay; or by another method set forth in the examples below or known to the skilled artisan.

In certain embodiments, a CNTFR ligand of the present disclosure exhibits increased binding affinity for CNTFR relative to the corresponding wild-type CNTFR ligand. By "increased binding affinity" or "greater binding affinity" is meant that the CNTFR ligand exhibits tighter binding (as indicated by a lower $K_D$ value) to CNTFR as compared to the corresponding wild-type CNTFR ligand. By way of example, in certain aspects, when the CNTFR ligand is a variant CLCF1 ligand, the binding affinity of the CLCF1 ligand for CNTFR has a $K_D$ value that is 20 nM or less.

In certain aspects, the CNTFR ligand that exhibits increased binding affinity for CNTFR relative to the corresponding wild-type CNTFR ligand is a CLCF1 ligand (which may be referred to as a "variant CLCF1" or an "engineered CLCF1"). In some embodiments, such a CLCF1 ligand may include one or more mutations at amino acid positions 86, 96, 148, 169, 180, or any combination thereof, relative to a CLCF1 ligand having the amino acid sequence set forth in SEQ ID NO:3. By way of example, such a CLCF1 ligand may include one or more mutations selected from L86F, Q96R, H148R, W169L, K180R, and any combination thereof, relative to a CLCF1 ligand having the amino acid sequence set forth in SEQ ID NO:3. Non-limiting examples of CLCF1 variants exhibiting increased binding affinity for CNTFR, as well as strategies for identifying additional such variants, are described in the Experimental section below.

In some embodiments, a CNTFR ligand of the present disclosure results in reduced binding affinity of glycoprotein 130 (gp130), leukemia inhibitory factor receptor (LIFR), or both, for a complex including the CNTFR ligand and CNTFR, relative to the binding affinity for a complex including the corresponding wild-type CNTFR ligand and CNTFR. As used herein, "reduced binding affinity", "decreased binding affinity", or "lower binding affinity" means that gp130, LIFR, or gp130 and LIFR, exhibits less tight binding (as indicated by a higher $K_D$ value) to a complex including the CNTFR ligand and CNTFR, as compared to a complex including the corresponding wild-type CNTFR ligand and CNTFR. The complex may consist of the CNTFR ligand bound to CNTFR, or may include additional components. For example, the CNTFR ligand may result in reduced binding affinity of gp130 for a complex consisting of the CNTFR ligand bound to CNTFR, or such a complex that further includes LIFR. Similarly, the CNTFR ligand may result in reduced binding affinity of LIFR for a complex consisting of the CNTFR ligand bound to CNTFR, or such a complex that further includes gp130.

In certain aspects, a CNTFR ligand of the present disclosure results in reduced binding affinity of gp130 for a complex comprising the CNTFR ligand and CNTFR. In some embodiments, such a ligand is a CLCF1 ligand that includes one or more mutations at amino acid positions 22, 169, 180, or any combination thereof, relative to a CLCF1 ligand having the amino acid sequence set forth in SEQ ID NO:3. By way of example, such a CLCF1 ligand may include one or more mutations selected from Y22C, W169L, K180R, and any combination thereof, relative to a CLCF1 ligand having the amino acid sequence set forth in SEQ ID NO:3. Non-limiting examples of CLCF1 variants resulting in reduced binding affinity of gp130 for a complex including the CLCF1 variant and CNTFR, as well as strategies for identifying additional such variants, are described in the Experimental section below.

According to certain embodiments, a CNTFR ligand of the present disclosure results in reduced binding affinity of LIFR for a complex comprising the CNTFR ligand and CNTFR. In certain aspects, such a ligand is a CLCF1 ligand that includes one or more mutations at amino acid positions 151, 154, or both, relative to a CLCF1 ligand having the amino acid sequence set forth in SEQ ID NO:3. By way of example, such a CLCF1 ligand may include one or more mutations selected from the group consisting of: F151A, K154A, or both, relative to a CLCF1 ligand having the amino acid sequence set forth in SEQ ID NO:3. Non-limiting examples of CLCF1 variants resulting in reduced binding affinity of LIFR for a complex including the CLCF1 variant and CNTFR, as well as strategies for identifying additional such variants, are described in the Experimental section below.

In certain aspects, a CNTFR ligand of the present disclosure exhibits increased binding affinity for CNTFR relative to the corresponding wild-type CNTFR ligand and results in reduced binding affinity of gp130, LIFR, or both, for a complex comprising the CNTFR ligand and CNTFR.

Methods are available for measuring the binding affinity of a CNTFR ligand to CNTFR, or for measuring the binding affinity of gp130 or LIFR for a complex that includes the CNTFR ligand and CNTFR. For example, surface plasmon resonance (SPR) technology (e.g., using a BIAcore™ 2000 instrument), KinExA® kinetic exclusion assay (Sapidyne Instruments), Bio-Layer Interferometry (BLI) technology (e.g., ForteBio Octet®), or other similar assay/technology may be employed to determine whether a CNTFR ligand exhibits a desired binding affinity. Suitable approaches for measuring binding affinity in the context of the present disclosure include, e.g., those described in Hunter, S. A. and Cochran, J. R. (2016) Methods Enzymol. 580:21-44.

In some embodiments, in a direct binding assay, an equilibrium binding constant ($K_D$) may be measured using a CNTFR ligand, gp130, or LIFR conjugated to a fluorophore or radioisotope, or a CNTFR ligand, gp130, or LIFR that contains an N- or C-terminal epitope tag for detection by a labeled antibody. If labels or tags are not feasible or desired, a competition binding assay can be used to determine the half-maximal inhibitory concentration ($IC_{50}$), the amount of unlabeled CNTFR ligand, gp130, or LIFR at which 50% of the maximal signal of the labeled competitor is detectable. A $K_D$ value can then be calculated from the measured $IC_{50}$ value.

The amino acid sequences of two non-limiting examples of CNTFR ligands of the present disclosure are provided in Table 2 below.

TABLE 2

Amino Acid Sequences of Two Example CNTFR Ligands

| | Amino Acid Sequence |
|---|---|
| Example CNTFR Ligand (CLCF1 variant-"FRR-CLCF1") (SEQ ID NO: 5) (L86F, Q96R, H148R) | LNRTGDPGPGPSIQKTYDLTRYLEHQLRSLAGTYLNYL GPPFNEPDFNPPRLGAETLPRATVDLEVWRSLNDKLRL TQNYEAYSH<u>F</u>LCYLRGLNR<u>R</u>AATAELRRSLAHFCTSLQ GLLGSIAGVMAALGYPLPQPLPGTEPTWTPGPA<u>R</u>SDFL QKMDDFWLLKELQTWLWRSAKDFNRLKKKMQPPAAAVT LHLGAHGF |
| Example CNTFR Ligand (CLCF1 variant-"enCLCF1") (SEQ ID NO: 6) (Y22C, L86F, Q96R, H148R, F151A, K154A, W169L, K180R) | LNRTGDPGPGPSIQKTYDLTR<u>C</u>LEHQLRSLAGTYLNYL GPPFNEPDFNPPRLGAETLPRATVDLEVWRSLNDKLRL TQNYEAYSH<u>F</u>LCYLRGLNR<u>R</u>AATAELRRSLAHFCTSLQ GLLGSIAGVMAALGYPLPQPLPGTEPTWTPGPA<u>R</u>SD<u>A</u>L <u>Q</u>AMDDFWLLKELQTWL<u>L</u>RSAKDFNRLK<u>R</u>KMQPPKAAVT LHLGAHGF |

The example CNTFR ligands in Table 2 are CLCF1 variants. Both variants exhibit increased binding affinity for CNTFR relative to wild-type CLCF1. See Example 1 below. The second variant additionally results in reduced binding affinity of gp130 and LIFR to a complex that includes this variant and CNTFR. See Example 2 below.

Figure 15:
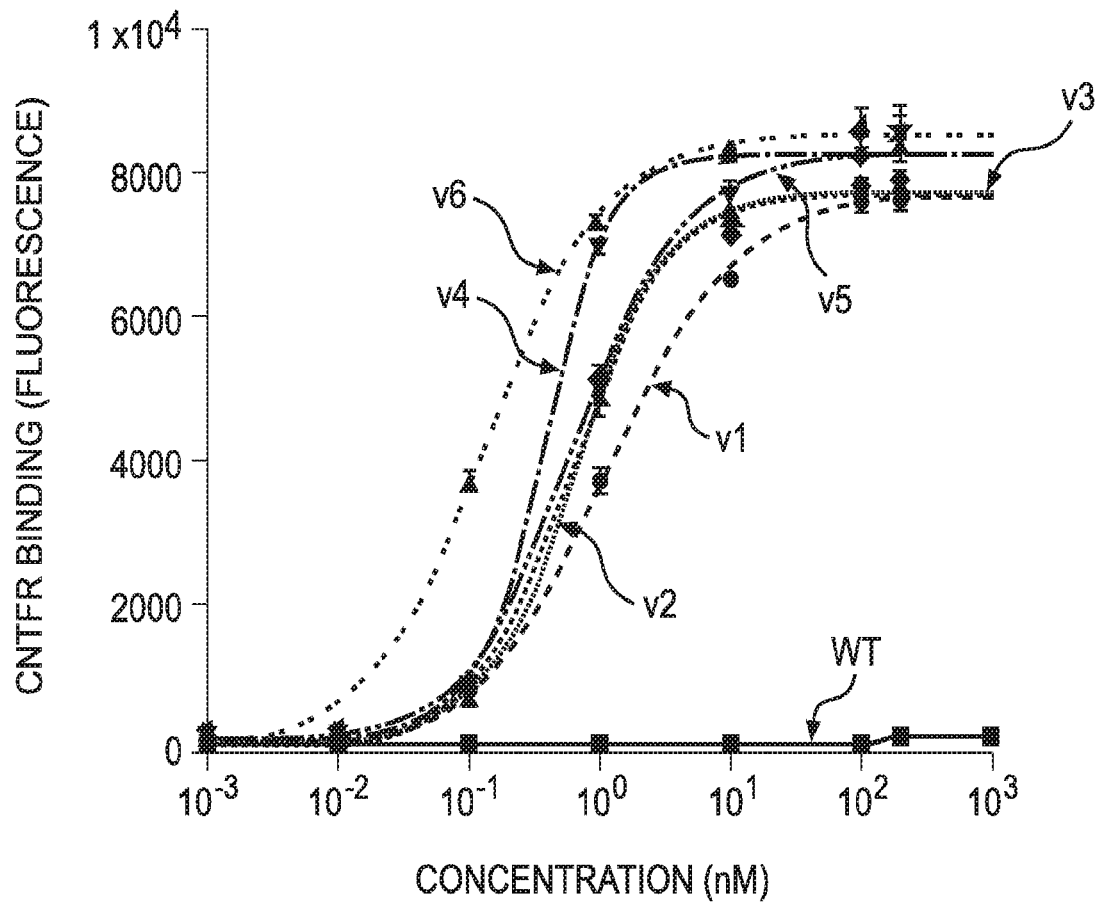
FIG. 15, panels A and B, shows data relating to the characterization of affinity matured CLCF1 variants. Panel A: Soluble CNTFR binding to yeasts expressing CLCF1 constructs isolated from affinity maturation. Panel B: Apparent $K_d$ values of yeast displayed CLCF1 constructs.
Figures 19, 20:
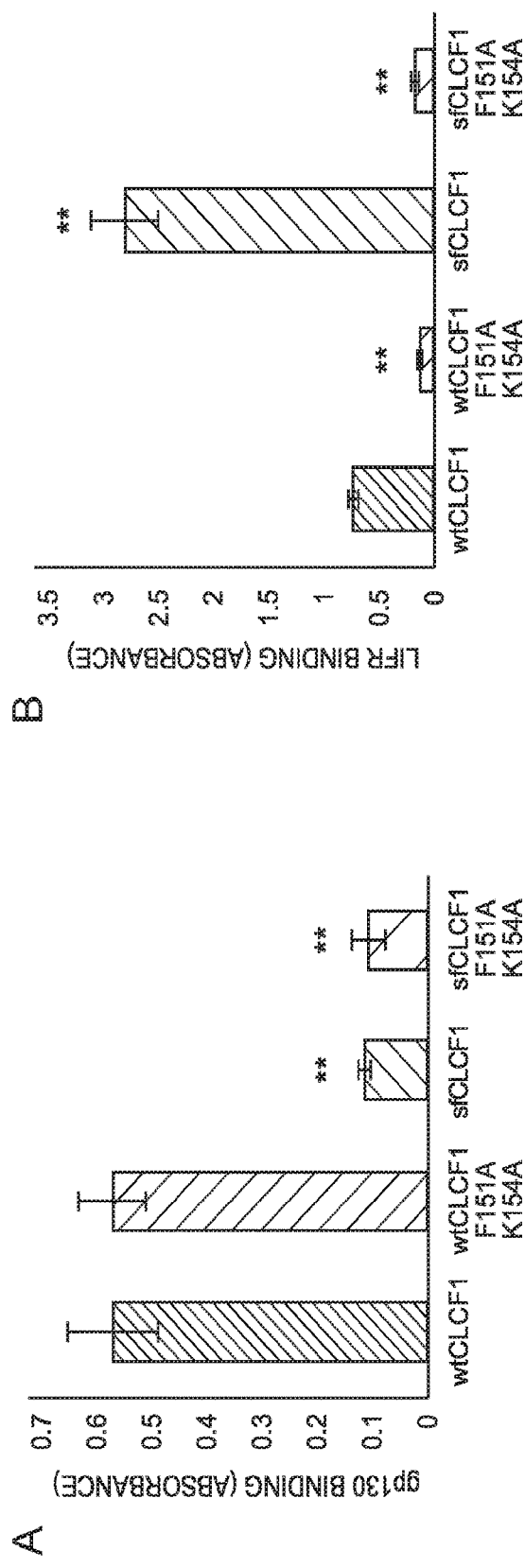
FIG. 19, panels A and B, shows data demonstrating that F151A and K154A in CLCF1 does not influence gp130 binding (panel A) while they decrease binding to LIFR (panel B). Significance was measured against wtCLCF1. *P<0.05, **P<0.01.
FIG. 20 shows engineered CLCF1 variants with different binding specificities for the beta receptors.
Figure 21:
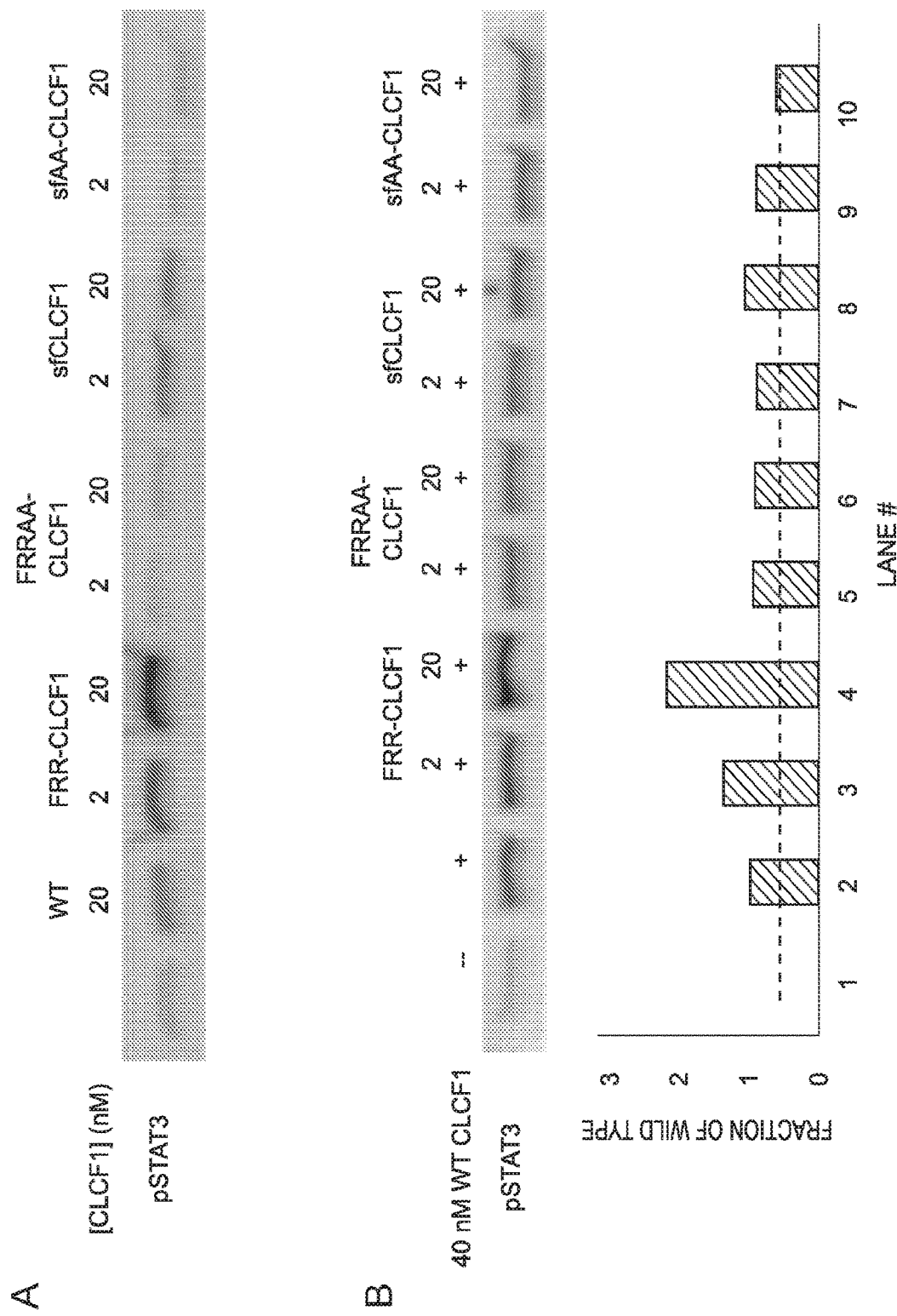
FIG. 21, panels A and B, provides data demonstrating that CLCF1 constructs that bind to CNTFR with high affinity and different beta receptor binding affinities activate STAT3 differently. Panel A: Phosphorylation of STAT3 (705) induced by different CLCF1 variants. Panel B: Phosphorylation of STAT3 when wtCLCF1 is combined with different CLCF1 variants.

In some embodiments, a CNTFR ligand of the present disclosure is any of the CNTFR ligands presented in Table 2, the Experimental section below, and any of FIGS. 6-8, FIG. 14. FIG. 15, and FIG. 20. In some embodiments, such a CNTFR ligand is present in a fusion protein (e.g., fused to an Fc domain), conjugate (e.g., conjugated to PEG, a drug, and/or the like), or combination thereof, as described elsewhere herein.

In certain aspects, a CNTFR ligand of the present disclosure binds to CNTFR and has 70% or greater, 75% or greater, 80% or greater, 85% or greater, 90% or greater, 95% or greater, or 99% or greater amino acid sequence identity to any of the CNTFR ligands presented in Table 2, the Experimental section below, and any of FIGS. 6-8, FIG. 14. FIG. 15, and FIG. 20. In some embodiments, such a CNTFR ligand is present in a fusion protein (e.g., fused to an Fc domain), conjugate (e.g., conjugated to PEG, a drug, and/or the like), or combination thereof, as described elsewhere herein.

In certain aspects, a CNTFR ligand of the present disclosure is a CLCF1 variant that binds to CNTFR and includes an amino acid substitution selected from L86F, Q96R, H148R, and any combination thereof, where the CLCF1 variant includes 70% or greater, 75% or greater, 80% or greater, 85% or greater, 90% or greater, 95% or greater, or 99% or greater amino acid sequence identity to the amino acid sequence set forth in SEQ ID NO:5 ("FRR-CLCF1"). In some embodiments, such a CNTFR ligand is present in a fusion protein (e.g., fused to an Fc domain), conjugate (e.g., conjugated to PEG, a drug, and/or the like), or combination thereof, as described elsewhere herein.

In certain aspects, a CNTFR ligand of the present disclosure is a CLCF1 variant that binds to CNTFR and includes an amino acid substitution selected from Y22C, L86F, Q96R, H148R, F151A, K154A, W169L, K180R, and any combination thereof, where the CLCF1 variant includes 70% or greater, 75% or greater, 80% or greater, 85% or greater, 90% or greater, 95% or greater, or 99% or greater amino acid sequence identity to the amino acid sequence set forth in SEQ ID NO:6 ("enCLCF1"). In some embodiments, such a CNTFR ligand is present in a fusion protein (e.g., Engineering/Development and Production of CNTFR Ligands Also provided by the present disclosure are methods of engineering/developing additional CNTFR ligands having one or more desired functionalities. The manner in which the CNTFR ligands are developed may vary. Rational and combinatorial approaches may be used to engineer CNTFR ligands with novel properties, e.g., increased binding affinity for CNTFR relative to the corresponding wild-type CNTFR ligand, reduced binding affinity of gp130, LIFR, or both, for a complex including the CNTFR ligand and CNTFR, any combination thereof, etc. For example, to develop a CNTFR ligand, a library of CNTFR ligands (e.g., variant CNTFs, variant CLCF1s, variant NPs, etc.) may be created and screened, e.g., by bacterial display, phage display, yeast surface display, fluorescence-activated cell sorting (FACS), and/or any other suitable screening method.

Yeast surface display is a powerful combinatorial technology that has been used to engineer proteins with novel molecular recognition properties, increased target binding affinity, proper folding, and improved stability. In this platform, libraries of protein variants are generated and screened in a high-throughput manner to isolate mutants with desired biochemical and biophysical properties. As demonstrated in the Examples section below, the present inventors have successfully employed yeast surface display for engineering CNTFR ligands with increased binding affinities for CNTFR, as well as CNTFR ligands that result in reduced binding affinities of gp130 and LIFR for a complex including the CNTFR ligand and CNTFR. Yeast surface display benefits from quality control mechanisms of the eukaryotic secretory pathway, chaperone-assisted folding, and efficient disulfide bond formation.

One example approach for developing a CNTFR ligand having a desirable property of interest involves genetically fusing a CNTFR ligand to the yeast mating agglutinin protein Aga2p, which is attached by two disulfide binds to the yeast cell wall protein Aga1p. This Aga2p-fusion construct, and a chromosomally integrated Aga1p expression cassette, may be expressed under the control of a suitable promoter, such as a galactose-inducible promoter. N- or C-terminal epitope tags may be included to measure cell surface expression levels by flow cytometry using fluorescently labeled primary or secondary antibodies. This construct represents the most widely used display format, where a terminus of the CNTFR ligand (or other protein to be engineered) is fused to Aga2p, but several alternative variations of the yeast surface display plasmid have been described and may be employed to develop a CNTFR ligand of the present disclosure. One of the benefits of this screening platform over panning-based methods used with phage or mRNA display is that two-color FACS can be used to quantitatively discriminate clones that differ by as little as two-fold in binding affinity to a particular target.

To selectively mutate CNTFR ligands at the DNA level, an example approach is error prone PCR, which can be used to introduce mutations by any number of altered reaction conditions including using a polymerase that does not possess proofreading (i.e. exonuclease) activity, using mixtures of triphosphate derivatives of nucleoside analogues, using altered ratios of dNTPs, varying concentrations of magnesium or manganese, or the like. Alternatively, degenerate codons can be introduced by oligonucleotide assembly using, e.g., overlap extension PCR. Next, the genetic material may be amplified using flanking primers with sufficient overlap with the yeast display vector for homologous recombination in yeast. These methods allow CNTFR ligand libraries to be created at relatively low cost and effort. Synthetic libraries and recent methods have been developed that allow defined control over library composition.

In certain aspects, a display library (e.g., a yeast display library) is screened for binding to the target of interest (e.g., CNTFR) by FACS. Two-color FACS may be used for library screening, where one fluorescent label can be used to detect the c-myc epitope tag and the other to measure interaction of the CNTFR ligand against the binding target of interest. Different instrument lasers and/or filter sets can be used to measure excitation and emission properties of the two fluorophores at single-cell resolution. This enables yeast expression levels to be normalized with binding. That is, a CNTFR ligand that exhibits poor yeast expression but binds a high amount of a target can be distinguished from a CNTFR ligand that is expressed at high levels but binds weakly to a target. Accordingly, a two-dimensional flow cytometry plot of expression versus binding will result in a diagonal population of yeast cells that bind to target. High-affinity binders can be isolated using library sort gates. Alternatively, in an initial sort round it could be useful to clear the library of undesired clones that do not express full-length protein.

Following enrichment of CNTFR ligand libraries for clones encoding CNTFR ligands of interest, the yeast plasmids are recovered and sequenced. Additional rounds of FACS can be performed under increased sorting stringency. The binding affinities or kinetic off-rates of individual yeast-displayed CNTFR ligand clones may then be measured.

Once CNTFR ligands of interest have been identified by surface display (e.g., yeast surface display), the engineered CNTFR ligands may be produced using a suitable method. According to certain embodiments, the CNTFR ligand is produced by solid phase peptide synthesis. CNTFR ligand polypeptide sequences may be synthesized using solid phase peptide chemistry on an automated synthesizer. For example, standard 9-fluorenylmethyloxycarbonyl (Fmoc)-based solid phase peptide chemistry may be employed. Solid phase synthesis may be followed by purification, e.g., by reversed-phase high-performance liquid chromatography (RP-HPLC).

In certain aspects, the CNTFR ligands are produced using a recombinant DNA approach. Strategies have been developed for producing proteins such as CNTFR ligands using recombinant methods in a variety of host cell types. For example, functional CNTFR ligands may be produced with barnase as a genetic fusion partner, which promotes folding in the *E. coli* periplasmic space and serves as a useful purification handle. According to certain embodiments, the CNTFR ligand is expressed in yeast (e.g., the yeast strain *Pichia pastoris* or *Saccharomyces cerevesiae*) or mammalian cells (e.g. human embryonic kidney cells or Chinese hamster ovary cells). The expression construct may encode one or more tags (e.g., a C-terminal hexahistadine tag for purification by, e.g., metal chelating chromatography (Ni-NTA)). Size exclusion chromatography or high performance liquid chromatography may then be used to remove aggregates, misfolded multimers, and the like.

Aspects of the present disclosure include nucleic acids that encode the CNTFR ligands of the present disclosure. That is, provided are nucleic acids that encode any of the CNTFR ligands described herein. In certain aspects, such a nucleic acid is present in an expression vector. The expression vector includes a promoter operably linked to the nucleic acid encoding the CNTFR ligand, the promoter being selected based on the type of host cell selected to express the CNTFR ligand. Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance, neomycin resistance, and/or the like) to permit detection of those cells transformed with the desired DNA sequences.

Also provided are host cells that include a nucleic acid that encodes any of the CNTFR ligands described herein, as well as any expression vectors including the same. *Escherichia coli* is an example of a prokaryotic host cell that can be used for cloning a nucleic acid encoding a CNTFR ligand of the present disclosure. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* (e.g., *S. cerevisiae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells (e.g., mammalian cells grown in in vitro cell culture) can also be used to express and produce the CNTFR ligands of the present disclosure. Suitable mammalian host cells include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like. Expression vectors for these cells can include expression control sequences, such as an origin of replication, a promoter, and an enhancer, and necessary processing information sites, such as ribosome binding sites, RNA splice sites, polyadenylation sites, and transcriptional terminator sequences. Examples of suitable expression control sequences are promoters derived from immunoglobulin genes, SV40, adenovirus, bovine papilloma virus, cytomegalovirus and the like.

Once synthesized (either chemically or recombinantly), the CNTFR ligands can be purified according to standard procedures known in the art, including ammonium sulfate precipitation, affinity columns, column chromatography, high performance liquid chromatography (HPLC) purification, gel electrophoresis, and the like. A subject CNTFR ligand can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than the CNTFR ligand, etc.

Fusion Proteins and Conjugates

In certain aspects, provided are CNTFR ligands (e.g., any of the CNTFR ligands described herein) stably associated with (e.g., fused, conjugated, or otherwise attached to) a heterologous moiety.

In some embodiments, provided are fusion proteins in which a CNTFR ligand is fused to a heterologous polypeptide. Heterologous polypeptides of interest include, but are not limited to, an Fc domain (e.g., a human or mouse Fc domain), an albumin, a transferrin, XTEN, a homo-amino acid polymer, a proline-alanine-serine polymer, an elastin-like peptide, or any combination thereof. In certain aspects, the heterologous polypeptide increases the stability and/or serum half-life of the CNTFR ligand upon its administration to an individual in need thereof, as compared to the same CNTFR ligand which is not fused to the heterologous polypeptide. In certain aspects, provided are fusion proteins that include any of the CNTFR ligands of the present disclosure fused to a human Fc domain (e.g., a full-length human Fc domain or fragment thereof). According to certain embodiments, such a fusion protein finds use, e.g., in administering to an individual in need thereof in accordance with the methods of the present disclosure, e.g., an individual having a cell proliferative disorder associated with CNTFR signaling, an individual having a neurodegenerative disorder, and/or the like. A non-limiting example of a human Fc domain that may be fused to any of the CNTFR ligands of the present disclosure is a human IgG1 Fc domain having the sequence set forth in Table 3 below (SEQ ID NO:7), or a fragment thereof.

TABLE 3

Amino Acid Sequence of an Example Human Fc Domain

| | Amino Acid Sequence |
|---|---|
| Example Human Fc Domain (SEQ ID NO: 7) | DKTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSR WQQGNVFSCSVMHEALHNHYTQKSLSLSPGK |

According to certain embodiments, provided are conjugates in which a CNTFR ligand of the present disclosure is conjugated to a moiety. Moieties of interest include, but are not limited to, polyethylene glycol (PEG), an anti-cancer drug, a detectable label, and combinations thereof.

Anti-cancer drugs of interest include agents that inhibit cell proliferation and/or kill cancer cells. Such agents may vary and include cytostatic agents and cytotoxic agents (e.g., an agent capable of killing a target cell tissue with or without being internalized into a target cell). In certain aspects, the therapeutic agent is a cytotoxic agent selected from an enediyne, a lexitropsin, a duocarmycin, a taxane, a puromycin, a dolastatin, a maytansinoid, and a *vinca* alkaloid. In some embodiments, the cytotoxic agent is paclitaxel, docetaxel, CC-1065, CPT-11 (SN-38), topotecan, doxorubicin, morpholino-doxorubicin, rhizoxin, cyanomorpholino-doxorubicin, dolastatin-10, echinomycin, combretastatin, calicheamicin, maytansine, maytansine DM1, maytansine DM4, DM-1, an auristatin or other dolastatin derivatives, such as auristatin E or auristatin F, AEB (AEB-071), AEVB (5-benzoylvaleric acid-AE ester), AEFP (antibody-endostatin fusion protein), MMAE (monomethylauristatin E), MMAF (monomethylauristatin F), pyrrolobenzodiazepines (PBDs), eleutherobin, netropsin, or any combination thereof. According to certain embodiments, the agent is a protein toxin selected from hemiasterlin and hemiasterlin analogs such as HTI-286 (e.g., see U.S. Pat. No. 7,579,323; WO 2004/

026293; and U.S. Pat. No. 8,129,407, the full disclosures of which are incorporated herein by reference), abrin, brucine, cicutoxin, diphtheria toxin, batrachotoxin, botulism toxin, shiga toxin, endotoxin, *Pseudomonas* exotoxin, *Pseudomonas* endotoxin, tetanus toxin, pertussis toxin, anthrax toxin, cholera toxin, falcarinol, fumonisin BI, fumonisin B2, afla toxin, maurotoxin, agitoxin, charybdotoxin, margatoxin, slotoxin, scyllatoxin, hefutoxin, calciseptine, taicatoxin, calcicludine, geldanamycin, gelonin, lotaustralin, ocratoxin A, patulin, ricin, strychnine, trichothecene, zearlenone, and tetradotoxin. Enzymatically active toxins and fragments thereof which may be employed include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes.

Detectable labels include labels that may be detected in an application of interest (e.g., in vitro and/or in vivo research and/or clinical applications). Detectable labels of interest include radioisotopes, enzymes that generate a detectable product (e.g., horseradish peroxidase, alkaline phosphatase, etc.), fluorescent proteins, paramagnetic atoms, and the like. In certain aspects, the CNTFR ligand is conjugated to a specific binding partner of detectable label (e.g., conjugated to biotin such that detection may occur via a detectable label that includes avidin/streptavidin).

According to certain embodiments, the agent is a labeling agent that finds use in in vivo imaging, such as near-infrared (NIR) optical imaging, single-photon emission computed tomography (SPECT)/CT imaging, positron emission tomography (PET), nuclear magnetic resonance (NMR) spectroscopy, or the like. Labeling agents that find use in such applications include, but are not limited to, fluorescent labels, radioisotopes, and the like. In certain aspects, the labeling agent is a multi-modal in vivo imaging agent that permits in vivo imaging using two or more imaging approaches (e.g., see Thorp-Greenwood and Coogan (2011) *Dalton Trans.* 40:6129-6143).

In certain aspects, the labeling agent is an in vivo imaging agent that finds use in near-infrared (NIR) imaging applications, which agent is selected from a Kodak X-SIGHT dye, Pz 247, DyLight 750 and 800 Fluors, Cy 5.5 and 7 Fluors, Alexa Fluor 680 and 750 Dyes, IRDye 680 and 800CW Fluors. According to certain embodiments, the labeling agent is an in vivo imaging agent that finds use in SPECT imaging applications, which agent is selected from $^{99m}$Tc, $^{111}$In, $^{123}$In, $^{201}$Tl, and $^{133}$Xe. In certain aspects, the labeling agent is an in vivo imaging agent that finds use in positron emission tomography (PET) imaging applications, which agent is selected from $^{11}$C, $^{13}$N, $^{15}$O, $^{18}$F, $^{64}$Cu, $^{62}$Cu, $^{124}$I, $^{76}$Br, $^{82}$Rb and $^{68}$Ga.

Linkers that find use in the conjugates of the present disclosure include ester linkers, amide linkers, maleimide or maleimide-based linkers; valine-citrulline linkers; hydrazone linkers; N-succinimidyl-4-(2-pyridyldithio)butyrate (SPDB) linkers; Succinimidyl-4-(N-maleimidomethyl)cyclohexane-1-carboxylate (SMCC) linkers; vinylsulfone-based linkers; linkers that include polyethylene glycol (PEG), such as, but not limited to tetraethylene glycol; linkers that include propanoic acid; linkers that include caproleic acid, and linkers including any combination thereof.

Numerous strategies are available for linking a CNTFR ligand to a moiety of interest through a linker. For example, the moiety of interest may be derivatized by covalently attaching the linker to the drug, where the linker has a functional group capable of reacting with a "chemical handle" on the CNTFR ligand. The functional group on the linker may vary and may be selected based on compatibility with the chemical handle on the CNTFR ligand. According to one embodiment, the chemical handle on the CNTFR ligand is provided by incorporation of an unnatural amino acid having the chemical handle into the CNTFR ligand. Such an unnatural amino acid may be incorporated into a CNTFR ligand, e.g., via chemical synthesis or recombinant approaches, e.g., using a suitable orthogonal amino acyl tRNA synthetase-tRNA pair for incorporation of the unnatural amino acid during translation in a host cell.

The functional group of an unnatural amino acid present in the CNTFR ligand may be an azide, alkyne, alkene, amino-oxy, hydrazine, aldehyde, nitrone, nitrile oxide, cyclopropene, norbornene, iso-cyanide, aryl halide, boronic acid, or other suitable functional group, and the functional group on the linker is selected to react with the functional group of the unnatural amino acid (or vice versa).

Compositions

Also provided are compositions that include a CNTFR ligand of the present disclosure. The compositions may include, e.g., any of the CNTFR ligands described herein.

In certain aspects, the compositions include a CNTFR ligand of the present disclosure present in a liquid medium. The liquid medium may be an aqueous liquid medium, such as water, a buffered solution, and the like. One or more additives such as a salt (e.g., NaCl, MgCl$_2$, KCl, MgSO$_4$), a buffering agent (a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino) propanesulfonic acid (MOPS), N-tris[Hydroxymethyl] methyl-3-aminopropanesulfonic acid (TAPS), etc.), a protease inhibitor, glycerol, and the like may be present in such compositions.

Pharmaceutical compositions are also provided. The pharmaceutical compositions include any of the CNTFR ligands of the present disclosure, and a pharmaceutically-acceptable carrier. The pharmaceutical compositions generally include a therapeutically effective amount of the CNTFR ligand. By "therapeutically effective amount" is meant a dosage sufficient to produce a desired result, e.g., an amount sufficient to effect beneficial or desired therapeutic (including preventative) results, such as a reduction in cellular proliferation in an individual having a cell proliferative disorder associated with CNTFR signaling, reduction in neurodegeneration in an individual having a neurodegenerative disorder, and/or the like.

A CNTFR ligand of the present disclosure can be incorporated into a variety of formulations for therapeutic administration. More particularly, the CNTFR ligand can be formulated into pharmaceutical compositions by combination with appropriate pharmaceutically acceptable excipients or diluents, and may be formulated into preparations in solid, semi-solid, liquid or gaseous forms, such as tablets, capsules, powders, granules, ointments, solutions, injections, inhalants and aerosols.

Formulations of the CNTFR ligands of the present disclosure suitable for administration to an individual (e.g., suitable for human administration) are generally sterile and may further be free of detectable pyrogens or other contaminants contraindicated for administration to an individual according to a selected route of administration.

In pharmaceutical dosage forms, the CNTFR ligand can be administered alone or in appropriate association, as well as in combination, with other pharmaceutically-active compounds. The following methods and excipients are merely examples and are in no way limiting.

For oral preparations, the CNTFR ligand can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The CNTFR ligands can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The pharmaceutical composition may be in a liquid form, a lyophilized form or a liquid form reconstituted from a lyophilized form, where the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration.

An aqueous formulation of the CNTFR ligand may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

Methods of Use

Also provided are methods of using the CNTFR ligands and compositions of the present disclosure. In certain aspects, provided are methods that include administering a CNTFR ligand or composition of the present disclosure to an individual (e.g., a mammal, such as a human). According to certain embodiments, provided are methods that include administering to an individual in need thereof a therapeutically effective amount of a CNTFR ligand or pharmaceutical composition of the present disclosure. In certain aspects, the individual in need thereof has a cell proliferative disorder associated with CNTFR signaling, and the administering is effective in treating the cell proliferative disorder. For example, a CNTFR ligand that results in reduced affinity of gp130 and/or LIFR for a complex that includes the CNTFR ligand and CNTFR (which ligand may optionally exhibit increased binding affinity for CNTFR relative to the corresponding wild-type ligand) may be employed to inhibit CNTFR signaling in an individual having a cell proliferative disorder associated with CNTFR signaling. In certain aspects, the cell proliferative disorder is cancer.

For example, in some embodiments, a CNTFR ligand or pharmaceutical composition of the present disclosure inhibits growth, metastasis and/or invasiveness of a cancer cell(s) in a host when the CNTFR ligand or pharmaceutical composition is administered in an effective amount. By "cancer cell" is meant a cell exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth and/or development in an immunocompromised non-human animal model, and/or any appropriate indicator of cellular transformation. "Cancer cell" may be used interchangeably herein with "tumor cell", "malignant cell" or "cancerous cell", and encompasses cancer cells of a solid tumor, a semi-solid tumor, a primary tumor, a metastatic tumor, and the like.

Cancers which may be treated using the methods of the present disclosure include, but are not limited to, solid tumors, lung cancer (e.g., non-small cell lung cancer (NSCLC), breast cancer, prostate cancer, pancreatic cancer, colorectal carcinoma, renal cell carcinoma, Hodgkin's lymphoma, Non-Hodgkin's lymphoma, anaplastic large cell lymphoma, acute myelogenous leukemia, multiple myeloma, and any other type of cancer which may be treated using a CNTFR ligand or pharmaceutical composition of the present disclosure.

In certain aspects, the individual in need thereof has a neurodegenerative disorder, and the administering is effective in treating the neurodegenerative disorder. For example, a CNTFR ligand (e.g., a CNTFR ligand that exhibits increased binding affinity for CNTFR relative to the corresponding wild-type ligand) may be used to stimulate CNTFR signaling in a manner that is neuroprotective, e.g., inhibits neurodegeneration. Neurodegenerative disorders that may be treated according to the methods of the present disclosure include, but are not limited to, Alzheimer's Disease (AD), Parkinson's Disease (PD), Lewy body dementia, frontotemporal dementia, amyotrophic lateral sclerosis (ALS), Huntington disease, and prion diseases. As such, the individual to which the CNTFR ligand is administered may have any of the aforementioned neurodegenerative diseases.

The CNTFR ligand may be administered alone (e.g., in monotherapy) or in combination (e.g., in combination therapy) with one or more additional therapeutic agents.

In some embodiments, an effective amount of the CNTFR ligand (or pharmaceutical composition including same) is an amount that, when administered alone (e.g., in monotherapy) or in combination (e.g., in combination therapy) with one or more additional therapeutic agents, in one or more doses, is effective to reduce the symptoms of a cell proliferative disorder (e.g., cancer) or neurodegenerative disorder in the individual by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the symptoms in the individual in the absence of treatment with the CNTFR ligand or pharmaceutical composition.

In certain aspects, the methods of the present disclosure inhibit growth, metastasis and/or invasiveness of cancer cells in the individual when the CNTFR ligand or pharmaceutical composition is administered in an effective amount.

The CNTFR ligand or pharmaceutical composition may be administered to an individual using any available method and route suitable for drug delivery, including in vivo and ex vivo methods, as well as systemic and localized routes of administration. Conventional and pharmaceutically acceptable routes of administration include intranasal, intramuscular, intra-tracheal, subcutaneous, intradermal, topical application, ocular, intravenous, intra-arterial, nasal, oral, and other enteral and parenteral routes of administration. Routes of administration may be combined, if desired, or adjusted depending upon the CNTFR ligand and/or the desired effect. The CNTFR ligands or pharmaceutical compositions may be administered in a single dose or in multiple doses. In some embodiments, the CNTFR ligand or pharmaceutical composition is administered intravenously. In some embodiments, the CNTFR ligand or pharmaceutical composition is administered by injection, e.g., for systemic delivery (e.g., intravenous infusion) or to a local site.

A variety of individuals are treatable according to the subject methods. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the individual is a human.

By "treating" or "treatment" is meant at least an amelioration of the symptoms associated with the cell proliferative disorder (e.g., cancer) or neurodegenerative disorder of the individual, where amelioration is used in a broad sense to refer to at least a reduction in the magnitude of a parameter, e.g. symptom, associated with the cell proliferative disorder or neurodegenerative disorder being treated. As such, treatment also includes situations where the cell proliferative disorder or neurodegenerative disorder, or at least symptoms associated therewith, are completely inhibited, e.g., prevented from happening, or stopped, e.g., terminated, such that the individual no longer suffers from the cell proliferative disorder or neurodegenerative disorder, or at least the symptoms that characterize the cell proliferative disorder or neurodegenerative disorder.

Dosing is dependent on severity and responsiveness of the disease state to be treated. Optimal dosing schedules can be calculated from measurements of drug accumulation in the body of the patient. The administering physician can determine optimum dosages, dosing methodologies and repetition rates. Optimum dosages may vary depending on the relative potency of individual CNTFR ligands, and can generally be estimated based on $EC_{50}$s found to be effective in in vitro and in vivo animal models, etc. In general, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, where the CNTFR ligand or pharmaceutical composition is administered in maintenance doses, ranging from 0.01 μg to 100 g per kg of body weight, once or more daily, to once every several months, once every six months, once every year, or at any other suitable frequency.

The therapeutic methods of the present disclosure may include administering a single type of CNTFR ligand to a subject, or may include administering two or more types of CNTFR ligands to a subject by administration of a cocktail of different CNTFR ligands.

In some embodiments, the methods include, prior to the administering the CNTFR ligand or pharmaceutical composition, identifying the individual as having a cell proliferative disorder associated with CNTFR signaling, or a neurodegenerative disorder. Identifying the individual as having a cell proliferative or neurodegenerative disorder associated with CNTFR signaling may be carried out using a variety of approaches and combinations thereof. In certain aspects, the identifying is based on CNTFR ligand abundance in a sample obtained from the individual. The CNTFR ligand may be one or more of CNTF, CLCF1, NP, etc., and any combinations thereof. In certain aspects, the sample includes cancer-associated fibroblasts (CAFs, such as normal lung fibroblasts (NLFs)), and identifying the individual as having a cell proliferative or neurodegenerative disorder associated with CNTFR signaling is based on the level of CLCF1 expression in the CAFs. In some embodiments, the CNTFR ligand abundance is quantified using a soluble CNTFR polypeptide as a CNTFR ligand capture agent.

According to certain embodiments, the identifying is based on CNTFR abundance and/or the abundance of CNTFR-gp130-LIFR tripartite receptor complexes in a sample obtained from the individual. In certain aspects, the identifying is based on the level of CNTFR signaling in a sample obtained from the individual. The level of CNTFR signaling may be based on the phosphorylation status of one or more CNTFR signaling pathway molecules. For example, the present inventors have determined that binding of CNTFR to CLCF1 results in activation of the Jak-STAT and Ras-Raf-MEK-ERK signaling pathways, as schematically illustrated in FIG. 1. As such, the abundance, activity, phosphorylation status, and/or the like of any of Jak, STAT, Ras, Raf, MEK, ERK, or any combination thereof, may be assessed to determine aberrant CNTFR signaling in the individual.

The identifying may be based on ligands, CNTFR molecules, CNTFR-gp130-LIFR tripartite receptor complexes, etc. quantified using any suitable approaches. According to certain embodiments, the identifying is based on an immunoassay. A variety of suitable immunoassay formats are available, including ELISA, flow cytometry assays, immunohistochemistry on tissue section samples, immunofluorescence on tissue section samples, Western analysis, and/or the like.

In some embodiments, the identifying is based on nucleic acid sequencing. For example, the number of sequencing reads corresponding to an mRNA encoding a protein of interest may be used to determine the expression level of the protein. In certain aspects, the sequencing is performed using a next-generation sequencing system, such as on a a sequencing platform provided by Illumina® (e.g., the HiSeq™, MiSeq™ and/or Genome Analyzer™ sequencing systems); Ion Torrent™ (e.g., the Ion PGM™ and/or Ion Proton™ sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems); or any other sequencing platform of interest. Protocols for isolating nucleic acids from tissue or fluid samples, as well as protocols for preparing sequencing libraries having sequencing adapters appropriate for the desired sequencing platform are readily available.

In some embodiments, methods that include identifying the individual as having a cell proliferative or neurodegenerative disorder associated with CNTFR signaling further include obtaining the sample from the individual.

The sample obtained from the individual may be any sample suitable for determining whether the individual has a cell proliferative or neurodegenerative disorder associated with CNTFR signaling. In certain aspects, the sample is a fluid sample, such as whole blood, serum, plasma, or the like. In some embodiments, the sample is a tissue sample. Tissue samples of interest include, but are not limited to, tumor biopsy samples, and the like.

A variety of suitable approaches are available to identify an individual as having a neurodegenerative disorder. In certain aspects, the identifying comprises neuroimaging of the individual, electroencephalography (EEG), biomarker analysis (e.g., measuring a biomarker (such as a misfolded protein) in blood or urine of the individual), or any combination thereof.

Kits

Also provided by the present disclosure are kits. According to certain embodiments, the kits include a therapeutically effective amount of any of the CNTFR ligands described herein, or any of the pharmaceutical compositions described herein, and instructions for administering the CNTFR ligand or pharmaceutical composition to an individual in need thereof (e.g., an individual identified as having a cell proliferative disorder associated with CNTFR signaling, or a neurodegenerative disorder). In certain aspects, the kits include a CNTFR ligand or a pharmaceutical composition of the present disclosure, present in a container. The container may be a tube, vial, or the like. According to certain embodiments, the kit includes the CNTFR ligand or the pharmaceutical composition present in one or more unit dosages, such as 1, 2 or more, 3 or more, 4 or more, 5 or more, etc. unit dosages.

Components of the kits may be present in separate containers, or multiple components may be present in a single container.

The instructions for administering the CNTFR ligand or pharmaceutical composition to an individual may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

In some embodiments, provided are kits that include a CNTFR ligand capture agent and instructions for using the capture agent to quantify a CNTFR ligand abundance present in a biological sample. The CNTFR ligand may be one or more of CNTF, CLCF1, NP, etc., and any combinations thereof. In some embodiments, the CNTFR ligand abundance is quantified using a soluble CNTFR polypeptide as a CNTFR ligand capture agent.

The following examples are offered by way of illustration and not by way of limitation.

EXPERIMENTAL

Example 1—Engineering Variant CNTFR Ligands Exhibiting Increased Binding Affinity for CNTFR It was hypothesized that variant CNTFR ligands could be employed as a therapeutic to increase CNTFR signaling (e.g., to treat a neurodegenerative disorder), and that a CNTFR ligand having a greater binding affinity for CNTFR as compared the corresponding wild-type CNTFR ligand would be desirable in this context. In this particular example, CLCF1 variants were generated and assessed for binding affinity to CNTFR, although the materials and methods employed in this example are readily applicable to other CNTFR ligands, such as CNTF and neuropoetin (NP1).

Introduction

While the detection of amyloid plaques or neurofibrillary tangles (NFTs) have been known as the hallmarks of Alzheimer's Disease (AD) and has diagnostic value, their exact role in the pathogenesis of AD remains controversial. For example, people with substantial plaque burdens can have normal condition, suggesting that plaque loads may not necessarily correlate with functional impairments. Major anti-amyloid treatments that have been tested can be divided into Aβ fragments for active immunization, Aβ targeting antibodies for passive immunization, small molecules that target amyloid precursor protein (APP) cleavage enzyme, presenilin, and small molecules that target another APP cleavage enzyme, BACE1. All phase III clinical trials for treatments targeting β amyloid have failed to show cognitive improvement although some led to reductions of β amyloid. These studies do not necessarily disprove the amyloid hypothesis, however, orthogonal strategies that directly induce neuronal survival, neurogenesis, or synaptogenesis to slow or compensate for neuronal damages with well-established mechanisms may provide a critical stand-alone or adjuvant treatment.

Neurotrophic factors, or neurotrophins, are a group of growth factors that regulate pathways involved in prosurvival and pro-functional responses in neurons. They are a critical component during development and maintenance of the vertebrate nervous system. Much evidence shows the importance of neurotrophins in AD. For example, inhibition of nerve growth factor (NGF) by antibodies led to pathological phenotypes similar to those observed in AD in a mouse model. Alterations in NGF and brain-derived neurotrophic factor (BDNF) levels are found in AD patients as well as in other disorders such as Down's syndrome (DS), PD, and HD. Pre-clinical and clinical studies are currently underway to use NGF, BDNF, GDNF, neurturin, and neurotrophin-3 (NT-3) as therapeutic agents for neurological disorders, but discovery of optimal drug targets and effective therapeutics that act on these targets without toxicity still remains a major challenge.

Neurodegenerative diseases are complex disorders and the failures of monotherapy suggest more potent approaches are needed. In part, this is because the blood brain barrier (BBB) makes it difficult for proteins to cross from the blood into the brain. Moreover, infusion through direct intracerebroventricular injection has been associated with significant side effects. Equally important is target specificity, since heavy crosstalk between multiple circuits of the brain makes it especially vulnerable to off-target toxicities. To address this need, described herein is a novel engineered growth factor ligand with optimized neuro-receptor targeting properties, with the goal of maximizing efficacy with reduced side effects.

Figure 2:
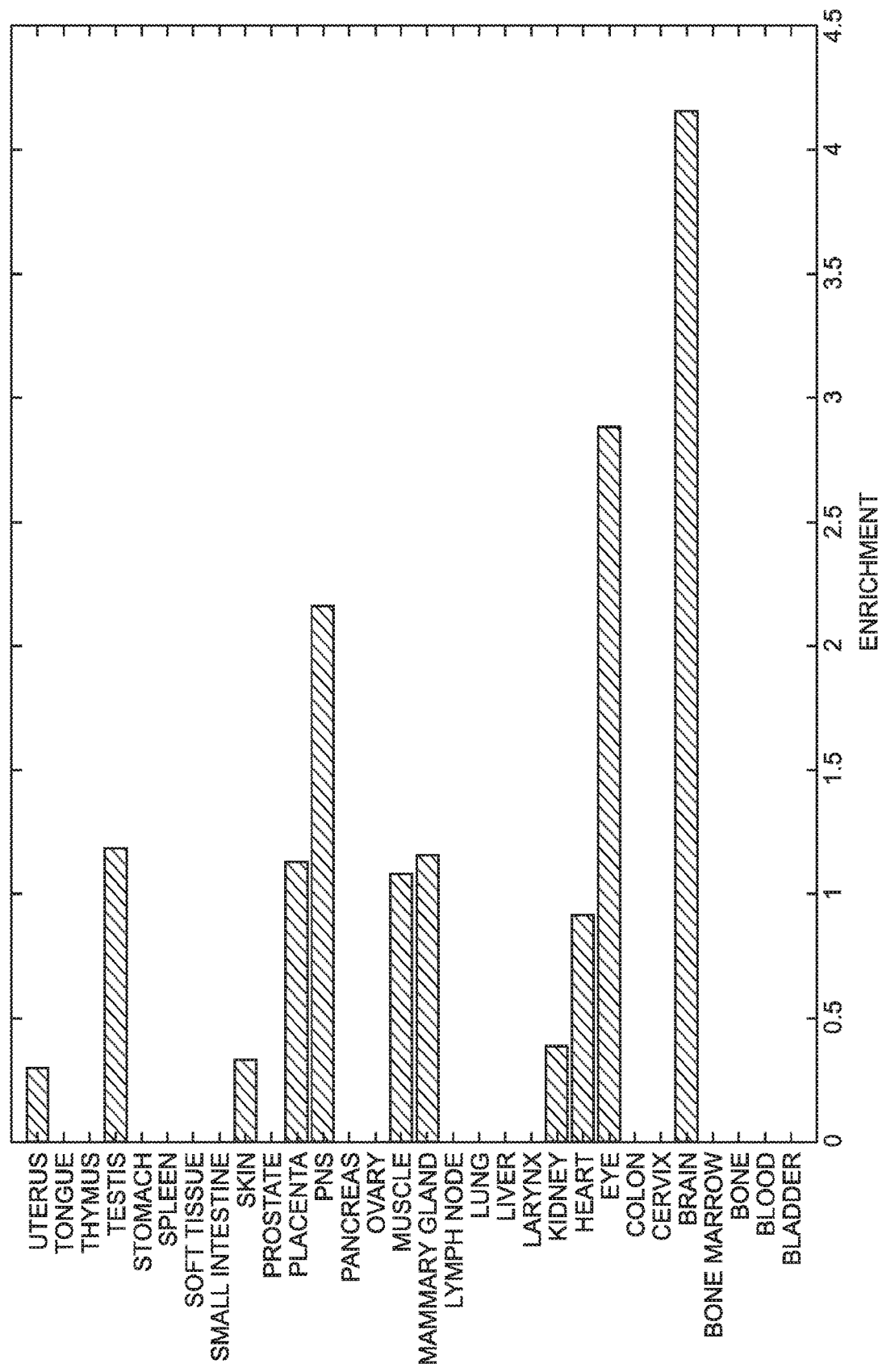
FIG. 2 is a graph showing normalized expression of CNTFR in various tissues. Tissue-specific expression levels of CNTFR was acquired from Tissue-specific Gene Expression and Regulation (TiGER) database of the Bioinformatics Lab at Wilmer Eye Institute of Johns Hopkins University [10]. The gene expression pattern for each UniGene in 30 human tissues was calculated based on NCBI EST (expressed sequence tag) database. The expression level is normalized with tissue-library size. Each value for a gene is a tissue is a ratio of observed ESTs to the expected on in this tissue. The expected number of ESTs is the product of total ESTs of the gene and the fraction of total ESTs in the tissue among all ESTs in 30 tissues.
Figure 3:
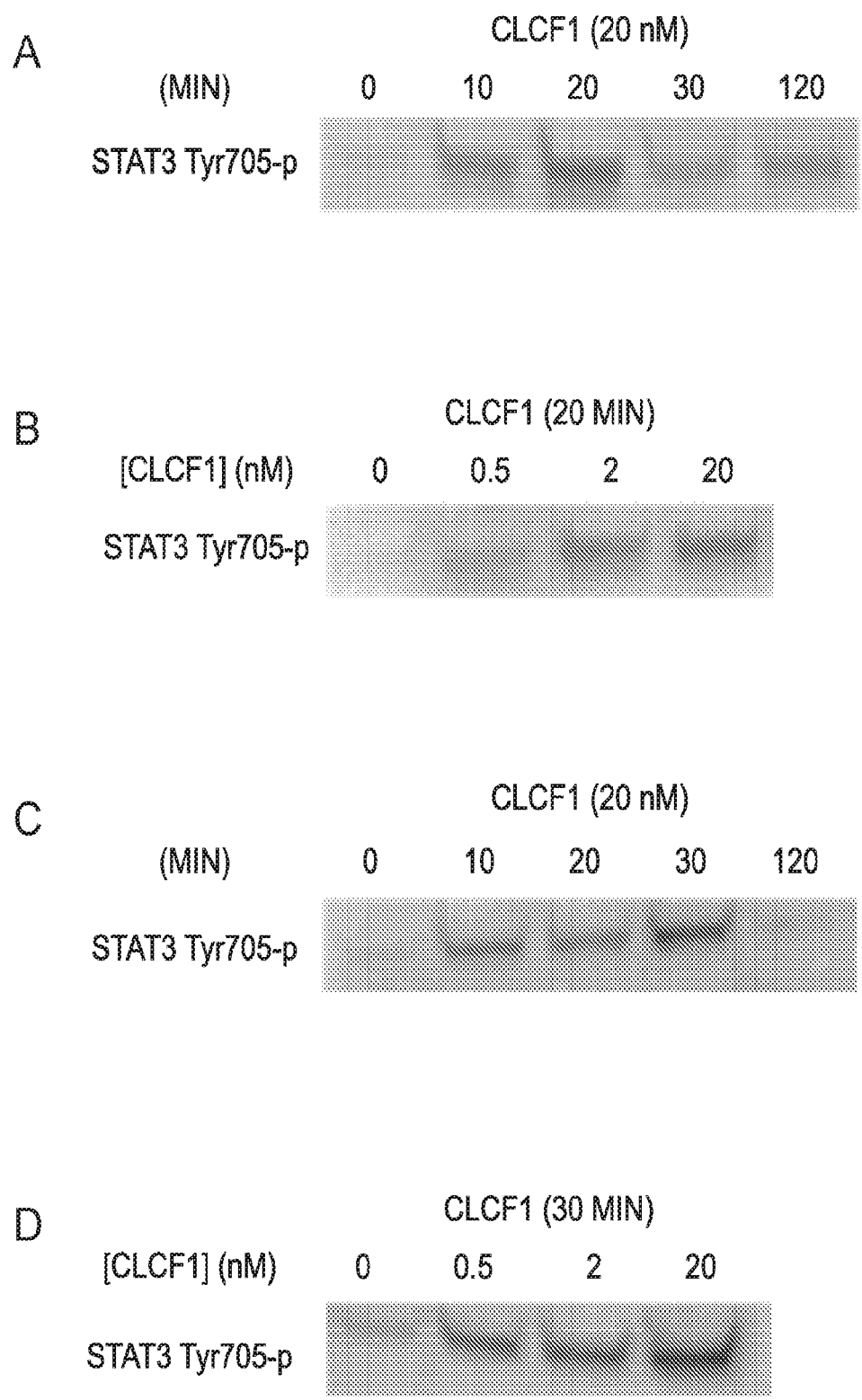
FIG. 3, panels A-D, shows data demonstrating that recombinant CLCF1 activates STAT3. The levels of p-STAT3 at Tyr705 in SH-SY5Y cell line (panels A and B) and E18 cells (panels C and D). CLCF1 activates STAT3 in both a time-(panels A and C) and concentration-(panels B and D) dependent manner.
Figure 5:
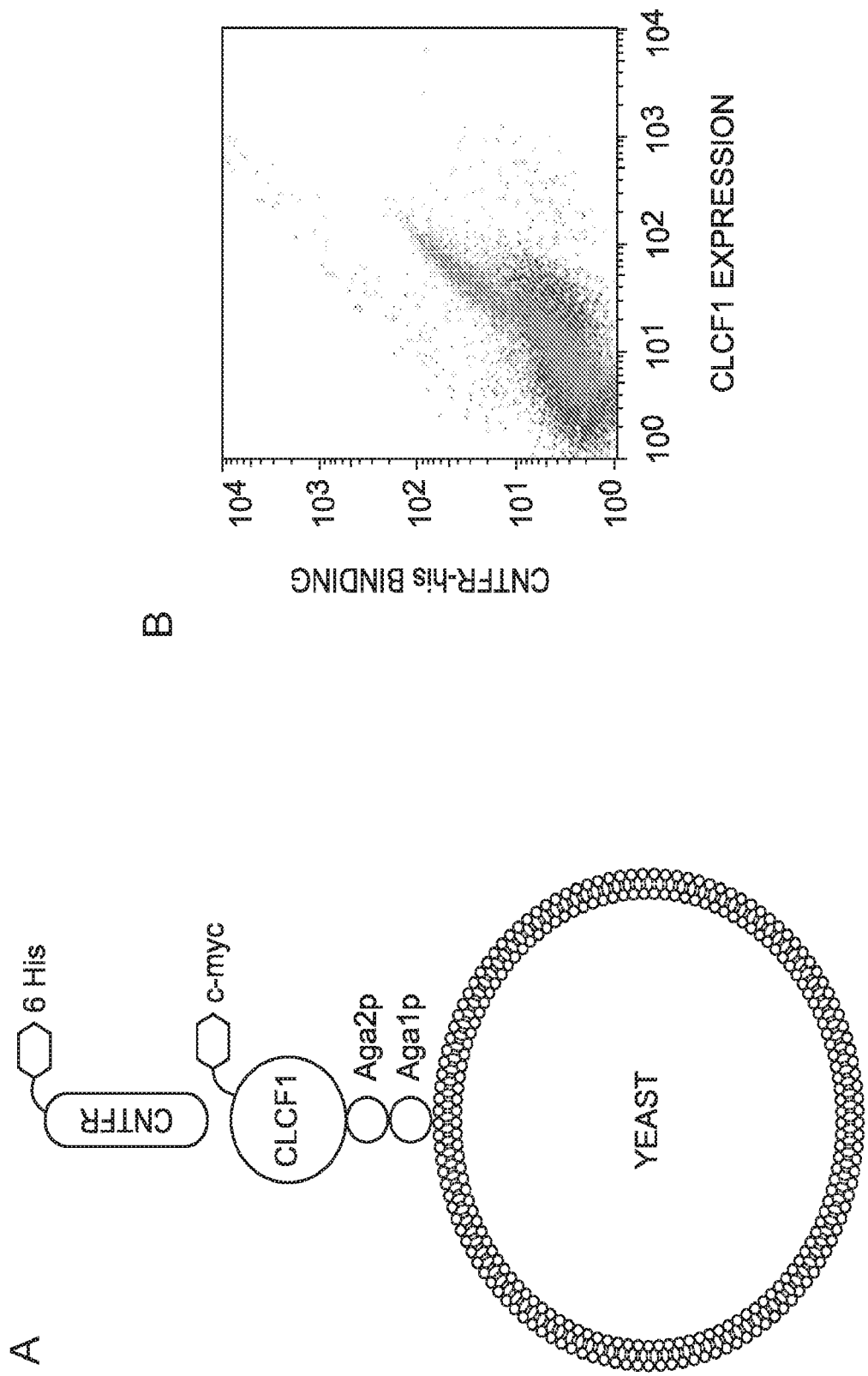
FIG. 5, panels A and B, show yeast displayed CLCF1 for protein engineering. Panel A: CLCF1 was displayed as a fusion to yeast surface mating protein Aga2p. Panel B: Flow cytometry scatter plot showing that when treated with 20 nM CNTFR-HIS the CLCF1 expressing population (as measured with chicken anti-c-myc tag antibody and anti-chicken-PE antibody) has increased binding signal for CNTFR (as measured by mouse anti-HIS Hilyte Fluor 488).
Figure 7:
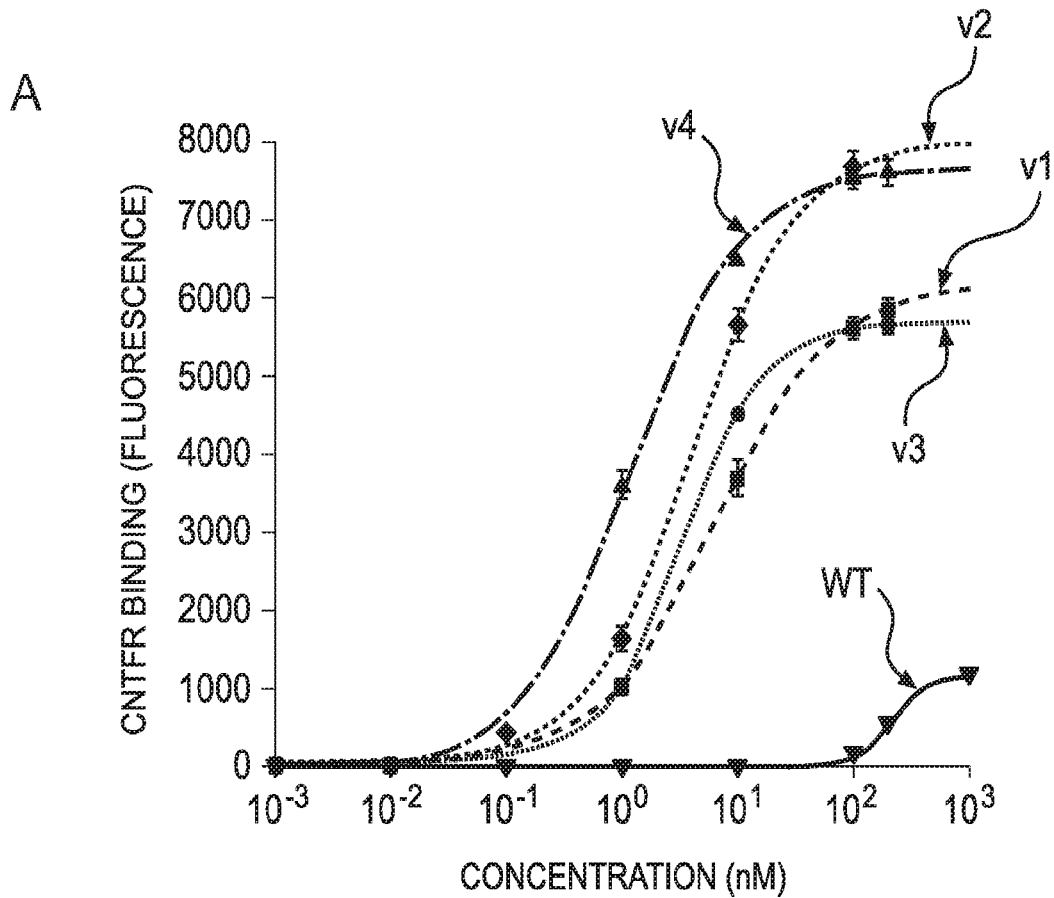
FIG. 7, panels A and B, shows the characterization of affinity matured CLCF1 variants. Panel A: CNTFR binding to yeast displaying CLCF1 variants isolated from screening and wild-type (WT) CLCF1. Panel B: Apparent Kd values of yeast-displayed CLCF1 constructs.
Figure 8:
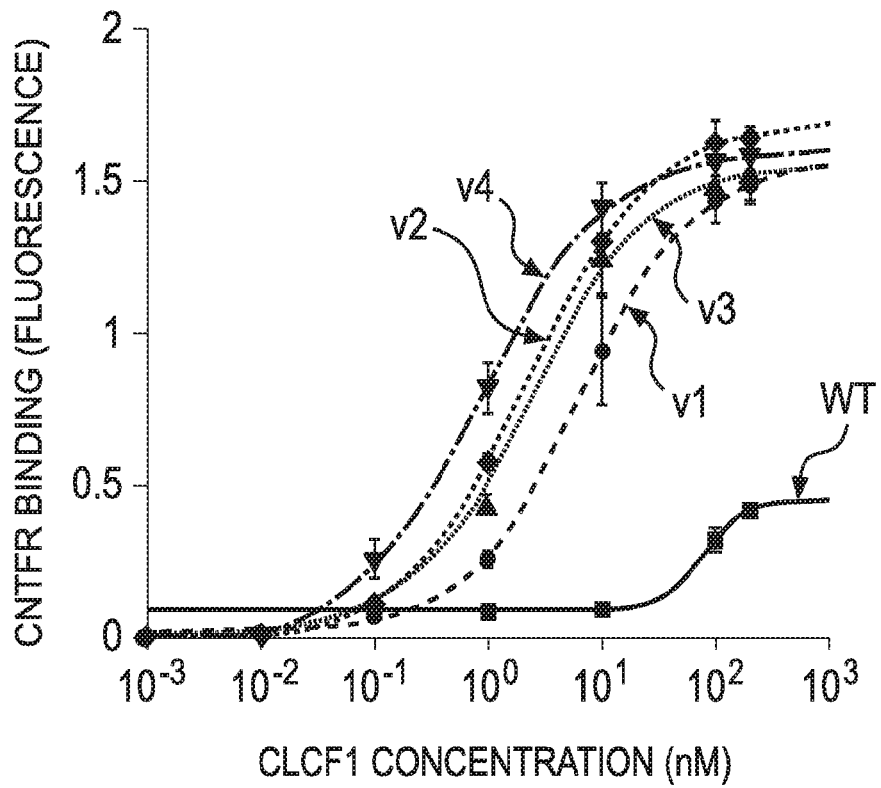
FIG. 8, panels A-D, shows the characterization of recombinantly expressed CLCF1 variants. Panels A and B: The apparent binding affinities ($K_d$) of the soluble, recombinant CLCF1 wild-type (WT) and variants were comparable to those of yeast-displayed constructs. Increased binding affinity to CNTFR leads to increased binding to gp130 (panel C) and LIFR (panel D). Significance was measured against wild-type CLCF1. *P<0.05, **P<0.01.

Ciliary neurotrophic factor receptor (CNTFR) is highly expressed in the brain and the peripheral nervous system (FIG. 2), and supports the survival of neurons. Ciliary neurotrophic factor (CNTF), the first ligand discovered for CNTFR, was shown to have a direct neuroprotective effect on degenerating neurons in stress-induced conditions, both in cell culture and in a rodent model of axotomy-induced apoptosis. The beneficial effect of CNTF was further supported in preclinical studies involving animal models of AD, HD, and ALS. Administration of soluble CNTF was tested in phase I clinical trials as a therapy for HD and ALS, but reported no observable benefit. In these studies, the treatment dose was limited by adverse effects that are linked to the activation of interleukin-6 receptor (IL6R) by CNTF, which induces an acute-phase response on human liver cells. However, these results suggest that mono-specificity for CNTFR may improve the safety profile of CNTF.

Described herein is an alternative strategy to develop an effective CNTFR targeting ligand with reduced toxicity. Cardiotrophin-like cytokine 1 (CLCF1) is a related agonist ligand for CNTFR. CLCF1 and CNTF activate CNTFR through the same mechanism of dimerization of the beta receptors glycoprotein 130 (gp130) and leukemia inhibitory factor receptor (LIFR). Unlike CNTF, CLCF1 does not naturally bind to IL6R, and thus is known to act only through CNTFR. This specificity for CNTFR will mitigate side effects caused by off-target activation of IL6R, making CLCF1 a more suitable therapeutic molecule than CNTF. However, CLCF1 has lower binding affinity for CNTFR, and thus is a weaker agonist than CNTF.

Figure 9:
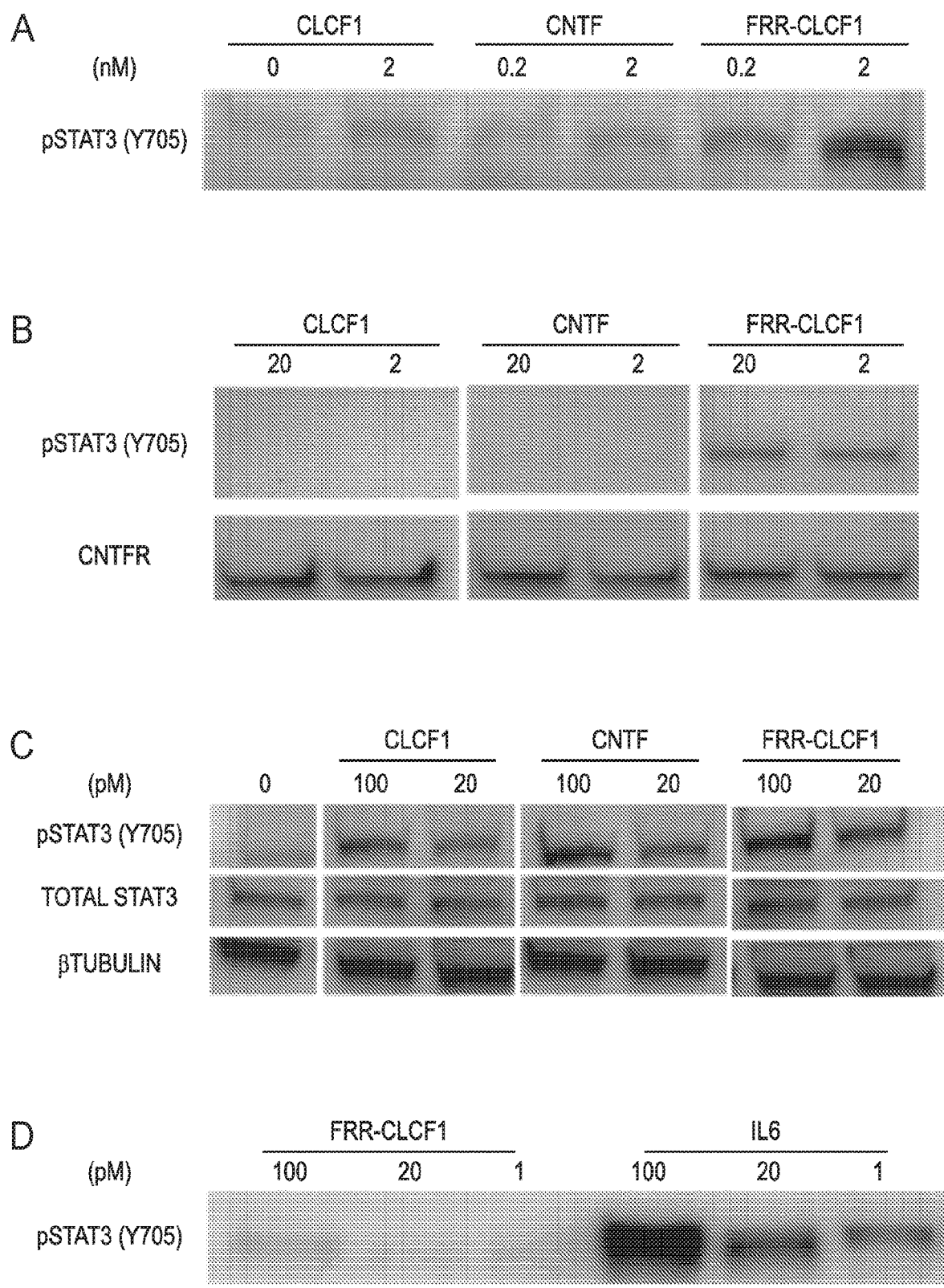
FIG. 9, panels A-D, shows data demonstrating that FRR-CLCF1 is a potent activator of STAT3 in human cell lines A549 (panel A), SH-SY5Y (panel B) and primary rat cortical neuron E18 (panel C). FRR-CLCF1 did not activate STAT3 in rat microglia (panel D) as compared to IL6.

Described herein are engineered CLCF1 variants that surpass natural CLCF1 and CNTF in potency, and directly overcome the IL6R specificity limitations of CNTF. These variants were mined from a yeast displayed library of millions of CLCF1 mutants that were screened in a high-throughput manner to identify those with tighter binding against CNTFR. Some of these variants bind even more strongly to CNTFR than CNTF, potentially allowing lower doses to be administered to further decrease side effects.

Recombinant Human CLCF1 Activates STAT3 in Human Neuroblastoma Cells and Rat Cortical Neurons Human neuroblastoma (SH-SY5Y) cells have morphological and biochemical similarity to primary neurons when differentiated and thus are used as a model cell line for in vitro studies. A recent study reported that SH-SY5Y cells express CNTFR and respond to CNTF treatment by phosphorylating STAT3 at Tyr705. Recombinant human CLCF1 was prepared. Briefly, human CLCF1 sequence was cloned into bacterial expression plasmid pET28b and transformed and expressed in Rosetta-gami 2(DE)3 cells. The expressed protein was collected and purified from inclusion body using reverse-phase high performance liquid chromatography (HPLC). Indeed, when treated with CLCF1, SH-SY5 Y phosphorylated STAT3 (Tyr705), which peaked 20 min after treatment and gradually decreased (FIG. 3, panel A). STAT3 activation was also concentration dependent (FIG. 3, panel B). To test CLCF1 treatment on primary neurons, rat embryonic cortical neurons (E18 cells) were harvested at day 18. Rat CNTFR has 94% sequence homology to human CNTFR, suggesting high likelihood of cross-reactivity. When treated with CLCF1, E18 cells showed STAT3 activation that was both time- and concentration-dependent, confirming their suitability for our in vitro studies (FIG. 3, panels C and D).

Recombinant Human CLCF1 Increases Cell Survival in Serum Starved Conditions

To examine the effect of CLCF1 on cell survival, serum starved E18 cells were treated with different concentrations of CLCF1. After 72 hours of treatment, CLCF1-treated cells displayed higher survival compared to non-treated control in concentration dependent manner (FIG. 4). Together with the phosphorylation assay results, these experiments indicated the neuro-protective effect of human CLCF1 on both human and rat cells with neuronal origin.

Engineering High Affinity CLCF1 Variants Using Yeast Surface Display

Yeast display is a robust and versatile technology that allows engineering and quantitative, real-time assessment of proteins. It has been implemented to engineer a variety of proteins including antibodies, receptors, ligands, and enzymes. The open reading frame of the CLCF1 gene was cloned into the yeast surface display plasmid pCTcon2 and transformed into EBY100 (FIG. 5, panel A). The transformed yeast demonstrated low expression of CLCF1 compared to CNTFR, which may suggest lower stability or solubility of CLCF1 (FIG. 5, panel B). The CLCF1 expressing population bound 20 nM wild-type CNTFR-HIS (wtCNTFR-HIS), confirming its functionality.

Error prone PCR was used to create a randomly mutated yeast-displayed CLCF1 library with an estimated diversity of about $1\times10^8$. The resulting library was transformed and displayed on yeast. Using equilibrium binding conditions and screened by flow cytometric sorting (FACS), high throughput screening of the CLCF1 library using wtCNTFR-HIS was performed to enrich variants showing increased CLCF1 binding. Expression signal was used to normalize CNTFR binding to distinguish high expressers from high affinity binders. Screening stringency was increased throughout sorting by decreasing the concentration of wtCNTFR-HIS incubated with the library. After 4 rounds of FACS a consensus mutation, Q96R ($K_d$=7.9 nM), emerged as shown in FIG. 6. Quantitative yeast-displayed binding studies suggested that two additional mutations, L86F ($K_d$=3.1 nM) and H148R ($K_d$=4.2 nM), additively increased the binding for CNTFR with the variant with all three mutations leading to 10-fold higher apparent binding affinity ($K_d$=0.83 nM). Thus a variant containing the three mutations (named FRR-CLCF1) was chosen for further characterization (FIG. 7).

Binding Affinities of Recombinant Engineered CLCF1 Variants

The CLCF1 variants isolated from screening were cloned into the pET28b bacterial expression plasmid and expressed and purified. To measure binding affinity, recombinant CLCF1 variants or wild-type CLCF1 were incubated with wtCNTFR-Fc at room temperature for 4 hours. A sandwich ELISA was performed using an anti-mouse Fc antibody as a capturing agent for wtCNTFR-Fc, followed by an anti-CLCF1 antibody as a detection agent for the bound complex. Compared to wild-type CLCF1 (wtCLCF1), FRR-CLCF1 exhibited higher binding affinity, with an apparent $K_d$ of approximately 0.83 nM (FIG. 8, panels A and B). ELISA was also used to measure binding interactions with the gp130 and LIFR beta receptors. FRR-CLCF1 complexed with CNTFR displayed substantially increased binding for gp130 and LIFR compared to wtCLCF1 (FIG. 8, panels C and D). These results confirmed that binding of CLCF1 and CNTFR drives their interaction with the beta receptors and demonstrates that higher binding affinity for CNTFR can lead to higher tripartite receptor complex formation.

Engineered CLCF1 is a Potent Activator of STAT3 and Induces Enhanced Cell Survival To determine whether the enhanced tripartite receptor complex formation driven by FRR-CLCF1 effectively leads to increased downstream signaling, we tested its effect on SH-SY5Y cells and human non-small cell lung cancer (NSCLC) cells. When treated with FRR-CLCF1, the cells showed higher phosphorylation of STAT3 at Tyr705 (FIG. 9, panels A and B). FRR-CLCF1 demonstrated higher STAT3 activation in E18 cells as well, indicating that affinity maturation to human CNTFR also increased the potency for rat neurons (FIG. 9, panel C). Microglia are the major inflammatory cells in the brain. Activated microglia produce inflammatory mediators such as nitric oxide, tumor necrosis factor-α, and prostaglandins and this can damage the surrounding tissues. Since STAT3 has been shown to be involved in microglia activation and inflammation in the brain can lead to adverse effect, the effect of FRR-CLCF1 on STAT3 activation in microglia was tested. In the range of concentrations tested, no activation of STAT3 was detected using FRR-CLCF1 while IL6 led to a robust STAT3 activation (FIG. 9, panel D). Importantly, FRR-CLCF1 treatment led to higher cell survival in SH-SY5Y and E18 cells (FIG. 10) suggesting that the engineered CLCF1 is a promising candidate for neuronal survival.

Engineered CLCF1 Enhances Rat Cortical Neuron Axon Regeneration

Figure 11:
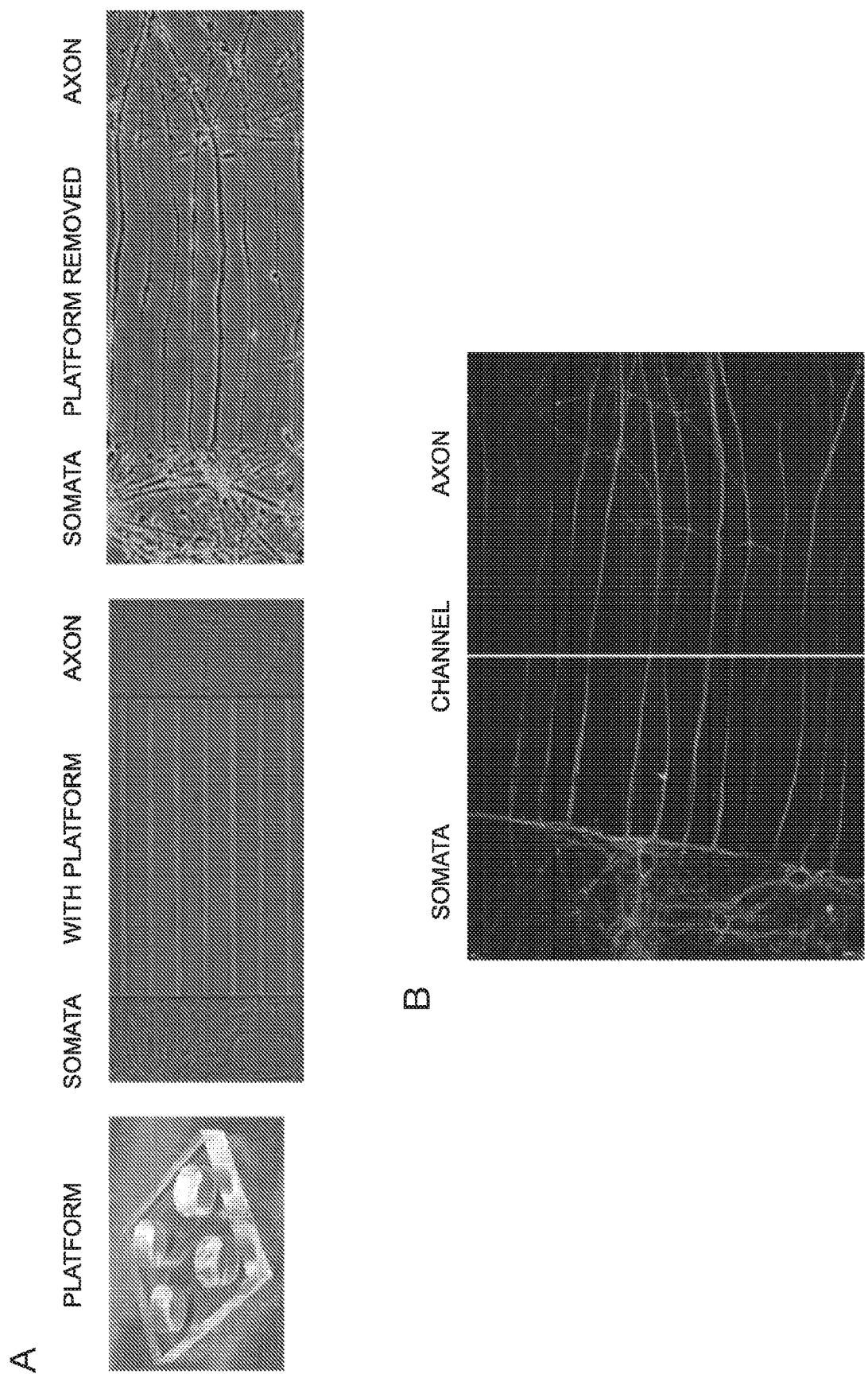
FIG. 11, panels A and B, show a microfluidic culture platform for axonal injury. E18 cells were seeded in the somata chamber and cultured for 4 days (panel A). Axons extended past the channel without detecting dendrites (panel B).
Figure 12:
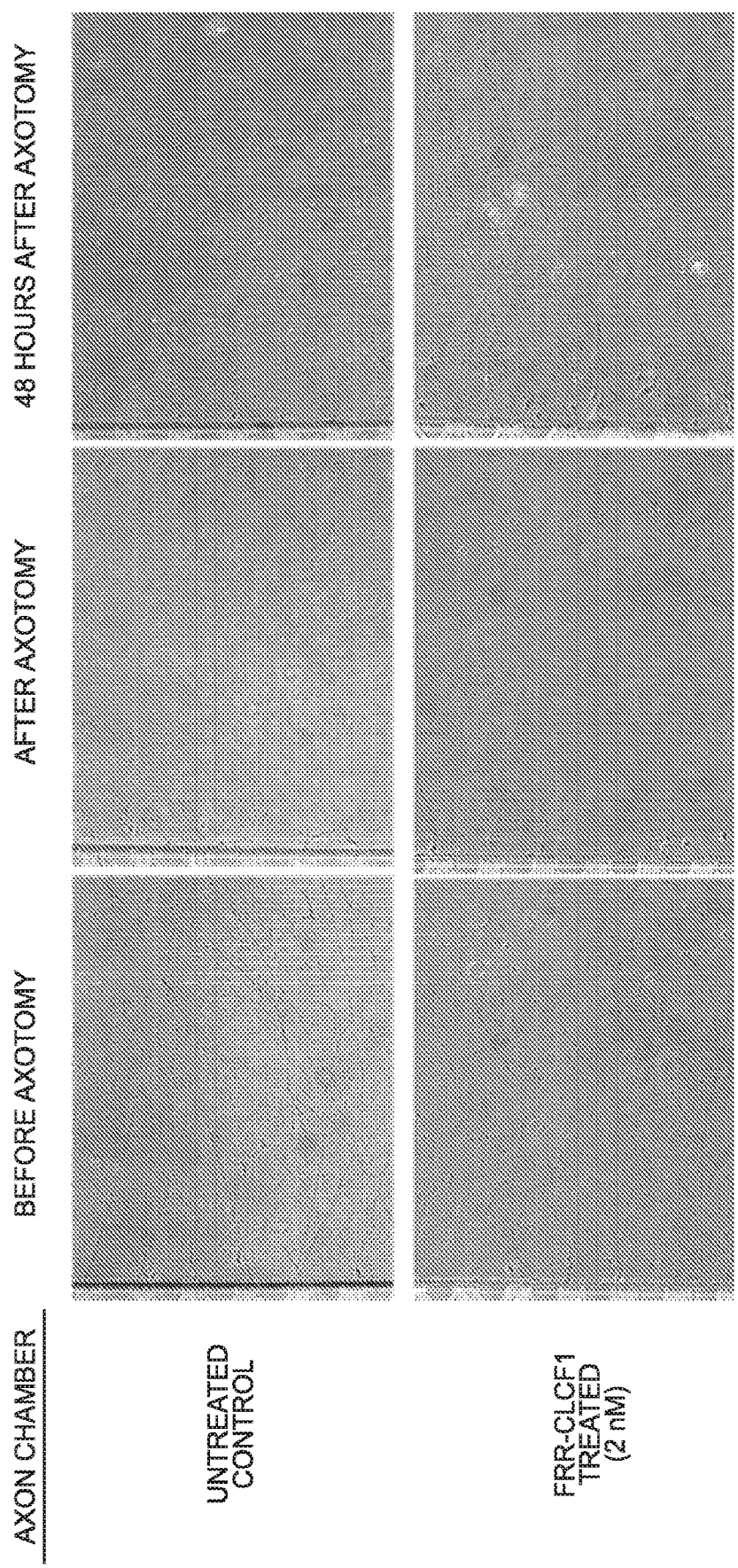
FIG. 12 shows the axonal side before, immediately after, and 48 h after axotomy of E18 cells. 2 nM FRR-CLCF1 treatment led to higher axon regrowth compared to untreated control.
Figure 13:
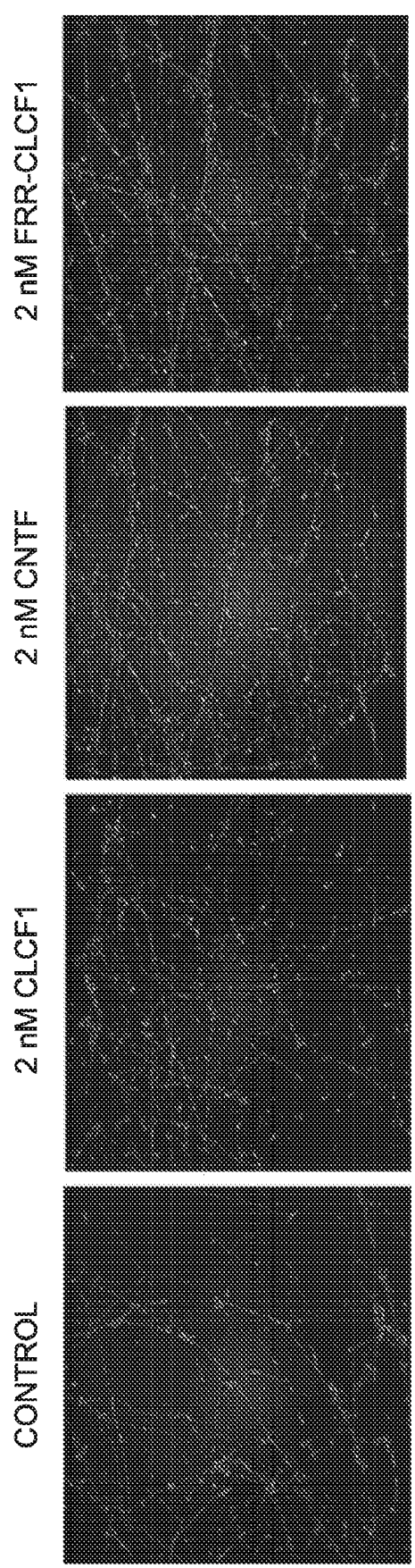
FIG. 13 shows the axonal side 48 h after axotomy of E18 cells. 2 nM FRR-CLCF1 treatment led to higher axon regrowth compared to untreated control and 2 nM CLCF1. Anti-tau antibody was used to fluorescently image axons.

Axon formation is the basis of neuronal connectivity. In a damaged brain, damaged axons can sprout nerve endings and rewire the network to compensate for damage, which is part of a process called neuroplasticity. Different growth factors and cytokines are known to be involved in this process. To test whether FRR-CLCF1 can also facilitate axonal regeneration, a microfluidic device was used for compartmentalizing, isolating, and directing the growth of axons. Rat embryonic neurons (E18) were seeded and cultured for 4 days in the somata chamber, leading to outgrowth of axons into the axon chamber, while dendrites stayed within the somata chamber (FIG. 11, panels A and B). Using this device as an in vitro model of axonal injury, selective lesion of axons were performed by aspirating only the contents of the axon chamber. It was observed that treatment with FRR-CLCF1 led to higher regrowth of axons within 48 hours compared to untreated control (FIG. 12). Furthermore, the level of axonal regeneration induced by FRR-CLCF1 was higher than that of wtCLCF1 and comparable to CNTF (FIG. 13).

Materials and Methods

Cells and Reagents

SH-SY5Y growth media was Dulbecco's Modified Eagle Media (Invitrogen) with 10% fetal bovine serum (FBS) (American Type Culture Collection), 1% penicillin-streptomycin. Embryonic rat cortical neurons (E18) were plated in plating media (Neurobasal (Gibco), 2% B27 (Gibco), 1% Glutamax, and 1% FBS) for overnight and cultured in culture media (Neurobasal (Gibco), 2% B27 (Gibco), 1% Glutamax, and 10% FBS).

Preparation of the Yeast-Displayed CLCF1 Library

Yeast-displayed protein library was prepared as reported in Van Deventer and Wittrup (2014) *Methods Mol Biol* 1131:151-181. Briefly, DNA encoding human CLCF1 was cloned into the pCTcon2 yeast display plasmid using NheI and BamHI restriction sites. A DNA library was created by error-prone PCR using the CLCF1 sequence as a template, and mutations were introduced by low-fidelity Taq polymerase (Invitrogen) and 55 mM $MgCl_2$. Separate PCR reactions were performed using different concentrations of MnCl2 (0, 0.01, 0.05, 0.1, and 015 mM). Products from these reactions were purified using gel electrophoresis. Purified mutant cDNA and linearized plasmid were electroporated into EBY100 yeast, where they were assembled in vivo through homologous recombination. Library size was estimated to $8.1 \times 10^7$ by dilution plating of yeast colonies. The transformed cells were selected in SDCAA media and induced for expression in SGCAA media.

Library Screening

Yeast displaying high-affinity CNTFR variants were isolated from the library using fluorescence-activated cell sorting (FACS). FACS was carried out after equilibrium binding where yeasts were incubated at room temperature in phosphate-buffered saline with 1 mg/mL BSA (PBSA) with the following concentrations of HIS tagged CNTFR: for sort 1, 20 nM CNTFR for 3 h; for sort 2, 2 nM CN TFR for 6 h; for sort 3, 0.5 nM CNTFR for 12 h. After incubation with CNTFR, yeast were pelleted, washed and resuspended in PBSA with a 1:500 dilution of chicken anti-c-Myc (Invitrogen) for 30 min at 4 C. Yeast were then washed and pelleted, and secondary labeling was performed on ice for 30 min using PBSA with a 1:100 dilution of goat anti-chicken PE and mouse anti-HIS Hilyte Fluor 488. Sorted clones were propagated and subjected to further rounds of FACS. After the last round of screening plasmid DNA was recovered using a Zymoprep kit (Zymo Research Corp), transformed into DH10B electrocompetent cells, and isolated using plasmid miniprep kit. Sequencing was performed by MC Lab. Samples were analyzed on a FACSCalibur (BD Biosciences), and data were analyzed using FlowJo software (Treestar Inc).

Yeast Cell Surface CLCF1-CNTFR Binding Assays

Yeast displaying CLCF1 constructs were incubated with varying concentrations of CNTFR for 12 h at room temperature to reach equilibrium binding. This was followed by washing with BPBS and resuspension in PBSA with 1:500 ratio of chicken anti-c-Myc (Invitrogen) for 30 min at 4 C. Yeast were then washed and pelleted, and secondary labeling was performed on ice for 30 min using PBSA with 1:100 dilution of goat anti-chicken PE (Santa Cruz) and mouse anti-HIS Hilyte Fluor 488 (Anaspec). Then samples were washed and analyzed by flow cytometry using Accuri (BD Biosciences). Samples were analyzed on BD Bioscience software, and data were analyzed using FlowJo software. $K_d$ values were determined by fitting to a four-parameter sigmoidal curve. Error bars represent the standard deviation of triplicate experiments.

ELISA-Based CLCF1-CNTFR Binding Assays

To measure the solution-phase binding interaction between the CLCF1 constructs and CNTFR, different concentrations of soluble, recombinant CLCF1 variants and wtCLCF1 were incubated with 2 nM CNTFR-Fc in BPBS for 12 h at room temperature. The mixture was then added to 96-well plates coated with anti-mouse-Fc antibody for 1 h followed by washing with BPBS twice. Subsequently, the wells were incubated with 1:1000 diluted anti-CLCF1 rabbit antibody for 2 h at room temperature then washed four times with BPBS. The wells were incubated with a 1:1000 diluted HRP conjugated anti-rabbit antibody for 2 h at room temperature, and washed four times with BPBS. 1-Step Ultra TMB ELISA was used for the readout, which was measured using a plate reader (Tecan).

To detect binding interactions between CLCF1-CNTFR complex and gp130 or LIFR, 2 nM soluble CLCF1 variants or wtCLCF1 were incubated with 2 nM CNTFR-HIS and gp130-Fc or LIFR-Fc for 3 h at room temperature. The mixture was then added to 96-well plates coated with anti-HIS rabbit antibody for 1 h followed by washing with BPBS twice. Subsequently, the wells were incubated with 1:1000 diluted HRP conjugated anti-mouse antibodies for 2 hr at room temperature, washed four times with BPBS. 1-Step Ultra TMB ELISA was used for the readout, which was measured using a plate reader (Tecan).

Phosphorylation Assays

A549, SH-SY5Y, and E18 cells were grown to 50% confluence in 6-well plates. The cells were serum starved overnight (12 hr) before incubation with varying concentrations of CLCF1 variants or wtCLCF1 for the indicated times at 37° C. in 5% $CO_2$. The treated cells were lysed with NP-40 buffer (20 mM Tris pH 8.0, 137 mM NaCl, 10% glycerol, and 1% IGEPAL/NP40) containing protease and phosphatase inhibitors (Thermo Fisher Scientific) for 1 h at 4° C. Then equal amounts of lysate were loaded on Bis-Tris gels (GenScript) and transferred onto nitrocellulose membrane (Thermo Fisher Scientific). The blotted membrane was blocked with 5% BSA. Anti-STAT3 antibodies were from Cell Signaling. Anti-β-tubulin antibody was from Covance. All secondary antibodies were purchased from Jackson ImmunoResearch. SuperSignal West Femto Maximum Sensitivity Substrate was used as a HRP substrate (Thermo Fisher Scientific). Chemiluminescence was detected using the ChemiDoc XRS System.

Cell Survival Assays $5 \times 10^3$ SH-SY5Y and $2 \times 10^4$ E18 cells were seeded and grown for 24 h, and serum starvation was induced by incubating for 24 h in DMEM with 0.1% BSA for SH-SY5Y, and neurobasal with 0.1% BSA for E18. Varying concentrations of wtCLCF1, FRR-CLCF1, and CNTF were then added and incubated for 72 h at 37° C. and 5% CO2. Next, AlamarBlue reagent (Thermo Fisher Scientific) was added to each well and incubated for 1 h at 37° C. and 5% $CO_2$. 560EX nm/590EM nm. Error bars represent the standard deviation of triplicate wells. Data was measured against negative control with only media.

Microfluidic Culture Platform for In Vitro Axonal Injury Assay

Microfluidic culture devices that compartmentalize neurons were used as reported. Taylor et al. (2005) *Nat Methods* 2:599-605. Briefly, the PDMS and glass coverslips were sterilized with 70% ethanol. The cleaned glass coverslips were immersed in sterile solution of 1.0 mg/mL poly(l-lysine) (PLL) in water for 24 h before use. Sealing the PDMS piece to the PLL coated glass coverslip by conformal contact formed the enclosed channels. The device was filled with culture media for 3 h. Immediately before cell seeding culture media was aspirated and $3 \times 10^6$ cells/mL in 20 μL of culture media were added to each of the somal side of the chamber. After incubating in a humidified incubator for 10 min to allow cells to attach rest of the chamber were filled with 150 μL of culture media. To create axonal injury vacuum aspiration was applied in the axonal compartment for 5 s. Quickly 150 μL of culture media mixed with wtCLCF1, FRR-CLCF1, and CNTF were added to the empty reservoirs.

For immunohistochemistry, the devices were separated from the slides, and the cultures were fixed using 4% paraformaldehyde for 30 min at room temperature. The cultures were then washed twice with phosphate-buffered saline (PBS) for 5 min and permeabilized using PBS with 0.2% Triton X-100 for 30 min. To block nonspecific binding, the slides were incubated in PBS with 0.2% Triton X-100 with 5% BSA for 1 h. The primary antibodies were incubated in PBS with 0.2% Triton X-100 and 5% BSA at room temperature for 1 h. Monoclonal MAP2 antibody was purchased from Sigma-Aldrich, and polyclonal Tau antibody was purchased from Abcam.

Statistical Analysis

Difference between groups in all experiments were examined for statistical significance using a two-tailed Student's t-test. $P<0.05$ was considered significant.

Example 2—Engineering Variant CNTFR Ligands for Reduced Binding of gp130 and/or LIFR It was hypothesized that variant CNTFR ligands could be employed as a therapeutic to reduce CNTFR signaling, e.g., to treat a cell proliferative disorder, such as cancer. In this particular example, CLCF1 variants were generated and assessed for binding affinity to gp130 and/or LIFR, although the materials and methods employed in this example are readily applicable to other CNTFR ligands, such as CNTF and neuropoetin (NP1).

Screening Shuffled CLCF1 Library

Experimental and computational studies have shown that it is critical for a small protein to bind to its target with affinity in the low nM to pM range to have therapeutic efficacy on short time scale. To further enhance the binding affinity of CLCF1 to effectively compete against the wild type CLCF1 (wtCLCF1), another library was created and screened starting from the final population sorted in Example 1. Instead of introducing additional mutations, a PCR based recombination approach was used to shuffle segments from randomly selected variants to determine whether combining lowly enriched mutations, in addition to the mutations in FRR-CLCF1, can further enhance the binding affinity for CNTFR. From the previously sorted randomly mutagenized CLCF1 library (FIG. 6), 20 clones were randomly selected to be shuffled using the Staggered Extension Process (StEP) method. In StEP, primers anneal and extend in a step whose brief duration and suboptimal extension temperature limit primer extension. The partially extended primers randomly reanneal to different parent sequences throughout the multiple cycles, creating various recombinants. To impose increased stringency with the shuffled library, a combination of equilibrium binding and kinetic off-rate screens was used. After 3 rounds of screening different combinations of five consensus mutations (L86F, Q96R, H148R, W169L, K180R) emerged (FIG. 14).

Characterization of Shuffled CLCF1

Quantitative yeast-displayed binding studies suggested that each of these mutations contributed to the binding affinity for CLCF1, and when combined with one additional mutation, Y22C, the resulting variant demonstrated the highest binding affinity (FIG. 15). CNTFR activates gp130 and LIFR by first, binding to CLCF1, then binding to gp130 and LIFR to form a tripartite receptor complex. Unexpectedly, yeast-displayed CLCF1 did not interact with the beta receptors even in the presence of soluble CNTFR (data not shown). Given relatively smaller size of CLCF1 (20 kDa) compared to other receptor subunits, it was hypothesized that steric hindrance imposed by fusing CLCF1 to yeast Aga2 prevented CLCF1-CNTFR to bind to the beta receptors.

Figure 16:
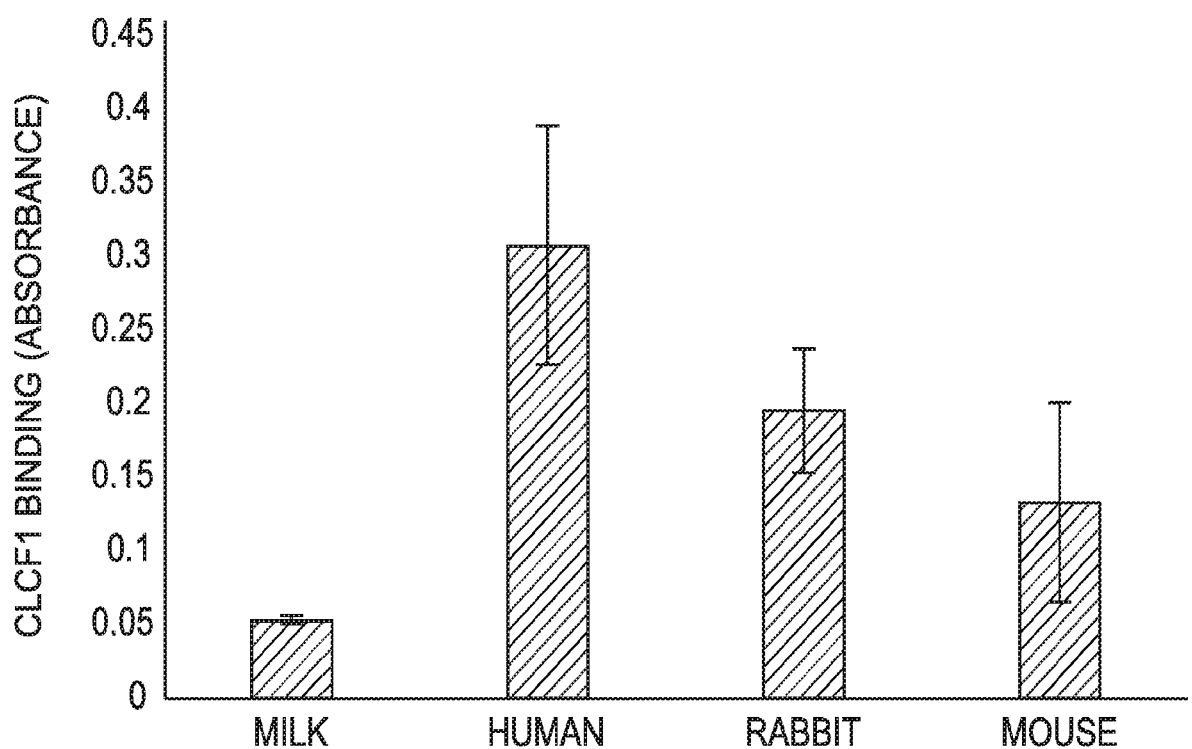
FIG. 16 shows data relating to soluble CLCF1 binding to albumin (50 mg/ml) coated surfaces. CLCF1 binds the least to milk coated surface.

To test for interactions with the beta receptors each of the variants were produced as soluble constructs by recombinant expression in *E. coli* and purified using reverse-phase high-performance liquid chromatography (RP-HPLC). Interestingly, soluble CLCF1 variants adhered to BSA coated plates but not milk coated plates, suggesting that they may interact with albumin (FIG. 16). A wide variety of molecules are known to interact with albumin to increase their serum half-life and although it has not been reported, binding of CLCF1 to albumin may play an important role in vivo.

Shuffled CLCF1 has Reduced Binding for gp130

Figure 17:
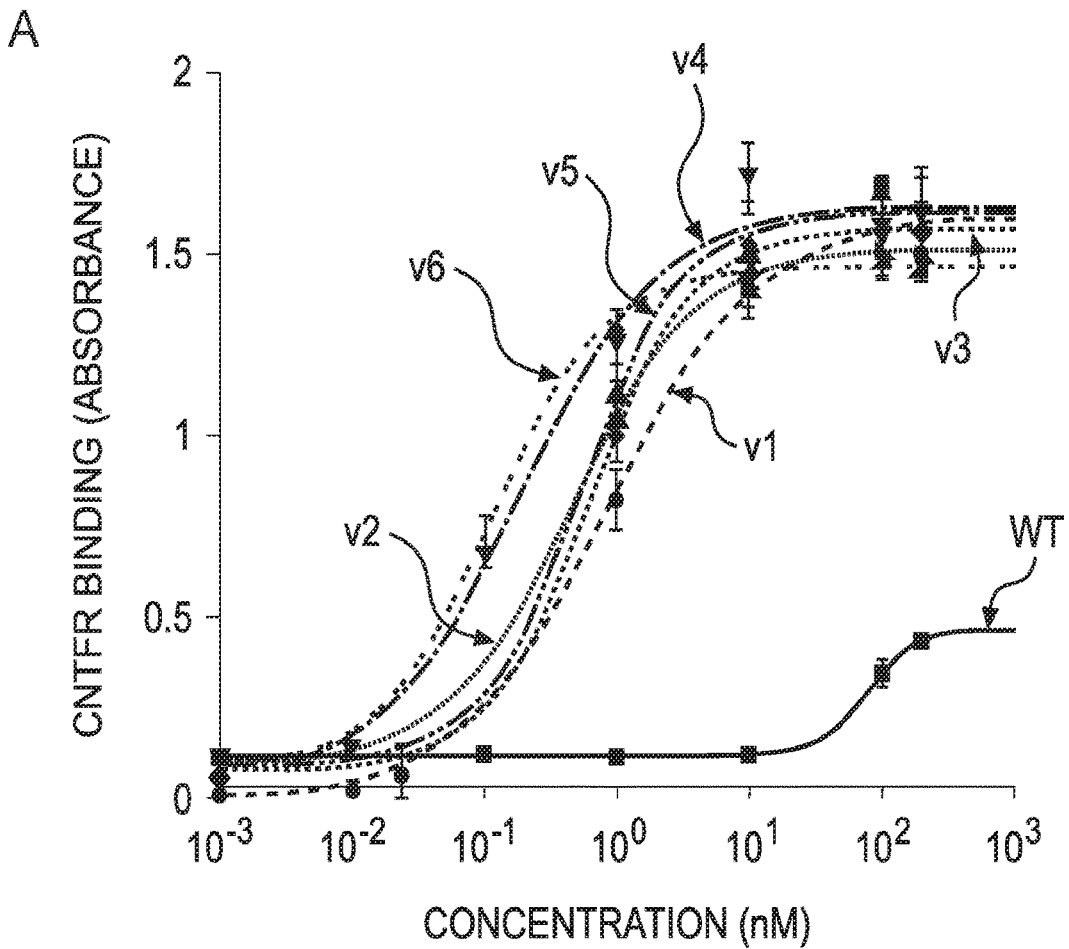
FIG. 17, panels A and B, shows data relating to the characterization of soluble CLCF1 variants. Panel A: Binding interaction of soluble CLCF1 constructs with soluble CNTFR. Panel B: $K_d$ values of soluble CLCF1 constructs.

Consistent with the yeast displayed constructs, among the soluble constructs the clone with all 6 mutations demonstrated the highest binding affinity for CNTFR (FIG. 17). Indeed, when the variants were produced as soluble constructs, they bound to yeast displayed CNTFR, soluble gp130 and LIFR. This was subsequently confirmed using a cell-free ELISA method. Y22C, W169L, and K180R each contributed to binding to CNTFR, decreasing $K_d$ of FRR-CLCF1 from 869 pM to 464 pM, 640 pM, and 559 pM respectively. A variant with all of the mutations combined showed the highest binding affinity with the $K_d$ of 115 pM (FIG. 18). Unexpectedly, Y22C, W169L, and K180R decreased binding for gp130 with the combined mutations leading to the lowest binding while the mutations led to increased LIFR binding through increased CNTFR binding (FIG. 18). Because reduced binding interaction with beta receptors is desirable for antagonizing activation of CNTFR-CLCF1 mediated pathways, the clone with all six mutations, which was named sfCLCF1 (shuffled CLCF1) was selected for further studies.

Alanine Substitution to Residues F151 and K154 Leads to Reduced Binding for LIFR Despite the decreased binding for gp130, even minimal interaction with the beta receptors, combined with the increased affinity for CNTFR, can activate the downstream signaling pathways. To further reduce interactions with the beta receptors, modifications that would decrease the binding of LIFR was sought. Evolutionarily IL-6 cytokines have the conserved sequence FXXK, which has been shown to contribute to LIFR binding. It has been suggested that F151 and K154 may also be important residues for CLCF1 binding to LIFR, although this had not been experimentally confirmed. Peret et al. (2004) J Biol Chem 279:43961-43970. Substitution of these residues with alanine effectively decreased the LIFR signal both on wtCLCF1 and engineered CLCF1 constructs (FIG. 19).

Engineered CLCF1 does not Activate STAT3 and Competitively Inhibits wtCLCF1 Induced STAT3 Activation and Cell Survival Based on the results from screening and alanine substitutions, constructs with different binding properties were prepared (FIG. 20). To examine how these constructs activate the downstream signaling pathways, they were treated on A549 cells. As shown in Example 1, a variant with mutations that increased affinity for CNTFR but did not decrease binding for gp130 (FRR-CLCF1) increased STAT3 phosphorylation (FIG. 6, panel A). The construct that contained gp130 reducing mutation but increased affinity for CNTFR (sfCLCF1) showed partial agonist activity while those containing LIFR reducing mutations (FRRAA-CLCF1 and sfAA-CLCF1) showed no detectable STAT3 activation. When these constructs were co-incubated with wtCLCF1, the construct with high affinity for CNTFR and reduced binding for gp130 and LIFR (sfAA-CLCF1) decreased STAT3 activation (FIG. 6, panel B). Therefore, sfAA-CLCF1 was chosen for further characterization and named "enCLCF1" (engineered CLCF1) for convenience. The amino acid sequence of enCLCF1 is provided in Table 2 above (SEQ ID NO:6).

enCLCF1 Decreases In Vitro Cell Survival

To test the effect of enCLCF1 treatment on cell survival, NSCLC cells A549 and H23 were serum starved overnight and treated with 50 nM wtCLCF1 and different concentrations of enCLCF1 for 72 h. In a concentration-dependent manner, enCLCF1 inhibited CLCF1 induced survival in both cell lines (FIG. 22).

In Vivo Effects of enCLCF1

To test the in vivo effect of enCLCF1 treatment, a study was conducted using 7 pairs of mice bearing subcutaneous A549 xenograft tumors. A549 cells were subcutaneously injected and grown on two opposing flanks of each mouse. After the tumor sizes grew to approximately 100 $mm^3$, the mice were injected with 1 mg per body weight dose of an enCLCF1 or saline control, three times weekly for 4 weeks. Treatment with the enCLCF1 significantly decreased tumor growth compared saline control and the treatment displayed no adverse events or signs of toxicity with this dosing regimen (FIG. 23).

Materials and Methods

Cells and Reagents

A549 was purchased from ATCC. A549 growth media was Dulbecco's Modified Eagle Media (Invitrogen) with 10% fetal bovine serum (FBS) (American Type Culture Collection), 1% penicillin-streptomycin. H23 cells were grown in RPMI-1640 Medium with 10% FBS, 1% penicillin-streptomycin. Anti-CLCF1 and anti-CNTFR antibodies were purchased from Abcam. Anti-HIS Hilyte Fluor 488 antibody was purchased from Anaspec and anti-mouse Alexa 488 antibody was from Invitrogen. Anti-STAT3 antibodies were from Cell Signaling. Anti-β-tubulin antibody was from Covance. All secondary antibodies were purchased from Jackson ImmunoResearch, and 1-Step Ultra TMB ELISA was from Pierce.

Recombinant CLCF1 Production cDNA of CLCF1 constructs were clones into pET28b plasmid with inducible lac promoter using BsaI and XhoI restriction sites and amplified in DH10B cells. For expression, purified plasmids were transformed into Rosetta gami cells. Inclusion body was solubilized in 60% ddH2O, 40% acetonitrile, 0.1% TFA) containing 5 mM DTT. Then reversed-phase high-performance liquid chromatography (RP-HPLC) was used to purify CLCF1. Protein purity was further analyzed using SDS-PAGE and quantified using a Nanodrop 2000 (Thermo Scientific). 39,549 was used for the extinction coefficient.

Soluble CNTFR, LIFR and gp130 Production cDNA of CNTFR (1-342), LIFR (1-534), and gp130 (1-619) genes were cloned into Add2 plasmid and amplified in DH10B cells. For expression, purified plasmids were transformed into human embryonic kidney 293 (HEK 293) cells using polyethylenimine (PEI). Briefly, PEI was dissolved in dH2O to 1 g/L. For 500 mL transfection volume, 0.5 mg of purified DNA and 1 mL of PEI was dissolved in 10 mL of OptiPro Serum Free Media each, then mixed immediately. After 15 minutes the solution was added dropwise to 500 mL of cells. The cells were incubated on a rotary shaker at 120 RPM in a humidified incubator at 37° C. and 5% $CO_2$. Fc fusion proteins were purified using protein A column and HIS tag fusion proteins were purified using nickel column. The proteins were then further purified using size exclusion FPLC. Following extinction coefficients were used: 70,275 for soluble CNTFR variants, 206,410 for CNTFR-Fc variants, 130,470 for soluble gp130, 326,800 for gp130-Fc, 98,610 for soluble LIFR, and 263,080 for LIFR-Fc.

Preparation of Yeast-Displayed CLCF1 Library

From the population isolated in the final sort round with randomly mutagenized CLCF1 library (Example 1), 20 non-repeating sequences were selected randomly. 1 ng of each of the templates was combined with 1 ng of wtCLCF1 sequence and 21 ng total template was mixed with the final concentrations of 0.15 μM each primer, 1×PCR buffer, 200 μM dNTP mix, 1.5 mM MgCl2, 2.5 U Taq polymerase in sterile dH2O to 50 μL. The extension protocol was run for 100 cycles using the following parameters: 94° C. for 30 s (denaturation) and 55° C. for 10 s. Products form these reactions were purified using gel electrophoresis. Purified mutant cDNA and linearized plasmid were electroporated in EBY100 yeast, where they were assembled in vivo through homologous recombination. Library size was estimated to $7.4\times10^7$ by dilution plating.

Library Screening

FACS rounds for shuffled library was done using a single round of equilibrium binding sort using 0.5 nM of CNTFR followed by two rounds of kinetic off-rate sorts. For kinetic off-rate sorts yeasts were incubated with 2 nM CNTFR for 2 h at room temperature, after which cells were washed twice to remove excess unbound CNTFR and resuspended in PBSA containing 20 nM wtCLCF1 to render unbinding events irreversible. For the length of the unbinding steps, 10 h was used for sort 2 and 24 h was used for sort 3. Labeled yeasts were sorted by FACS using a BD Aria II flow cytometer and BD FACSCalibur. Sorts were conducted such that the 0.5-1% of clones with the highest CLCF1 binding/c-Myc expression ratio (to normalize by expression) were selected, enriching the library for clones with the highest binding affinity to CLCF1. Sorted clones were propagated and subjected to further rounds of FACS. After the last screening, plasmid DNA was recovered using a Zymoprep kit (Zymo Research Corp), transformed into DH10B electrocompetent cells, and isolated using plasmid miniprep kit. Sequencing was performed. Samples were analyzed on a FACSCalibur and data were analyzed using FlowJo software.

Cell-Free Binding Assays 96-well plates were coated with 10 µg/mL of anti-HIS antibody overnight and blocked with 5% milk for 1 h. The plates were then washed twice with BPBS. Different concentrations of soluble constructs of HIS-tagged CLCF1 variants were incubated with 2 nM CNTFR-Fc in BPBS for 12 h at room temperature. The mixture was then added to 96-well plates coated with anti-HIS antibody for 1 h followed by washing with BPBS twice. Subsequently, the wells were incubated with 1:1000 diluted HRP conjugated anti-mouse antibody for 1 h at room temperature then washed four times with PBS. 1-Step Ultra TMB ELISA (Thermo Fisher Scientific) was used for the readout detected using a plate reader (Tecan).

Phosphorylation Assays

A549 cells were grown until 50% confluence in 6-well plates. The cells were incubated in 2 nM or 10 nM of CLCF1 constructs for 20 min at 37° C. in 5% $CO_2$, then lysed with NP-40 buffer containing protease and phosphatase inhibitor (Thermo Scientific). Equal amounts of lysate were loaded on Bis-Tris gels and transferred onto nitrocellulose membrane. Western Blot analysis was performed with the reagents above. Chemiluminescence was detected using the Chemi-Doc XRS System (Bio-Rad). NP-40 buffer was composed of 20 mM Tris pH 8.0, 137 mM NaCl, 10% glycerol, and 1% IGEPAL/NP40. For analyzing competitive inhibition of wtCLCF1 mediated STAT3 activation, 2 nM or 10 nM of CLCF1 constructs were mixed with 40 nM of wtCLCF1 to treat A549 cells. The rest of the steps are same as above.

Cell Survival Assays $5 \times 10^3$ A549 and H23 cells were seeded and grown for 24 h, and serum starvation was induced by incubating for 24 h in DMEM with 0.1% BSA. CLCF1 and CNTFR constructs were then added and incubated for 72 h at 37° C. and 5% $CO_2$. Next, AlamarBlue reagent was added to each well and incubated for 1 h at 37 C and 5% $CO_2$. The cell metabolic activity was detected by measuring fluorescence using 560EX nm/590EM nm. Error bars represent the standard deviation of triplicate wells. Data was measured against negative control with only media.

In Vivo Tumor Models

To generate NSCLC xenograft model, $1 \times 10^6$ A549 cells were injected subcutaneously in the two lower flanks of NSG mice (NOD, SCID, gamma). The tumors were allowed to grow to on average 100 $mm^3$ before dosing. enCLCF1 was administered at 1 mg per kg body weight three times weekly via intraperitoneal injection for 31 days and the tumor volume was calculated using volume=$\pi/6 \times$(length)$\times$(width)$^2$.

Example 3—Expression of CLCF1 and CNTFR in Lung Cancer

Figure 24:
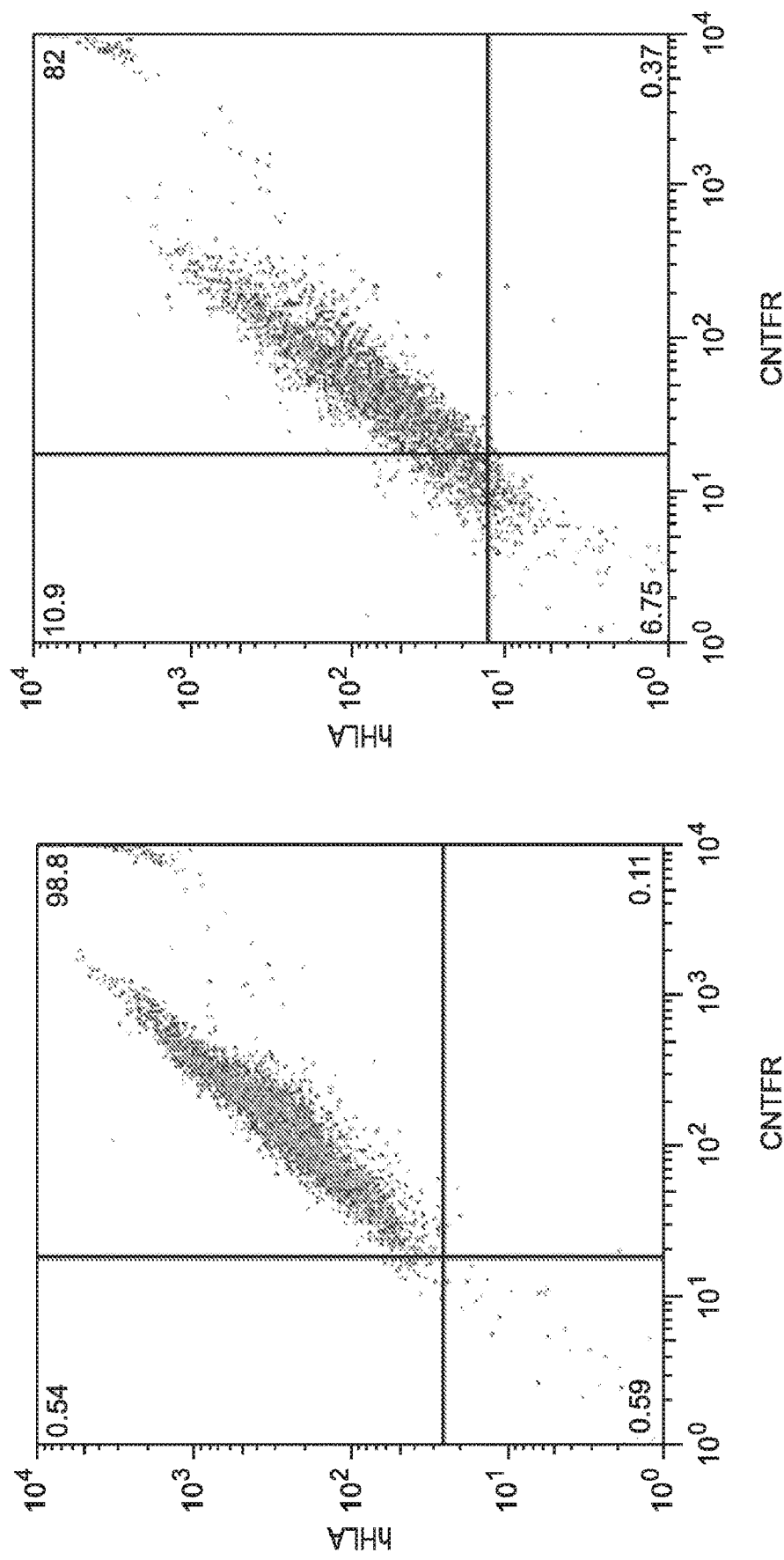
FIG. 24, panels A-D, provide data demonstrating that CLCF1 and CNTFR are expressed in non-small cell lung cancer (NSCLC).
Figure 24:
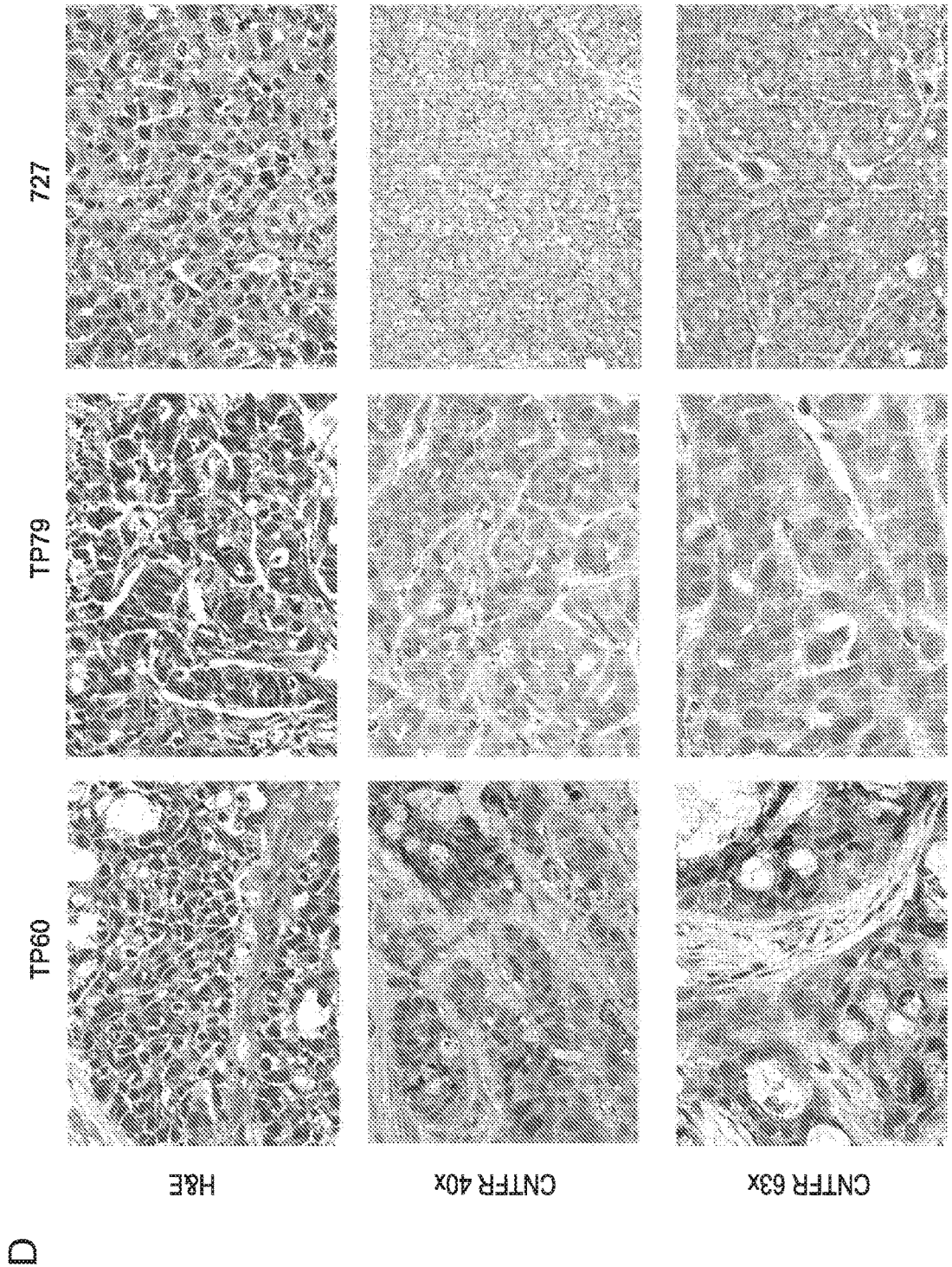

While cancer-associated fibroblasts (CAFs) express CLCF1 and may be the source for this cytokine in vivo, the present study determined that NSCLC cell lines also secrete CLCF1, suggesting the existence of both paracrine and autocrine signaling mechanisms for this cytokine (FIG. 24, panel A). The receptor for CLCF1, CNTFR, was also determined to be expressed on all NSCLC cell lines and patient-derived xenograft (PDTX) models tested (FIG. 24, panels B and C). Expression of CNTFR was also observed by immunohistochemistry in PDTX models and in tumors generated in the KrasG12D; P53f/f genetically-engineered mouse model (FIG. 24, panel D). Taken together these results suggest that the CLCF1-CNTFR signaling axis is active in lung adenocarcinoma and that it may have a role in oncogenesis, particularly in tumors driven by oncogenic Kras.

Notwithstanding the appended claims, the disclosure is also defined by the following clauses:

1. A ciliary neurotrophic factor receptor (CNTFR) ligand selected from the group consisting of:
   a CNTFR ligand that exhibits increased binding affinity for CNTFR relative to the corresponding wild-type CNTFR ligand,
   a CNTFR ligand that results in reduced binding affinity of glycoprotein 130 (gp130), leukemia inhibitory factor receptor (LIFR), or both, for a complex comprising the CNTFR ligand and CNTFR, relative to the binding affinity for a complex comprising the corresponding wild-type CNTFR ligand and CNTFR, and
   a CNTFR ligand that exhibits increased binding affinity for CNTFR relative to the corresponding wild-type CNTFR ligand and results in reduced binding affinity of gp130, LIFR, or both, for a complex comprising the CNTFR ligand and CNTFR, relative to the binding affinity for a complex comprising the corresponding wild-type CNTFR ligand and CNTFR.

2. The CNTFR ligand of Clause 1, wherein the CNTFR ligand is a ciliary neurotrophic factor (CNTF) ligand, a cardiotrophin-like cytokine factor 1 (CLCF1) ligand, or a neuropoetin (NP) ligand.

3. The CNTFR ligand of Clause 1 or Clause 2, wherein the CNTFR ligand exhibits increased binding affinity for CNTFR relative to the corresponding wild-type CNTFR ligand.

4. The CNTFR ligand of Clause 3, wherein the CNTFR ligand is a CLCF1 ligand comprising one or more mutations at amino acid positions 86, 96, 148, 169, 180, or any combination thereof, relative to a CLCF1 ligand having the amino acid sequence set forth in SEQ ID NO:3.

5. The CNTFR ligand of Clause 4, wherein the CLCF1 ligand comprises one or more amino acid substitutions selected from the group consisting of: L86F, Q96R, H148R, W169L, K180R, and any combination thereof, relative to a CLCF1 ligand having the amino acid sequence set forth in SEQ ID NO:3.

6. The CNTFR ligand of any one of Clauses 1 to 5, wherein the CNTFR ligand results in reduced binding affinity of gp130, LIFR, or both, for a complex comprising the CNTFR ligand and CNTFR.

7. The CNTFR ligand of Clause 6, wherein the CNTFR ligand results in reduced binding affinity of gp130 for a complex comprising the CNTFR ligand and CNTFR.

8. The CNTFR ligand of Clause 7, wherein the CNTFR ligand is a CLCF1 ligand comprising one or more mutations at amino acid positions 22, 169, 180, or any combination thereof, relative to a CLCF1 ligand having the amino acid sequence set forth in SEQ ID NO:3.

9. The CNTFR ligand of Clause 8, wherein the CLCF1 ligand comprises one or more amino acid substitutions selected from the group consisting of: Y22C, W169L, K180R, and any combination thereof, relative to a CLCF1 ligand having the amino acid sequence set forth in SEQ ID NO:3.

10. The CNTFR ligand of any one of Clauses 6 to 9, wherein the CNTFR ligand results in reduced binding affinity of LIFR for a complex comprising the CNTFR ligand and CNTFR.

11. The CNTFR ligand of Clause 10, wherein the CNTFR ligand is a CLCF1 ligand comprising one or more mutations at amino acid positions 151, 154, or both, relative to a CLCF1 ligand having the amino acid sequence set forth in SEQ ID NO:3.

12. The CNTFR ligand of Clause 11, wherein the CLCF1 ligand comprises one or more amino acid substitutions selected from the group consisting of: F151A, K154A, and F151A and K154A, relative to a CLCF1 ligand having the amino acid sequence set forth in SEQ ID NO:3.

13. The CNTFR ligand of any one of Clauses 1 to 12, wherein the CNTFR ligand is fused to a heterologous polypeptide.

14. The CNTFR ligand of Clause 13, wherein the heterologous polypeptide is an Fc domain, an albumin, a transferrin, XTEN, a homo-amino acid polymer, a proline-alanine-serine polymer, an elastin-like peptide, or any combination thereof.

15. The CNTFR ligand of Clause 14, wherein the heterologous polypeptide is an Fc domain.

16. The CNTFR ligand of Clause 15, wherein the Fc domain is a human Fc domain.

17. The CNTFR ligand of any one of Clauses 1 to 16, wherein the CNTFR ligand is conjugated to a moiety.

18. The CNTFR ligand of Clause 17, wherein the moiety is polyethylene glycol (PEG), an anti-cancer drug, a detectable label, or any combination thereof.

19. A pharmaceutical composition, comprising:
the ciliary neurotrophic factor receptor (CNTFR) ligand of any one of Clauses 1 to 18; and
a pharmaceutically acceptable carrier.

20. A method, comprising:
administering to an individual in need thereof a therapeutically effective amount of the ciliary neurotrophic factor receptor (CNTFR) ligand of any one of Clauses 1 to 18, or the pharmaceutical composition of Clause 19.

21. The method according to Clause 20, wherein the individual in need thereof has a cell proliferative disorder associated with CNTFR signaling, and the administering is effective in treating the cell proliferative disorder.

22. The method according to Clause 21, wherein the cell proliferative disorder is cancer.

23. The method according to Clause 22, wherein the cancer is lung cancer.

24. The method according to Clause 23, wherein the lung cancer is non-small cell lung cancer (NSCLC).

25. The method according to Clause 20, wherein the individual in need thereof has a neurodegenerative disorder, and the administering is effective in treating the neurodegenerative disorder.

26. The method according to any one of Clauses 20 to 25, further comprising, prior to the administering, identifying the individual as having a disorder associated with CNTFR signaling.

27. The method according to Clause 26, wherein the identifying is based on CNTFR ligand abundance in a sample obtained from the individual.

28. The method according to Clause 27, wherein the abundance is of a CNTFR ligand selected from the group consisting of: CNTF, CLCF1, NP, and any combination thereof.

29. The method according to Clause 27 or Clause 28, wherein the CNTFR ligand abundance is quantified using a soluble CNTFR polypeptide as a CNTFR ligand capture agent.

30. The method according to any one of Clauses 26 to 29, wherein the identifying is based on CNTFR abundance in a sample obtained from the individual.

31. The method according to any one of Clauses 26 to 30, wherein the identifying is based on the level of CNTFR signaling in a sample obtained from the individual.

32. The method according to Clause 31, wherein the level of CNTFR signaling in the sample is determined based on the phosphorylation status of one or more CNTFR signaling pathway molecules.

33. The method according to any one of Clauses 27 to 32, wherein the identifying is based on an immunoassay.

34. The method according to any one of Clauses 27 to 32, wherein the identifying is based on nucleic acid sequencing.

35. The method according to any one of Clauses 27 to 34, wherein the sample is a tissue sample.

36. The method according to any one of Clauses 27 to 34, wherein the sample is a fluid sample.

37. The method according to any one of Clauses 27 to 36, further comprising obtaining the sample from the individual.

38. A nucleic acid that encodes the CNTFR ligand of any one of Clauses 1 to 18.

39. An expression vector comprising the nucleic acid of Clause 38.

40. A host cell comprising the CNTFR ligand of any one of Clauses 1 to 18, the nucleic acid of Clause 38, the expression vector of Clause 39, or any combination thereof.

41. The host cell of Clause 40, wherein the host cell is a prokaryotic cell.

42. The host cell of Clause 40, wherein the host cell is a eukaryotic cell.

43. The host cell of Clause 42, wherein the eukaryotic cell is a mammalian cell.

44. The host cell of Clause 43, wherein the mammalian cell is a human cell.

45. A nucleic acid that encodes a ciliary neurotrophic factor receptor (CNTFR) ligand fused to a cell surface display protein.

46. The nucleic acid of Clause 45, wherein the CNTFR ligand is a ciliary neurotrophic factor (CNTF) ligand, a cardiotrophin-like cytokine factor 1 (CLCF1) ligand, or a neuropoetin (NP) ligand.

47. A nucleic acid that encodes ciliary neurotrophic factor receptor (CNTFR) fused to a cell surface display protein.

48. The nucleic acid of any one of Clauses 45 to 47, wherein the cell surface display protein is selected from the group consisting of: a bacterial surface display protein, a phage display protein, and a yeast display protein.

49. The nucleic acid of Clause 48, wherein the cell surface display protein is a yeast display protein.

50. The nucleic acid of Clause 49, wherein the yeast display protein is Aga2p.

51. An expression vector comprising the nucleic acid of any one of Clauses 45 to 50.

52. A host cell comprising the nucleic acid of any one of Clauses 45 to 50, or the expression vector of Clause 51.

53. A CNTFR ligand fused to a cell surface display protein, or CNTFR fused to a cell surface display protein, encoded by the nucleic acid of any one of Clauses 45 to 50 or the expression vector of Clause 51.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A cardiotrophin-like cytokine factor 1 (CLCF1) polypeptide
that exhibits increased binding affinity for ciliary neurotrophic factor receptor (CNTFR) relative to wild-type CLCF1, wherein the CLCF1 polypeptide comprises:
an amino acid sequence having at least 85% sequence identity to the amino acid sequence set forth in SEQ ID NO:3, and
an amino acid substitution selected from the group consisting of: L86F, Q96R, H148R, and any combination thereof.

2. The CLCF1 polypeptide of claim 1, comprising the amino acid substitution W169L, K180R, or both.

3. The CLCF1 polypeptide of claim 1, comprising an amino acid substitution at position 22, 169, 180, or any combination thereof.

4. The CLCF1 polypeptide of claim 3, comprising an amino acid substitution selected from the group consisting of: Y22C, W169L, K180R, and any combination thereof.

5. The CLCF1 polypeptide of claim 1, comprising an amino acid substitution at position 151, 154, or both.

6. The CLCF1 polypeptide of claim 5, comprising the amino acid substitution F151A, K154A, or both.

7. The CLCF1 polypeptide of claim 1, wherein the CLCF1-ligand is fused to a heterologous polypeptide.

8. The CLCF1 polypeptide of claim 7, wherein the heterologous polypeptide is an Fc domain, an albumin, a transferrin, XTEN, a homo-amino acid polymer, a proline-alanine-serine polymer, an elastin-like peptide, or any combination thereof.

9. The CLCF1 polypeptide of claim 8, wherein the heterologous polypeptide is an Fc domain.

10. The CLCF1 polypeptide of claim 1, wherein the CLCF1-ligand is conjugated to a moiety.

11. A pharmaceutical composition, comprising:
the CLCF1 polypeptide of claim 1; and
a pharmaceutically acceptable carrier.

12. A method, comprising:
administering to an individual in need thereof a therapeutically effective amount of the pharmaceutical composition of claim 11.

13. The CLCF1 polypeptide of claim 1, comprising two or each of the amino acid substitutions L86F, Q96R, and H148R.

14. A pharmaceutical composition, comprising:
the CLCF1 polypeptide of claim 13; and
a pharmaceutically acceptable carrier.

15. The CLCF1 polypeptide of claim 1, comprising each of the amino acid substitutions L86F, Q96R, and H148R.

16. A pharmaceutical composition, comprising:
the CLCF1 polypeptide of claim 15; and
a pharmaceutically acceptable carrier.

17. A method, comprising:
administering to an individual in need thereof a therapeutically effective amount of the pharmaceutical composition of claim 16.

18. A nucleic acid that encodes a CLCF1 polypeptide that exhibits increased binding affinity for CNTFR relative to wild-type CLCF1, wherein the CLCF1 polypeptide comprises:
an amino acid sequence having at least 85% sequence identity to the amino acid sequence set forth in SEQ ID NO:3, and
an amino acid substitution selected from the group consisting of: L86F, Q96R, H148R, and any combination thereof.

19. An expression vector comprising the nucleic acid of claim 18.

20. A host cell comprising the nucleic acid of claim 18.

* * * * *